(12) United States Patent
Coull et al.

(10) Patent No.: US 6,172,226 B1
(45) Date of Patent: Jan. 9, 2001

(54) SYNTHONS FOR THE SYNTHESIS AND DEPROTECTION OF PEPTIDE NUCLEIC ACIDS UNDER MILD CONDITIONS

(75) Inventors: James M. Coull, Westboro; Michael Egholm, Lexington, both of MA (US); Richard P. Hodge, Huntsville, AL (US); Mohamed Ismail, Bedford; S. B. Rajur, Chestnut Hill, both of MA (US)

(73) Assignee: PerSeptive Biosystems, Inc., Framingham, MA (US)

(*) Notice: Under 35 U.S.C. 154(b), the term of this patent shall be extended for 0 days.

(21) Appl. No.: 09/116,793

(22) Filed: Jul. 16, 1998

Related U.S. Application Data

(63) Continuation of application No. 08/487,666, filed on Jun. 7, 1995, now Pat. No. 6,133,444, which is a continuation-in-part of application No. PCT/US94/14742, filed on Dec. 22, 1994, which is a continuation-in-part of application No. 08/172,695, filed on Dec. 22, 1993, now abandoned.

(51) Int. Cl.$^7$ ........................ C07D 239/10; C07D 239/22
(52) U.S. Cl. ........................ 544/317; 544/298; 544/315; 544/316
(58) Field of Search ..................... 544/315, 316, 544/317, 298

(56) References Cited

U.S. PATENT DOCUMENTS

| | | | |
|---|---|---|---|
| 3,852,332 | 12/1974 | Cross et al. | 260/471 |
| 3,936,452 | 2/1976 | Nagasawa et al. | 260/251 |
| 4,001,226 | 1/1977 | Spry | 260/243 |
| 4,933,431 | 6/1990 | Domb et al. | 528/328 |
| 5,264,586 | 11/1993 | Nicolaou et al. | 548/406 |
| 5,340,716 | 8/1994 | Ullman et al. | 435/6 |
| 5,424,451 | 6/1995 | Alisi et al. | 548/429 |
| 5,455,354 | 10/1995 | Wong et al. | 546/147 |

FOREIGN PATENT DOCUMENTS

| | | |
|---|---|---|
| 646 596 A1 | 4/1995 | (EP) . |
| 672 661 A1 | 9/1995 | (EP) . |
| 672 700 A1 | 9/1995 | (EP) . |
| 672 701 A1 | 9/1995 | (EP) . |
| WO 86/05518 | 9/1986 | (WO) . |
| WO 90/02749 | 3/1990 | (WO) . |
| WO 92/20702 | 11/1992 | (WO) . |
| WO 92/20703 | 11/1992 | (WO) . |
| WO 93/12129 | 6/1993 | (WO) . |
| WO 93/25706 | 12/1993 | (WO) . |
| WO 95/01369 | 1/1995 | (WO) . |
| WO 95/04068 | 2/1995 | (WO) . |
| WO 95/08556 | 3/1995 | (WO) . |
| WO 95/17403 | 6/1995 | (WO) . |
| WO 95/23163 | 8/1995 | (WO) . |

OTHER PUBLICATIONS

Adamiak et al., "A Highly Effective Route to N,N$^I$–Disubstituted Ureas Under Mild Conditions. An Application to the Synthesis of tRNA Anticodon Loop Fragments Containing Ureidonucleosides," *Tetrahedron Letters*, 22:1935–1936 (1977).

Almarsson et al., "Peptide Nucleic Acid (PNA) Conformation and Polymorphism in PNA–DNA and PNA–RNA Hybrids," *Proc. Natl. Acad. Sci. USA*, 90:9542–9546 (1993).

Almarsson et al., "Molecular Mechanics Calculations of the Structures of Polyamide Nucleic Acid DNA Duplexes and Triple Helical Hybrids," *Proc Natl. Acad. Sci. USA*, 90, 7518–7522 (1993).

Ambrosius et al., "Peptide Analogues of the Anaphylatoxin C3a; Syntheses and Properties,"*Biol. Chem. Hoppe–Seyler*, 370:217–227 (1989).

Barany et al., "A Three–Dimensional Orthogonal Protection Scheme for Solid–Phase Peptide Synthesis Under Mild Conditions," *J. Am. Chem. Soc.*, 107:4936–4942 (1985).

Barcelo et al., "Alkyl–1–Chloroalkyl Carbonates: Reagents for the Synthesis of Carbamates and Protection of Amino Groups," *Synthesis*, 8:627–632 (1986).

Briepohl et al., "Preparation and Use of FMOC–Protected Building Blocks for the Synthesis of Peptide Nucleic Acids (PNA'S)," presented at 1st Australian Peptide Conference, Daydream Island, Great Barrier Reef, Australia, Oct. 16–21, 1994.

Chen et al., "Molecular Dynamics and NMR Studies of Single–Stranded PNAs," *Tetrahedron Letters*, 35:5105–5108 (1994).

Cherny et al., "DNA Unwinding Upon Strand–Displacement Binding of a Thymine–Substituted Polyamide to Double–Stranded DNA," *Proc. Natl. Acad. Sci. USA*, 90:1667–1670 (1993).

Chheda et al., "Synthesis of Naturally Occurring 6–Ureidopurines and Their Nucleosides," *Journal of Medicinal Chemistry*, 14:748–753 (1971).

Chollet et al., "Biotin–Labeled Synthetic Oligodeoxyribonucleotides: Chemical Synthesis and Uses as Hybridization Probes," *Nucleic Acids Research*, 13:1529–1541 (1985).

(List continued on next page.)

Primary Examiner—Mukund J. Shah
Assistant Examiner—Pavanaram K Sripada
(74) Attorney, Agent, or Firm—Testa Hurwitz & Thibeault, LLP

(57) ABSTRACT

A method is disclosed for preparing novel PNA synthons having protecting groups capable of removal under mild conditions. The PNA synthons are prepared by coupling novel N-substituted nucleobase intermediates having carbamate protection of the exocyclic amino group of the heterocycle to an amino protected backbone or an amino protected backbone ester of the amino acid N-(2-aminoethyl)-glycine. By the method of this invention, the resultant PNA synthons can have orthogonal protection of the carbamate protected nucleobase and the amino protected backbone. The PNA synthons are useful in the synthesis of peptide nucleic acids (PNAs) and other oligomers such as PNA-DNA chimeras, and may be used in automated synthesizers. Novel compositions of matter are also disclosed. In addition, a guanine PNA synthon having selective carbamate protection of the exocyclic 2-amino group with the C6 carbonyl group unprotected is disclosed.

23 Claims, 7 Drawing Sheets

OTHER PUBLICATIONS

Christensen et al., "Improved Synthesis, Purification and Characterization of PNA Oligomers," *Solid Phase Synthesis*, collected papers from Third International Symposium, Oxford, England, Aug. 31–Sep. 4, 1993 (1994).

Christensen et al., "Optimized Solid–Phase Synthesis of PNA Oligomers," Thirteenth American Peptide Symposium, Edmonton, Alberta, Canada, Jun. 20–25, 1993, Abstract P7, pp. 2–22.

Coull et al., "Optimized Solid–Phase Synthesis of PNA Oligomers," Solid Phase Synthesis, Lecture Programme and Abstract Book, Abstract 5a.2, p. 17, Aug. 31–Sep. 4, 1993, U. of Oxford, UK.

Demidov et al., "Sequence Selective Double Strand DNA Cleavage by Peptide Nucleic Acid (PNA) Targeting Using Nuclease S1,"*Nucleic Acids Research*, 21:2103–2107 (1993).

Dueholm et al., "An Efficient Synthesis of BOC–Aminoacetaldehyde and Its Application to the Synthesis of N–(2–BOC–Aminoethyl)Glycine Esters," *Organic Preparations and Procedures Int.*, 25(4):457–461 (1993).

Dueholm et al., "Peptide Nucleic Acid (PNA) with a Chiral Backbone Based on Alanine," *Bioorganic & Medicinal Chemistry Letters*, 4:1077–1080 (1994).

Dueholm et al., "Synthesis of Peptide Nucleic Acid Monomers Containing the Four Natural Nucleobases: Thymine, Cytosine, Adenine, and Guanine and Their Oligomerization, "*J. Org. Chem.*, 59:5767–5773 (1994).

Egholm et al., "Peptide Nucleic Acids (PNA). Oligonucleotide Analogues with an Achiral Peptide Backbone," *J. Am. Chem. Soc.*, 114:1895–1897 (1992).

Egholm et al., "Recognition of Guanine and Adenine in DNA by Cytosine and Thymine Containing Peptide Nucleic Acids (PNA)," *J. Am. Chem. Soc.*, 114:9677–9678 (1992).

Egholm et al., "PNA Hybridizes to Complementary Oligonucleotides Obeying the Watson–Crick Hydrogen–Bonding Rules," *Nature*, 365:566–568 (1993).

Fuller et al., "Urethane–Protected Amino Acid N–Carboxy Anhydrides and Their Use in Peptide Synthesis," *J. Am. Chem. Soc.*, 112:7414–7416 (1990).

Gambaconi–Passerini et al., "DNA Binding, Uptake, Intracellular Localization and Biological Effects of an Anti PML/RARα Peptide Nucleic Acid (PNA)," Abstract No. 2406, p. 605A.

Hanvey et al., "Antisense and Antigene Properties of Peptide Nucleic Acids," *Science*, 258:1481–1485 (1992).

Hodge et al., "Synthesis of 1– and 1,2,2'–Deuteriated Deoxyribose and Incorporation into Deoxyribonucleosides," *J. Org. Chem.*, 56: 1553–1564 (1991).

Hyrup et al., "Modification of the Binding Affinity Nucleic Acids (PNA). PNA with Extended Backbones consisting of 2–Aminoethyl–β–alanine or 3–Aminopropylglycine Units," *J. Chem. Soc., Chem. Commun.*, 518–519 (1993).

Kates et al., "A Novel, Convenient, Three–Dimensional Orthogonal Strategy for Solid–Phase Synthesis of Cyclic Peptides," *Tetrahedron Letters*, 34:1549–1552 (1993).

Kates et al., "Solid–Phase N–Glycopeptide Synthesis Using Allyl Side–Chain Protected Fmoc–Amino Acids," *Tetrahedron Letters*, 35:1033–1034 (1994).

Kingsbury et al., "The Use of Allylic Esters and Carbamates as Protecting Groups in the Synthesis of 5–Substituted Uracil Peptide Analogs," Abstracts of Papers, Abstract No. 216, 188th ACS National Meeting, Philadelphia, Pennsylvania, Aug. 26–31, 1984.

Kosynkina et al., "A Convenient Synthesis of Chiral Peptide Nucleic Acid (PNA) Monomers," *Tetrahedron Letters*, 35:5173–5176 (1994).

Letsinger et al., "Protecting Groups for Nucleosides Used in Synthesizing Oligonucleotides," *J. Am. Chem. Soc.*, 91:3356–3359 (1969).

Lyon et al., "Reaction Between 2',3',5'–Tri–O–acetyladenosine and Aryl Chloroformates. 2',3', 5'–Tri–O–acetyl–N(6)–phenoxycarbonyladenosine as an Intermediate in the Synthesis of 6–Ureidopurine Ribosides," *J.C.S., Perkin I*, 1978:131–137 (1978).

Meier et al., "Peptide Nucleic Acids (PNAs)–Unusual Properties of Nonionic Oligonucleotide Analogues," *Angew Chem. Int. Ed. Engl.*, 31:1008–1010 (1992).

Nielsen et al., "Sequence–Selective Recognition of DNA by Strand Displacement with a Thymine–Substituted Polyamide," *Science*, 254:1497–1500 (1991).

Nielson et al., "Sequence Specific Inhibition of DNA Restriction Enzyme Cleavage by PNA," *Nucleic Acids Research*, 21:197–200 (1993).

Nielson et al., "Sequence–Selective Recognition of DNA by Peptic Nucleic Acid Chimerae (PNA)," *Clinical Chemistry*, 39:715 (1993).

Ørum et al., "Single Base Pair Mutation Analysis by PNA Directed PCR Clamping," *Nucleic Acids Research*, 21:5332–5336 (1993).

PerSeptive Biosystems, "Identifying Point Mutations by PNA–Directed PCR Clamping," Practical PNA, vol. 1, Issue 1 (1995).

PerSeptive Biosystems, "PNA Oligomers as Hybridization Probes," Practical PNA, vol. 1, Issue 2 (1995).

Reese et al., "Some Observations Relating to the Oximate Ion Promoted Unblocking of Olignucleotide Aryl Esters," *Nucl. Acids Res.*, 9:4611–4626 (1981).

Robins et al., "Purine Nucleosides. XI. The Synthesis of 2'–Deoxy–9–α– and β–D–ribofuranosylpurines and the Correlation of Their Anomeric Structure with Proton Magnetic Resonance Spectra" *J. Am. Chem. Soc.*, 87:4934–4942 (1965).

Rosowky et al., $N^\epsilon$ –[[2–(Trimethylsilyl)ethoxy]carbonyl] Derivatives of Tri–L–lysine and Tetra–L–lysine as Potential Intermediates in the Block Polymer Synthesis of Macromolecular Drug Conjugates, *J. Org. Chem.*, 54:5551–5558 (1989).

Schneiderwind et al., "Die 2.2.2–Trichlor–tert–butyloxycarbonyl–Gruppe als N–Schutzgruppe bei Oligonukleotidsynthesen," *Zeitschrift Für Naturforschung*, 366:1173–1175 (1981).

Schwartz, Alan W., "The Origin of Macromolecular Chirality," *Current Biology*, 4:758–760 (1994).

Sennyey et al., "Diallyl Dicarbonate. A Convenient Reagent for the Synthesis of Allyl Carbamates," *Tetrahedron Letters*, 28:5809–5810 (1987).

Thomson et al., "Effect of Charge on PNA–DNA Binding," International Symposium on DNA–Drug Interactions, Helsingør, Denmark, Aug., 1993.

Thomson et al, "FMOC Mediated Synthesis of Peptide Nucleic Acids," *Tetrahedron*, 51:6179–6194 (1995).

Trzeciak et al., "Synthesis of 'Head–to–Tail' Cyclized Peptides on Solid Support by FMOC Chemistry," *Tetrahedron Letters*, 33:4557–4560 (1992).

Uhlmann, et al., "New PNA/DNA–Analogs with Biomembrane–Penetrating Properties," abstract presented at Second International Conference on Antisense Nucleic Acids, Garmisch–Partenkirchen, Germany, Feb. 12–16, 1995.

Varma, Rajender S., "Synthesis of Oligonucleotide Analogues with Modified Backbones," *Synlett*, 1993:621–637 (1993).

Vidal–Gomez et al., "Aminoacid and Protein Conjugates with Biologically Active Purines," *Journal of Heterocyclic Chemistry*, 12:273–278 (1975).

Watkins et al., "Synthesis of Benzyl and Benzyloxycarbonyl Base–Blocked 2'–Deoxyribonucleosides," *J. Org. Chem.*, 47:4471–4477 (1982).

Akashi et al., "New Aspects of Polymer Drugs," *Adv. Polym. Sci.*, 97:107–146 (1990).

Brady et al., "Large–Scale Synthesis of a Cyclic Hexapeptide Analogue of Somatostatin," *J. Org. Chem.*, 52:764–769 (1987).

Brown et al., "NMR Solution Structure of a Peptide Nucleic Acid Complexed with RNA," *Science*, 265:777–780 (1994).

Buttrey et al., "The Resolution of DL–β–(Thymin–1–yl)alanine and Polymerisation of the β–(Thymin–1–yl)alanines," *Tetrahedron*, 31:73–75 (1975).

De Koning et al., "Unconventional Nucleotide Analogues V. Derivatives of 6–(1–pyrimidinyl)– and 6–(9–purinyl)–2–aminocaproic acid," *Recueil*, 90:874–884 (1971).

Demidov et al., "Stability of peptide nucleic acids in human serum and cellular extracts," *Biochemical Pharmacology*, 48:1310–1313 (1994).

Doel et al., "An Approach to the Synthesis of Peptide Analogues of Oligonucleotides (Nucleopeptides)," *Tetrahedron Letters*, 27:2285–2288 (1969).

Doel et al., "The Synthesis of Peptides Containing Purine and Pyrimidine Derivatives of DL–Alanine," *Tetrahedron*, 30:2755–2759 (1974).

Egholm et al., "Peptide Nucleic Acids containing Adenine or Guanine recognize Thymine and Cytosine in Complementary DNA Sequences," *J. Chem. Soc., Chem. Comm.*, 800–801 (1993).

Flam, F., "Can DNA Mimics Improve On the Real Thing?," *Science*, 262:1647–1649 (1993).

Frank–Kamenetskii, M., "A Change of Backbone," *Nature*, 354:505 (1991).

Griffith et al., "Single and Bis Peptide Nucleic Acids as Triplexing Agents:Binding and Stoichiometry," *J. Am. Chem. Soc.*, 117:831–832 (1995).

Hassine et al., "Syntheses Asymetriques et Syntheses Asymetriques Potentielles D'α–Amino Alcools: Hydroxyamination D'Olefines Par La Methode De Sharpless," *Bull. Soc. Chim. Belg.*, 94:759–767 (1985).

Huang et al., "Acyclic Nucleic Acid Analogues: Synthesis and Oligomerization of γ,4–Diamino–2–oxo–l(2H)–pyrimidinepentanoic Acid and δ,4–Diamino–2–oxo–l(2H)–pyrimidinehexanoic Acid", *J. Org. Chem.*, 56:6007–6018 (1991).

Hyrup et al., "Structure–Activity Studies of the Binding of Modified Peptide Nucleic Acids (PNAs) to DNA," *J. Am. Chem. Soc.*, 116:7964–7970 (1994).

Inaki et al., "Functionality and Applicability of Synthetic Nucleic Acid Analogs," in *Current Topics in Polymer Science*; Ottenbrite, Utracki, Inoue, eds., New York: Macmillan Pub. Co., pp. 80–100 (1987).

Inaki Y., "Synthetic Nucleic Acid Analogs," *Prog. Polym. Sci.*, 17:515–570, (1992).

Koole et al., "Synthesis of Phosphate–Methylated DNA Fragments Using 9–Fluroenylmethoxycarbonyl as Transient Base Protecting Group," *J. Org. Chem.*, 54:1657–1664 (1989).

Lagriffoul et al., "The Synthesis, Co–oligomerization and Hybridization of a Thymine—Thymine Heterodimer Containing PNA," *Bioorg. Med. Chem. Lett.*, 4(8):1081–1085 (1994).

Leijon et al., "Structural Characterization of a PNA–DNA Duplexes by NMR. Evidence for DNA in B–like Conformation," *Biochemistry*, 33(33):9820–9825 (1994).

Lu et al., "Synthesis of Polyesters Containing Nucleic Acid Base Derivatives as Pending Side Chains," *J. Polym. Sci.: Part A: Polymer Chemistry*, 24:525–536 (1986).

Matthews et al., "Analytical Strategies for the Use of DNA Probes," *Analytical Biochemistry*, 169:1–25 (1988).

Møllegaard et al., "Peptide Nucleic Acid–DNA strand displacment loops as artificial promoters," *Proc. Natl. Acad. Sci. USA*, 91:3892–3895 (1994).

Nagae et al., "Functional Monomers and Polymers. CLIV. Application of Nucleic Acid Base Containing Polymers to High Performance Liquid Chromatography," *J. Polym. Sci.: Part A: Polymer Chemistry*, 27:2593–2609 (1989).

Nielsen P.E., "Peptide Nucleic Acid (PNA): A Model Structure for the Primordial Genetic Material?," *Origins of Life and Evolution of the Biosphere*, 23:323–327 (1993).

Nielsen et al., "Peptide Nucleic Acids (PNAs): Potential anti–sense and anti–gene agents," *Anti–Cancer Drug Design*, 8:53–63 (1993).

Nielsen P.E., "Peptide Nucleic Acids (PNA): Potential Antiviral Agents," *Intl. Antiviral News*, 1:37–39 (1993).

Nielsen et al., "Peptide Nucleic Acids (PNA): Oligonucleotide Analogs with a Polyamide Backbone," *Antisense Research and Applications*, Crooke and B. Lebleu, eds., CRC Press, Boca Raton, FL, pp. 363–373 (1993).

Nielsen et al., "Sequence–specific transcription arrest by peptide nucleic acid bound to the DNA template strand," *Gene*, 149:139–145 (1994).

Nielsen et al., "Peptide Nucleic Acid (PNA). A DNA mimic with a Peptide Backbone," *Bioconjugate Chem.*, 5:3–7 (1994).

Nollet et al., "Unconventional Nucleotide Analogues –I. $N_9$–Purinyl α–Amino Acids," *Tetrahedron*, 25:5971–5981 (1969).

Nollet et al., "Unconventional Nucleotide Analogues –II. Synthesis of the Adenyl Analogue of Willardiine," *Tetrahedron*, 25:5983–5987 (1969).

Nollet et al., "Unconventional Nucleotide Analogues –III. 4–($N_1$–Pyrimidyl)–2–Aminobutyric Acids," *Tetrahedron*, 25:5989–5994 (1968).

Nollet et al., "Michael Addition of 4–O–Ethyluracil. A Method for Specific $N_1$–Alkylation of Hydroxypyrimidines," *Tetrahedron Letters*, 53:4605–4606 (1969).

Nyilas et al., "Arenesulfonylethoxycarbonyl—A Set of Amino Protecting Groups for DNA and RNA Synthesis," *Nucleosides and Nucleotides*, 7:787–793 (1988).

Párkányi et al., "Synthesis of Polymethylene Chain–Bridged 6–Substituted 8–Azapurines and Related Compounds," *Collect. Czech. Chem. Commun.*, 56:2382–2388 (1991).

Peffer et al., "Strand–invasion of duplex DNA by peptide nucleic acid oligomers," *Proc. Natl. Acad. Sci. USA*, 90:10648–10652 (1993).

Petersen, K.H., "PNA–DNA Chimeras," Ph.D. thesis for the Department of General and Organic Chemistry, University of Copenhagen, The H.C. Orsted Institute, pp. 1–74 and Appendix A and B, date on title page Mar., 1995.

Pitha et al, "Synthetic Analogs of Nucleic Acids", in *Biomedical Polymers*, Goldberg and Nakajima, eds., Academic Press, New York, pp. 271–297, (1980).

Pitha et al., "Inhibition of Murine Leukemia Virus Replication of Poly(vinyluracil) and Poly(vinyladenine)," *Proc. Natl. Acad. Sci. USA*, 70:1204–1208 (1973).

Pitha J., "Physiological Activities of Synthetic Analogs of Polynucleotides," *Advances in Polymer Science*, 50:1–16 (1983).

Rose, D. J., "Characterization of Antisense Binding Properties of Peptide Nucleic Acids by Capillary Gel Electrophoresis," *Anal. Chem.*, 65(24):3545–3549 (1993).

Simon et al., "Peptoids: A modular approach to drug discovery," *Proc. Natl. Acad. Sci. USA*, 89:9367–9371 (1992).

Sieber et al., "Selektive acidolytische Spaltung von Aralkyloxycarbonyl–Aminoschutzgruppen," *Helvetica Chimica Acta*, 51:614–622 (1968).

Takemoto et al., "Synthetic Nucleic Acid Analogs. Preparation and Interactions," *Advances in Polymer Science*, 41:1–51 (1981).

Takemoto, K., "Recent Problems Concerning Functional Monomers and Polymers Containing Nucleic Acid Bases," in *Polymeric Drugs*, Donaruma and Vogl, eds., Academic Press, New York, pp. 103–129 (1978).

Uhlmann et al., "Antisense Oligonucleotides: A New Therapeutic Principle," *Chemical Reviews*, 90(4):544–584 (1990).

Watkins et al., "Synthesis of Oligodeoxyribonucleotides Using N–Benzyloxycarbonyl–Blocked Nucleosides," *J. Am. Chem. Soc.*, 104:5702–5708 (1982).

Weller et al., "Molecular Modeling of Acyclic Polyamide Oligonucleotide Analogues," *J. Org. Chem.*, 56:6000–6006 (1991).

Wittung et al., "DNA–like Double Helix Formed by Peptide Nucleic Acid," *Nature*, 368:561–563 (1994).

Birkett et al., "Synthesis and Intramolecular Cyclisation of 5–Aminoimidazolealkanoates and Their Conversion to Purine Derivatives," *Synthesis*, 157–159 (1991).

Ege, "Organic Chemistry, Third Edition", pp. 114, 591, 592 (1994).

Christensen, *J. Peptide Sci.*, 3, 175 (1995).

Geiger et al., "The Peptides, vol. 3", Academic Press, 17–19 (1981).

Haslam, "Protection of Carboxyl Groups" in Protective Groups in Organic Chemistry, Plenum Press, Chapter 5, pp. 183, 185, 192 and 193. 1973.*

Barton, "Protection of NH Bonds and NR3" in Protective Groups in Organic Chemistry, Plenum Press, Chapter 2, pp. 43, 55 and 56–61. 1973.*

Geiger et al., "Amine Protecting Groups," Academic Press, pp. 1 and 17–19. 1981.*

* cited by examiner

SYNTHONS FOR THE SYNTHESIS AND DEPROTECTION OF PEPTIDE NUCLEIC ACIDS UNDER MILD CONDITIONS

This application is a continuation of application Ser. No. 08/487,666 filed on Jun. 7, 1995 now U.S. Pat. No. 6,133,444, which is a continuation-in-part application of PCT/US94/14742 filed on Dec. 22, 1994, which is a continuation-in-part of U.S. application Ser. No. 08/172,695 filed on Dec. 22, 1993, now abandoned.

BACKGROUND OF THE INVENTION

1. Field of the Invention

This invention relates to the field of Peptide Nucleic Acid (PNA) synthesis. More particularly, this invention relates to improved PNA synthons suitable for the synthesis and deprotection of PNAs under mild conditions.

2. Description of the Background Art

Peptide Nucleic Acids (PNAs) are synthetic polyamides which are promising candidates for the sequence-specific regulation of DNA expression and for the preparation of gene targeted drugs. See European Patent applications EP 92/01219 and 92/01220 which are herein incorporated by reference. PNAs are biopolymer hybrids which possess a peptide-like backbone to which the nucleobases of DNA are attached. Specifically, PNAs are synthetic polyamides comprised of repeating units of the amino acid, N-(2-aminoethyl)-glycine, to which the nucleobases adenine, cytosine, guanine, thymine and uracil are attached through a methylene carbonyl group. Unnatural nucleobases, such as pseudo isocytosine, 5-methyl cytosine and 2,6-diaminopurine, among many others, also can be incorporated in PNA synthons.

PNAs are most commonly synthesized from monomers (PNA synthons) protected according to the t-Boc/benzyl protection strategy, wherein the backbone amino group of the growing polymer is protected with the t-butyloxycarbonyl (t-Boc) group and the exocyclic amino groups of the nucleobases, if present, are protected with the benzyloxycarbonyl (benzyl) group. PNA synthons protected using the t-Boc/benzyl strategy are now commercially available but are inconvenient to use because, among other reasons, harsh acidic conditions are required to remove these protecting groups.

The t-Boc/benzyl protection strategy requires very strong acids to remove all of the benzyloxycarbonyl side chain nucleobase protecting groups. Typically, nucleic acid oligomers are exposed to hydrofluoric acid or trifluoromethane sulfonic acid for periods of time often exceeding one hour to completely remove the benzyl side chain protecting groups. This harsh acid treatment needed for final deprotection will often decompose, among other acid sensitive moieties, nucleic acids and carbohydrates which might be attached to the PNA oligomer. Furthermore, the use of hazardous acids such as hydrofluoric acid or trifluoromethane sulfonic acid is not commercially embraced in view of safety concerns for the operators and the corrosive effect on automation equipment and lines.

In addition, the t-Boc/benzyl protection strategy is not orthogonal but differential. A differential strategy is defined as a system of protecting groups wherein the protecting groups are removed by essentially the same type of reagent or condition, but rely on the different relative rates of reaction to remove one group over the other. For example, in the t-Boc/benzyl protecting strategy, both protecting groups are acid labile, with benzyloxycarbonyl groups requiring a stronger acid for efficient removal. When acid is used to completely remove the more acid labile t-Boc protecting groups, there is a potential that a percentage of benzyl groups will also be removed contemporaneously. Specifically, the t-Boc protecting group must be removed from the amino group backbone during each synthetic cycle so the next monomer can be attached to the backbone at the free amino site thereby allowing the polymeric chain to grow. The deprotection of the t-Boc amino protected backbone is accomplished using a strong acid such as trifluoroacetic acid. During this deprotection and subsequent construction of the PNA or nucleic acid oligomer, removal of the nucleobase side chain protecting groups, i.e., the benzyls, is undesirable. However, trifluoroacetic acid is potentially strong enough to prematurely deprotect a percentage of the side chain benzyl groups, thereby introducing the possibility of polymer branching and reducing the overall yield of desired product.

An orthogonal strategy, on the other hand, removes the protecting groups under mutually exclusive conditions, e.g., one group is removed with acid while the other group is removed with base. Christensen et al. have described orthogonal PNA synthons wherein the t-Boc amino backbone protecting group is removed in strong acid then reprotected with 9-fluorenylmethyloxycarbonyl (Fmoc), a base labile protecting group. Christensen, L. et al. "Innovation and Perspectives in Solid Phase Synthesis and Complementary Technologies-Biological and Biomedical Applications," 3rd SPS Oxford Symposia (1994). Although this protection strategy eliminates the potential for premature deprotection of the exocyclic amino group of the side chain nucleobase, extra steps are involved in preparation of this monomer. Additionally, strong acids such as hydrofluoric acid or trifluoromethane sulfonic acid still are required to remove the benzyl side chain protecting groups.

Another current limitation on the synthesis of PNA synthons is the formation of the side chain nucleobase protecting group. Generally, the exocyclic amino groups of the nucleobases, e.g., cytosine, adenine, and guanine, are protected as carbamates via reaction with activated carbonates or chloroformates. This method of carbamate formation suffers from the disadvantage that many chloroformates are unstable or that the chloroformates are not appreciably reactive with the mildly nucleophilic exocyclic amino groups of the nucleobases. Other methods of carbamate formation used for nucleobases include the use of imidazolides and alkyl imidazolium salts as acylating agents. See Watkins et al, J. Org. Chem., 1982, 47:4471–77 and Watkins et al., J. Am. Chem. Soc., 1982, 104, 5702–08. While imidazolides and alkylated imidazolides appear to overcome some of the difficulties associated with carbamate formation, their widespread use with nucleobases has yet to be reported. Recently, the 4-methoxy-triphenylmethyl (MMT) group was presented as another exocyclic amino protecting group for PNA synthon side chain nucleobases. Breipohl et al. 1st Australian Peptide Conference, Great Barrier Reef, Australia, Oct. 16–21, 1994.

In addition to the above, the synthesis of a selectively protected guanine PNA synthon has been elusive. The reported guanine PNA synthons are protected as benzyl ethers at the 6 carbonyl group but optionally possess benzyl protection of the exocyclic 2-amino group. See European Patent Application EP 92/01219 and Uunited States Patent Applications PCT/US92/10921. Given the relative reactivity of the 6 carbonyl group (enol form) and the more reactive exocyclic 2-amino group, there is no compelling reason for protecting the 6 carbonyl group during PNA synthesis, whereas protection of the more reactive 2-amino group is preferred.

The benzyloxycarbonyl group has been utilized in DNA synthesis for the protection of the exocyclic amino groups of the nucleobases cytosine, adenine and guanine. See Watkins et al, J. Org. Chem., 1982, 47, 4471–77 and Watkins et al., J. Am. Chem. Soc., 1982, 104, 5702–08. Nonetheless, the guanine synthon was difficult to prepare because the exocyclic 2-amino group of guanine was not reactive toward reagents routinely used to introduce the benzyl group, such as benzyl chloroformate, benzyloxycarbonyl imidazole and acyl imidazolium salts of benzyloxycarbonyl imidazole. Consequently, a non-conventional multi-step procedure was described wherein treatment with phenyl chlorothioformate simultaneously protected both the 6-carbonyl group and the exocyclic 2-amino group. Thereafter, the adduct was converted to a carbamate protected guanine compound whereby the 6-carbonyl protecting group was subsequently removed. Nonetheless, this indirect method is laborious because it requires the formation of a carbamate protecting group from the initial adduct and the subsequent deprotection of the 6-carbonyl group.

Suitably protected derivatives of 2-amino-6-chloropurine may be converted to guanine compounds by displacement of the 6-chloro group with oxygen nucleophiles. See Robins et al, J. Am. Chem. Soc. 1965, 87, 4934, Reese et al., Nucl. Acids Res., 1981, 9, 4611 and Hodge et al., J. Org. Chem., 1990, 56, 1553. Indeed, suitably protected derivatives of 2-amino-6-chloropurine are the starting materials currently described for preparation of the reported guanine PNA synthons. See European Patent Application EP 92/01219 and United States Patent Application PCT/US 92/10921.

The inventors of PNA describe a guanine synthon having no protection of the exocyclic 2-amino group but having the 6-carbonyl group protected as a benzyl ether. See European Patent Application EP 92/01219. This protection strategy is surprising because the more reactive 2-amino group will likely react (at least marginally) with the activated carboxylic acid group of other PNA monomers, thereby causing branching of the synthesized polymer. Conversely, the enol, which exists when the 6-carbonyl group remains unprotected, is not reactive enough to result in polymer branching and therefore should require no protection. This particular approach which is inconsistent with t-Boc/benzyl protection strategy they employed for the other PNA synthons.

In a more recent patent application, the guanine PNA synthon has both benzyl protection of the exocyclic 2-amino group and a 6 carbonyl group protected as a benzyl ether. See United States Patent Application PCT/US 92/10921. As previously discussed, there is no compelling rationale for protecting the 6 carbonyl group of the guanine PNA synthon. However, protection of the 6 carbonyl group enables selective ionization of the exocyclic 2-amino group of the guanine heterocycle thereby facilitating the reaction of the ionized 2-amino group with conventional benzyl protecting reagents (e.g. benzyloxycarbonyl imidazole). Nonetheless, protection of the exocyclic 2-amino group occurs on a guanine derivative additionally protected at the 6 carbonyl group of the nucleobase. Thus, the resulting synthon has both exocyclic 2-amino group and 6 carbonyl group protection. Hence, there remains no reported convenient high yield synthesis of a guanine PNA synthon having selective carbamate protection of the exocyclic 2-amino group, wherein the 6 carbonyl group remains unprotected.

Solid phase peptide synthesis methodology is applicable to the synthesis of PNA oligomers, but often requires the use of harsh conditions. In the above-mentioned t-Boc/benzyl protection scheme, the final deprotection of side-chains and release of the PNA molecule from the solid support is most often carried out by the use of strong acids such as anhydrous hydrofluoric acid (HF) (Sakakibara, et al., Bull. Chem. Soc. Jpn., 1965, 38, 4921), boron tris (trifluoroacetate) (Pless, et al., Helv. Chim. Acta, 1973, 46, 1609), and sulfonic acids such as trifluoromethanesulfonic acid and methanesulfonic acid (Yajima, et al., J. Chem. Soc., Chem. Comm., 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol. Thus, the sulfide-assisted acidolytic $S_N2$ deprotection method (Tam, et al., J. Am. Chem. Soc., 1983, 105, 6442 and J. Am. Chem. Soc., 1986, 108, 5242), the so-called "low," which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., J. Am. Chem. Soc., 1973, 95, 4501), and ammonolysis as well as hydrazinolysis (Bodanszky, et al., Chem., Ind., 1964, 1423), hydrogenolysis Jones, Tetrahedron Lett., 1977, 2853 and Schlatter, et al., Tetrahedron Lett., 1977, 2861)), and photolysis (Rich and Gurwara, J. Am. Chem. Soc., 1975, 97, 1575)).

Based on the recognition that most operations are identical in the synthetic cycles of solid-phase peptide synthesis (as is also the case for solid-phase PNA synthesis), a new matrix, PEPS, was recently introduced (Berg, et al., J. Am. Chem. Soc., 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously.

Two other methods proposed for the simultaneous synthesis of large numbers of peptides also apply to the preparation of multiple, different PNA molecules. The first of these methods (Geysen, et al., Proc. Natl. Acad. Sci. USA, 1984, 81, 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, Proc. Natl. Acad. Sci. USA, 1984, 82, 5131) utilizes a "tea bag" containing traditionally-used polymer beads. Other relevant proposals for multiple peptide or PNA synthesis include the simultaneous use of two different supports with different densities (Tregear, in "Chemistry and Biology of Peptides," J. Meienhofer, ed., Ann Arbor Sci., Publ., Ann Arbor, 1972, pp. 175–178), combining of reaction vessels via a manifold (Gordman, Anal. Biochem., 1984, 136, 397), multicolumn solid-phase synthesis (e.g. Krchnak, et al., Int. J. Peptide Protein Res., 1989, 33, 209), and Holm and Meldal, in "Proceedings of the 20th European Peptide Symposium," G. Jung and E. Bayer, eds., Walter de Gruyter & Co., Berlin, 1989, pp. 208–210), and the use of cellulose paper (Eichler, et al., Collect. Czech. Chem. Commun., 1989, 54, 1746).

While the conventional cross-linked styrene/divinylbenzene copolymer matrix and the PEPS supports are presently preferred in the context of solid-phase PNA synthesis, a nonlimiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl N'-acryloylhexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, Bioorg. Chem. 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.*, 1970, 4503); (3) a third general type of useful solid supports can be termed composites in that they contain two major ingredients: a resin and another material that is also substantially inert to the organic synthesis reaction conditions employed. A preferred support of this type is described in U.S. Pat. No. 5,235,028 which is herein incorporated by reference. One other exemplary composite (see Scott, et al., *J. Chrom. Sci.*, 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243) and van Rietschoten in "Peptides 1974," Y. Wolman, Ed., Wiley and Sons, New York, 1975, pp. 113–116); and (4) contiguous solid supports other than PEPS, such as cotton sheets (Lebl and Eichler, Peptide Res. 1989, 2, 232) and hydroxypropylacrylate-coated polypropylene membranes (Daniels, et al., Tetrahedron Lett., 1989, 4345), are suited for PNA synthesis as well.

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, *"Principles of Peptide Synthesis,"* Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., *Tetrahedron Lett.*, 1965, 2323) and polyethylene glycol (PEG) (Mutter and Bayer, *Angew. Chem., Int. Ed. Engl.*, 1974, 13, 88), is useful; (3) random polymerization (see, e.g., Odian, *"Principles of Polymerization,"* McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., *J. Am. Chem. Soc.*, 1965, 87, 4646), sometimes referred to as "inverse Merrifield synthesis" or "polymeric reagent synthesis," offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering), and one also can envision the development of "PNA ligases" for the condensation of a number of PNA fragments into very large PNA molecules; and (6) since antibodies can be gernated to virtually any molecule of interest, the recently developed catalytic antibodies (abzymes), discovered simultaneously by the groups of Lerner (Tramantano, et al., *Science,* 1986, 234, 1566) and of Schultz (Pollack, et al., *Science,* 1986, 234, 1570), also should be considered as potential candidates for assembling PNA molecules. There has been considerable success in producing abzymes catalyzing acyl-transfer reactions (see for example Shokat, et al., *Nature,* 1989, 338, 269 and references therein). Finally, completely artificial enzymes, very recently pioneered by Stewart's group (Hahn, et al., *Science,* 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty naturally occurring (proteinogenic) amino acids constituting peptides. In conclusion, no single strategy may be wholly suitable for the synthesis of a specific PNA molecule, and therefore, sometimes a combination of methods may work best.

SUMMARY OF THE INVENTION

Accordingly, it is an object of this invention to provide a convenient high yield synthetic pathway to novel PNA synthons having protecting groups capable of removal under mild conditions. Another object is to provide orthogonally protected PNA synthons for increased efficiency during PNA or nucleic acid oligomer synthesis. Still another object of this invention is to provide PNA synthons that are compatible with commercially available products and instrumentation, such as automated synthesizers.

This invention is a method for a convenient high yield synthesis of novel PNA synthons having protecting groups capable of removal under mild conditions. Generally, a PNA synthon is assembled by coupling a carbamate protected nucleobase side chain moiety with an amino protected backbone of the amino acid N-(2-aminoethyl)-glycine. Because the PNA synthons have protecting groups that are removed under mild conditions, they are highly desirable for use with commercially available instrumentation and products.

Additional features and advantages of the invention will be set forth in the description which follows, and, in part will be apparent from the description, drawings, and claims, or may be learned by practice of the invention.

By the method of this invention, a partially protected nucleobase compound having an exocyclic amino group, such as cytosine, adenine, guanine, uracil, pseudo isocytosine, 5-methyl cytosine, 2,6-diaminopurine and inosine, is reacted with an electrophilic carbonyl equivalent. The reaction produces an N-substituted intermediate compound which is believed to be an isocyanate. The N-substituted intermediate compound is not isolated, but is further reacted with an alcohol, thereby generating a fully protected nucleobase compound having a carbamate protected exocyclic amino group. The ability to react the N-substituted intermediate compound with various alcohols provides a versatile methodology for protecting the exocyclic amino group as a carbamate. Finally, the fully protected nucleobase compound is reacted with a metal alkoxide or metal hydroxide to hydrolyze an acetate ester side chain present in the starting material, the partially protected nucleobase compound. Hydrolysis produces the carbamate protected nucleobase side chain moiety with a free carboxylic acid group available for subsequent coupling to the amino backbone.

The PNA synthon is assembled by coupling the carbamate protected nucleobase side chain moiety to the amino protected backbone, either as the free carboxylic add or the protected ester. Preferably, the amino protected backbone is an amino protected backbone of N-(2-aminoethyl)-glycine. Consequently, the method yields novel PNA synthons with orthogonal protection of the exocyclic amino group of the nucleobase and the amino backbone group, e.g., acid labile carbamate protection of the exocyclic amino group of the nucleobase and base labile protection of the amino backbone group.

Subsequently, the PNA synthons having a free carboxylic acid functionality on the backbone are used to create PNAs, nucleic acid oligomers, and nucleic acid polymers, such as in combination with nucleotide and peptide monomers. Examples of nucleic acid oligomers include, but are not limited to, PNA, DNA and RNA sequences, and their various combinations. Because the chemistry of the PNA synthons is compatible with commercially available synthesizers, the synthons are readily transformed into polymeric chains of various lengths and sequences.

One aspect of this invention is a method for a convenient high yield synthesis of novel guanine PNA synthons having selective carbamate protection of the exocyclic 2-amino group. Generally, the guanine PNA synthon is assembled by coupling the selectively carbamate protected guanine side chain moiety to a suitably protected backbone ester of the amino acid, N-(2-aminoethyl)-glycine, followed by hydrolysis of the backbone ester group. Because only the exocyclic 2-amino group of the nucleobase is benzyl protected, the preferred guanine monomer of this invention is selectively protected and therefore completely consistent with the t-Boc/benzyl protection strategy currently employed for PNA synthesis.

By the method of this invention, partially protected 2-amino-6-halopurine compounds (e.g. compound I in FIGS. 1 and 2), which are alkylated at the N9 nitrogen atom with acetate ester moieties, are reacted with phosgene or phosgene equivalents (e.g., triphosgene or diphosgene) in the presence of a non-nucleophilic base. This step converts the relatively non-nucleophilic exocyclic 2-amino group of the purine to a reactive electrophilic 2-isocyanate group. The intermediary 2-isocyanato-6-halopurine is not isolated but is reacted with an alcohol thereby forming a fully protected 2-amino-6-chloropurine having a carbamate protected exocyclic 2-amino group (e.g.'s, compound II in FIG. 1 and compound VI in FIG. 2). Thus, applicants demonstrate a convenient high yield synthesis of a selectively protected compound which can be directly converted to a selectively carbamate protected guanine side chain moiety suitable for coupling to a suitably protected backbone ester of the amino acid N-(2-aminoethyl)-glycine.

Generally, the fully protected 2-amino-6-halopurine is converted to a carbamate protected guanine side chain moiety by simultaneously converting the 6-halo group to a 6 carbonyl group and hydrolyzing the N9 acetate ester group. Preferably, both transformations are accomplished in a single reaction by treatment with the alkoxide of 3-hydroxypropionitrile. Thus, the fully protected 2-amino-6-halopurine is treated with at least three equivalents of the alkoxide of 3-hydroxypropionitrile. Two equivalents of alkoxide are consumed to convert the 6-halo group to a 6 carbonyl group and at least one equivalent is consumed to hydrolyze the N9 acetate ester group thereby forming the desired selectively carbamate protected guanine side chain moiety (e.g.'s, compound III in FIG. 1 and compound VII in FIG. 2).

Thus, the components of the guanine PNA synthon are assembled by coupling the carbamate protected guanine side chain moiety to the suitably protected backbone ester. A suitably protected backbone ester is $N^1$-(tert-butyloxycarbonyl)-$N^4$-(2-aminoethyl)-glycine ethyl ester which is coupled to the carbamate protected guanine side chain moiety, thereby forming the guanine PNA synthon ester (e.g. compound IV). The synthesized guanine PNA synthon ester is then converted to a free carboxylic acid by hydrolyzing the backbone ester group. Consequently, the method yields a novel guanine PNA synthon having selective carbamate protection of the exocyclic 2-amino group wherein the 6 carbonyl group remains unprotected. With reference to FIG. 1, the guanine PNA synthon is compound V.

Preferably, the suitably protected backbone ester is $N^1$-(9-fluorenylmethyloxycarbonyl)-$N^4$-(2-aminoethyl)-glycine ethyl or methyl ester which is coupled to the carbamate protected guanine side chain moiety. Following hydrolysis of the backbone ester group, the novel guanine PNA synthon is realized. With reference to FIG. 2, an example of a PNA synthon formed with the preferred backbone is compound VIII.

Alternatively, the guanine PNA synthon can be assembled utilizing a suitably protected backbone in the form of a free carboxylic acid. The preferred suitably protected backbone is $N^1$-(9-fluorenylmethyloxycarbonyl)-$N^4$-(2-aminoethyl)-glycine which is coupled to the carbamate protected guanine side chain moiety. By this method, the guanine PNA synthon is created without requiring an additional hydroylsis step.

The invention is also directed to a fully protected 2-amino-6-halopurine compound of the general formula:

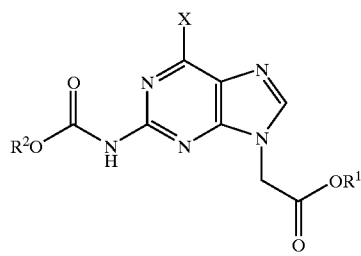

wherein

X is a halogen atom and is selected from the group consisting of fluorine (F), chlorine (Cl), bromine (Br) and iodine (I). The group represented by $R^1$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl and a benzyl group; wherein the benzyl group is a group of the formula:

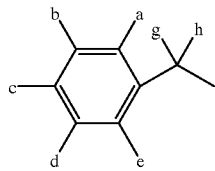

Each atom or group represented by each of a–e is independently selected from the group consisting of F, Cl, Br, I, hydrogen, methyl, ethyl, isopropyl, n-butyl, t-butyl, methoxy, ethoxy, —$NO_2$, —$SO_3H$, —CN, —$SCH_3$, —(O)$SCH_3$; and the atom or group represented by g and h is the same or different and is independently selected from the group consisting of hydrogen and methyl.

The group represented by $R^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a benzyl group as defined above and a diphenyl group having the formula:

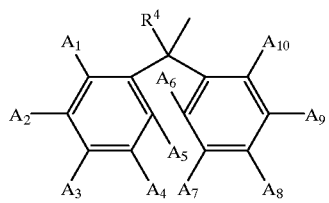

The atom or group represented by each of $A_1$–$A_{10}$ is independently selected from the group consisting of F, Cl, Br, I, hydrogen, methyl, ethyl, methoxy and ethoxy; and the atom or group represented by $R^4$ is selected from the group consisting of hydrogen, methyl and ethyl.

In another embodiment, $R^2$ can be a thioether group of the formula

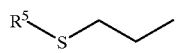

The group represented by $R^5$ is selected from the group consisting of methyl, ethyl, propyl, isopropyl, n-butyl, t-butyl and a phenyl group; wherein the phenyl group is a group of the formula:

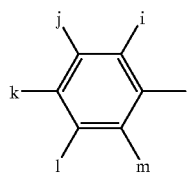

The atom or group represented by each of i–m is the same or different and is independently selected from the group consisting of F, Cl, Br, I, hydrogen, methyl, ethyl, isopropyl, t-butyl, phenyl, methoxy, ethoxy, —$NO_2$, —$SO_3H$, —CN, —$SCH_3$, and —(O)$SCH_3$.

In preferred embodiments, X is Cl, $R^1$ is a benzyl group wherein a–e and g–h all are hydrogen and $R^2$ is a thioether group wherein $R^5$ is methyl; and alternatively, X is Cl, $R^1$ is a benzyl group wherein a–e and g–h all are hydrogen and $R^2$ is a thioether group wherein $R^5$ is a phenyl group with each of i–m as hydrogen.

The invention is also directed to a fully protected 2-amino-6-halopurine of the formula:

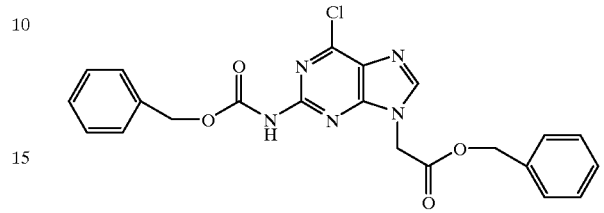

The most preferred embodiment of the invention is a fully protected 2-amino-6-halopurine having the formula:

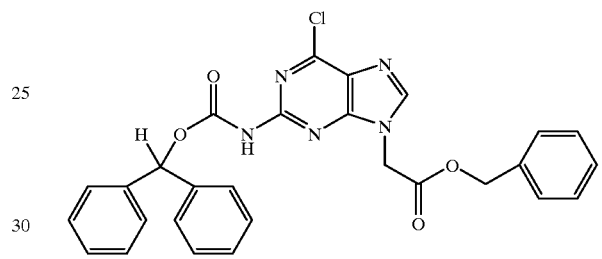

The invention is also directed to a selectively carbamate protected guanine side chain moiety of the general formula:

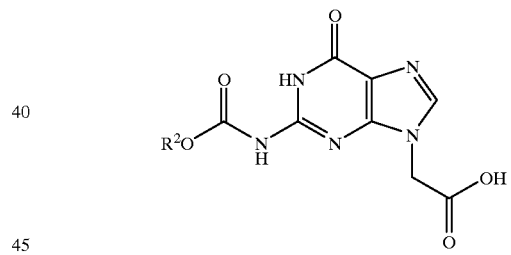

The group represented by $R^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a benzyl group as defined above and a diphenyl group having the formula:

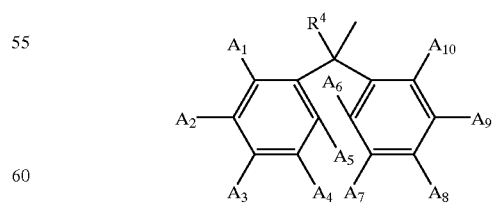

The atom or group represented by each of $A_1$–$A_{10}$ is independently selected from the group consisting of F, Cl, Br, I, hydrogen, methyl, ethyl, methoxy and ethoxy; and the atom or group represented by $R^4$ is selected from the group consisting of hydrogen, methyl and ethyl.

In another embodiment, $R^2$ can be thioether group of the formula:

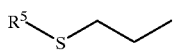

The group represented by $R^5$ is selected from the group consisting of methyl, ethyl, propyl, isopropyl, n-butyl, t-butyl and a phenyl group; wherein the phenyl group is a group of the formula:

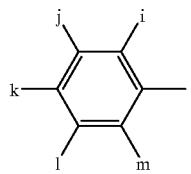

The atom or group represented by each of i–m is the same or different and is independently selected from the group consisting of F, Cl, Br, I, hydrogen, methyl, ethyl, isopropyl, t-butyl, phenyl, methoxy, ethoxy, —$NO_2$, —$SO_3H$, —CN, —$SCH_3$, and —(O)$SCH_3$.

Preferred embodiments of the compound occur when $R^2$ is a thioether group wherein $R^5$ is methyl, and when $R^2$ is a thioether group wherein $R^5$ is a phenyl group with each of i–m as hydrogen.

The invention is also directed to a selectively carbamate protected guanine side chain moiety having the formula:

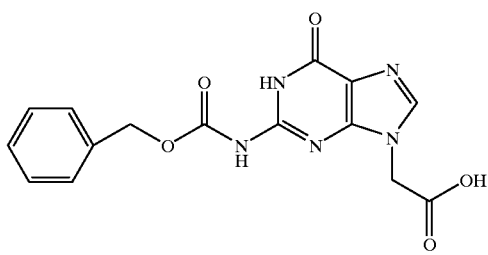

The invention is also directed to the selectively carbamate protected guanine side chain moiety having the formula:

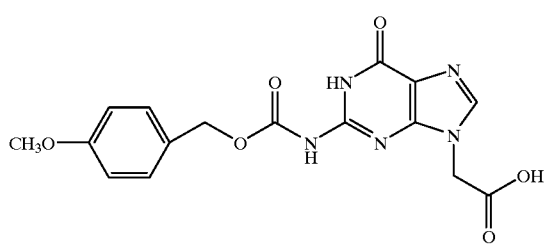

The most preferred embodiment of the invention is a selectively carbamate protected guanine side chain moiety having the formula:

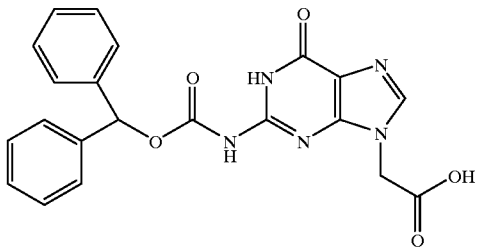

The invention is also directed to a guanine PNA synthon ester of the general formula:

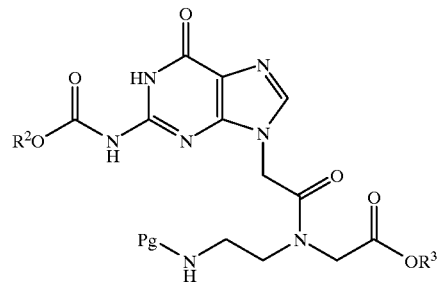

The group represented by Pg is a protecting group selected from the group consisting of alkyloxycarbonyl, 9-fluorenylmethyloxycarbonyl, 1-methyl-1-(4-biphenyl)-ethyloxycarbonyl, 1-methyl-1-phenyl-ethyloxy carbonyl, triphenylmethyl, 4-methoxy-triphenylmethyl, 4,4'-dimethoxy-triphenylmethyl, allyloxycarbonyl, methyl sulfonyl ethoxycarbonyl and phenyl sulfonyl ethoxycarbonyl.

The group represented by $R^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a benzyl group as defined above, a diphenyl group as defined above; and a thioether group as defined above. The group represented by $R^3$ is an alkyl group selected from the group consisting of methyl and ethyl.

The invention is also directed to a guanine PNA synthon ester having the formula:

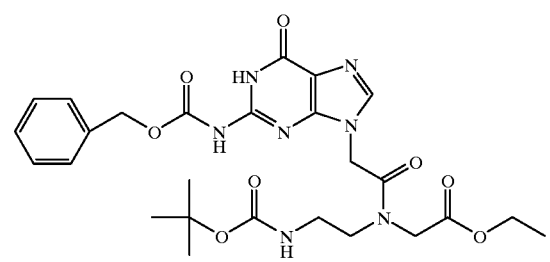

A preferred embodiment of the invention is a guanine PNA synthon ester having the formula:

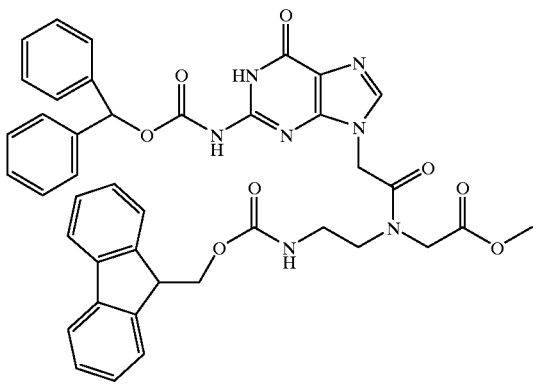

The invention is also directed to a guanine PNA synthon of the formula:

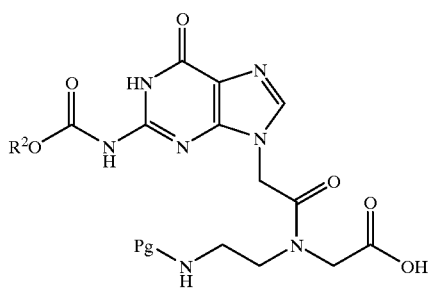

The group represented by Pg is a protecting group selected from the group consisting of alkyloxycarbonyl, 9-fluorenylmethyloxycarbonyl, 1-methyl-1-(4-biphenyl)-ethyloxycarbonyl, 1-methyl-1-phenyl-ethyloxycarbonyl, triphenylmethyl, 4-methoxy-triphenylmethyl, and 4,4'-dimethoxytriphenylmethyl.

The group represented by $R^2$ is selected from the group consisting of methyl, ethyl, 2,2,2-trichloroethyl, 2-(trimethylsilyl)-ethyl, propyl, isopropyl, n-butyl, t-butyl, ally, 1-isopropyl allyl, cinnamyl, and 4-nitrocinnamyl, a benzyl group as defined above, a diphenyl group as defined above, and a thioether group as defined above.

The invention is also directed to the guanine PNA synthon having the formula:

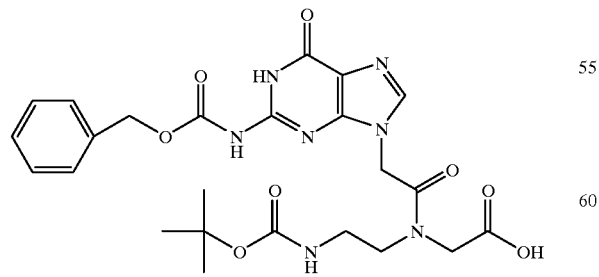

The invention is also directed to the guanine PNA synthon having the formula:

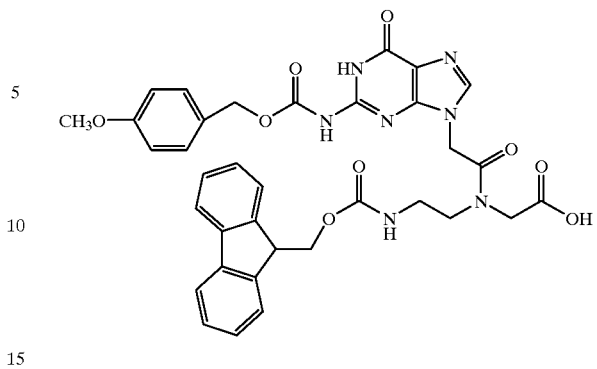

A preferred embodiment of the invention is a guanine PNA synthon having the formula:

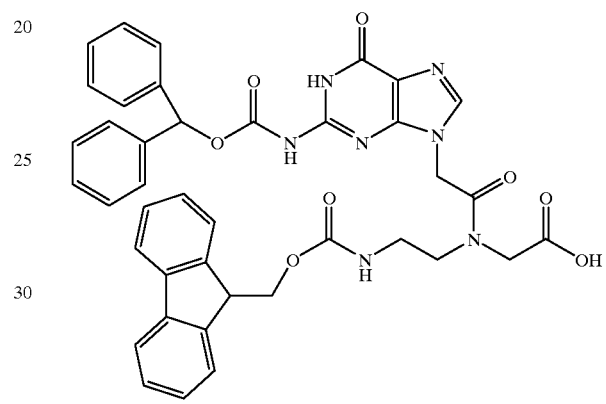

In another aspect, the invention is directed to fully protected nucleobase compounds (e.g.'s, compound X in FIG. 3 and compound XIV in FIG. 4) having the formulas:

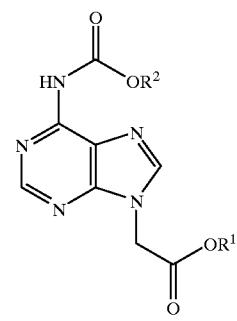

and

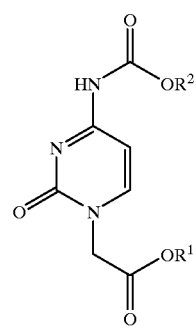

The group represented by $R^1$ is methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, or a substituted or unsubstituted benzyl of the formula:

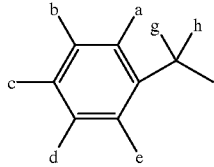

The atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, $NO_2$, $—SO_3H$, $—CN$, $—SCH_3$, and $—(O)SCH_3$. The atom or group represented by each of g–h is the same or different and is independently selected from the group consisting of hydrogen and methyl.

The group represented by $R^2$ is methyl, ethyl, 2,2,2-trichloroethyl, 2-(trimethylsilyl)-ethyl, 2-(phenylthio)-ethyl, propyl, isopropyl, n-butyl, t-butyl, allyl, 1-isopropyl allyl, cinnamyl, 4-nitrocinnamyl, a substituted or unsubstituted benzyl as set forth above, or a diphenyl group of the formula:

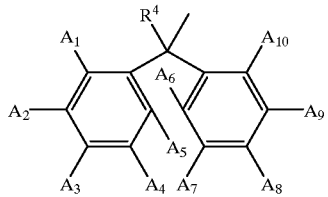

The atom or group represented by each of $A_1$–$A_{10}$ is independently selected from the group consisting of F, Cl, Br, I, hydrogen, methyl, ethyl, methoxy and ethoxy, and the atom or group represented by $R^4$ is hydrogen, methyl or ethyl;

The group represented by $R^2$ also can be a thioether group having the formula:

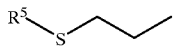

The group represented by $R^5$ is methyl, ethyl, propyl, isopropyl, n-butyl, t-butyl or a phenyl group, wherein the phenyl group has the formula:

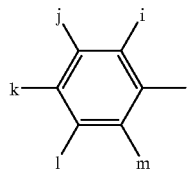

The atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, $NO_2$, $—SO_3H$, $—CN$, $—SCH_3$, and $—(O)SCH_3$.

In another embodiment, $R^2$ can be an ethyl group having the formula:

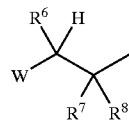

The group represented by W is an electron withdrawing group and the atom or group represented by each of $R^6$–$R^8$ is the same or different and is independently selected from the group consisting of hydrogen, methyl, ethyl, n-propyl, isopropyl, n-butyl and t-butyl. Preferred electron withdrawing groups include, but are not limited to, cyano, alkyl sulfonyl, aryl sulfonyl, phenyl and substituted phenyl, such as p-nitrophenyl, o-nitrophenyl and p-alkyl sulfonyl phenyl.

In preferred embodiments of the compounds, $R^1$ is a methyl group and $R^2$ is a diphenyl group wherein each of $A_1$–$A_{10}$ and $R^4$ is hydrogen; and, alternatively $R^1$ is an ethyl group and $R^2$ is a diphenyl group wherein each of $A_1$–$A_{10}$ and $R^4$ is hydrogen. Other preferred embodiments occur when $R^2$ is an ethoxycarbonyl group where W is a cyano group, $R^6$ is a hydrogen atom and each of $R^7$ and $R^8$ is a methyl group.

In another aspect, this invention is directed to carbamate protected nucleobase side chain moieties (e.g.'s, compound XI in FIG. 3 and compound XV in FIG. 4) having the formulas:

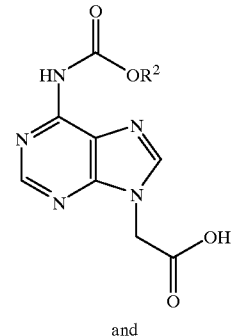

and

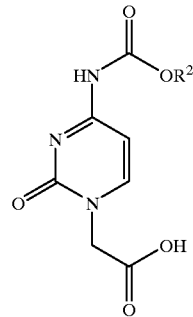

wherein $R^2$ is as defined above.

Preferred embodiments of the compounds occur when $R^2$ is a diphenyl group wherein each of $A_1$–$A_{10}$ and $R^4$ is hydrogen; and when $R^2$ is an ethyl group where W is a cyano group, $R^6$ is a hydrogen atom and each of $R^7$ and $R^8$ is a methyl group.

In another aspect, this invention is directed to PNA synthons (e.g.'s, compound XII in FIG. 3 and compound XVI in FIG. 4) having the formulas:

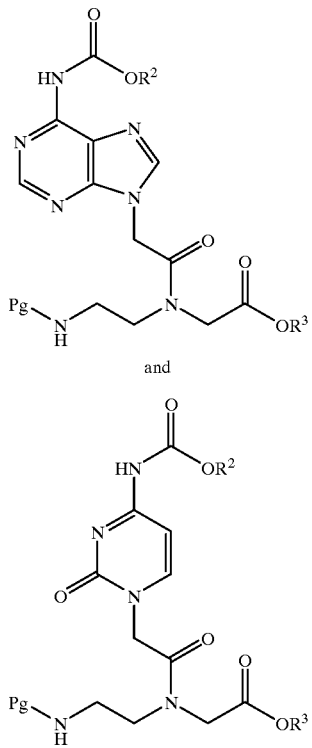

The group represented by Pg is a protecting group selected from the group consisting of alkyloxycarbonyl, 9-fluorenylmethyloxycarbonyl, 1-methyl-1-(4-biphenyl)-ethyloxycarbonyl, 1-methyl-1-phenyl-ethyloxycarbonyl, triphenylmethyl, 4-methoxy-triphenylmethyl, 4,4'-dimethoxy-triphenylmethyl, allyloxycarbonyl, methyl sulfonyl ethoxycarbonyl and phenyl sulfonyl ethoxycarbonyl. The group represented by $R^2$ is as previously described. The atom or group represented by $R^3$ is hydrogen or an alkyl group such as methyl or ethyl.

Preferred embodiments of the compounds occur when Pg is 9-fluorenylmethyloxycarbonyl, $R^2$ is a diphenyl group wherein each of $A_1$–$A_{10}$ and $R^4$ is hydrogen and $R^3$ is hydrogen; and when Pg is 9-fluorenylmethyloxycarbonyl, $R^2$ is a diphenyl group wherein each of $A_1$–$A_{10}$ and $R^4$ is hydrogen and $R^3$ is ethyl. These preferred embodiments are examples of orthogonally protected PNA synthons.

It is to be understood that both the foregoing general description and the following detailed description are exemplary and explanatory and are intended to provide further explanation of the invention as claimed. The invention will be understood further from the following drawings, which are incorporated in and constitute a part of this specification.

DETAILED DESCRIPTION OF THE INVENTION

The applicant has developed a convenient high yield method for preparing novel N-substituted nucleobase intermediates having carbamate protection of the exocyclic amino functional group of the heterocycle which are suitable for preparation of novel PNA synthons. Generally, the PNA synthons are assembled by coupling the carbamate protected nucleobase side chain moiety to an amino protected backbone of the amino acid N-(2-aminoethyl)-glycine. Thus, the PNA synthons of the invention are prepared with a nucleobase side chain moiety containing carbamate protection capable of removal under mild conditions. Natural or unnatural nucleobases can be incorporated into the PNA synthons. In addition, the PNA synthons of the invention can have orthogonal protection of the carbamate protected nucleobase and the amino protected backbone. Furthermore, there is no report of a guanine PNA synthon having selective carbamate protection of the exocyclic 2-amino group, wherein the 6 carbonyl group remains unprotected.

Guanine PNA Synthon Synthesis

Figure 1:
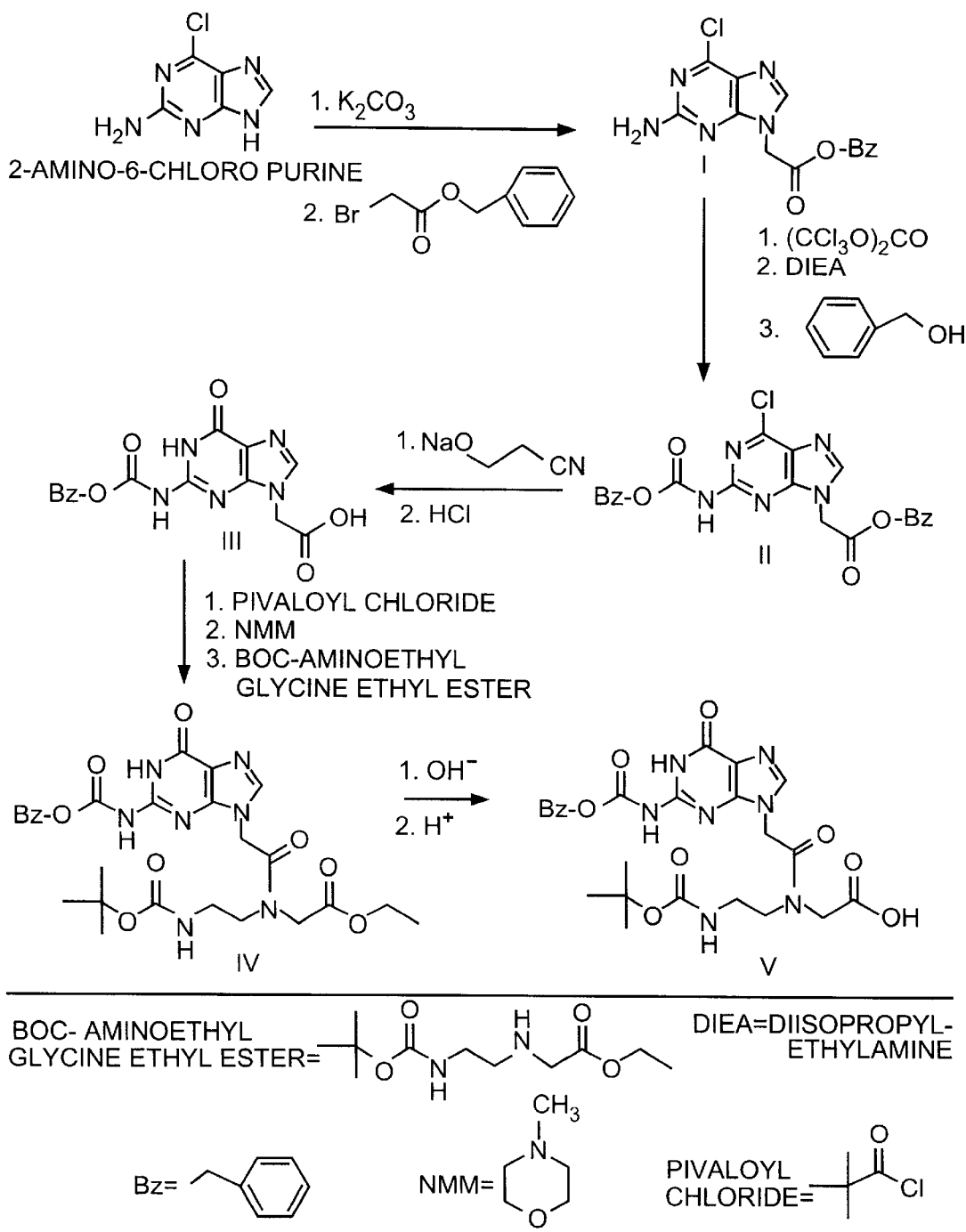
FIG. 1 is a schematic representation of the synthesis of a guanine PNA synthon of this invention.
Figure 2:
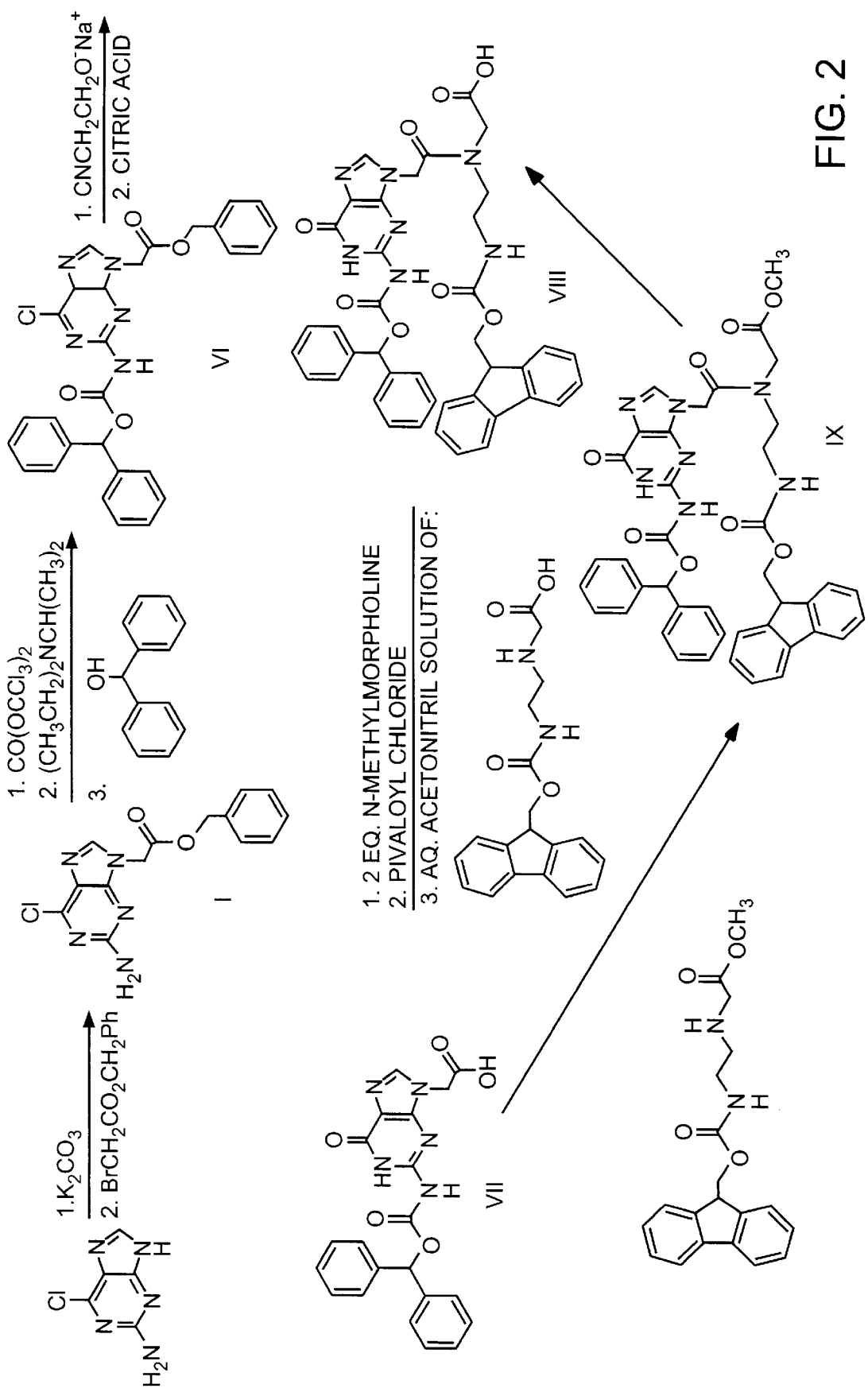
FIG. 2 is a schematic representation of the synthesis of the preferred guanine PNA synthon of this invention.

In one embodiment, the invention is a method for the preparation of a guanine PNA synthon (see FIGS. 1 and 2).

Step 1

With reference to FIG. 1, this invention encompasses a method for preparing guanine PNA synthons having selective carbamate protection of the exocyclic 2-amino group. The starting material for preparation of the carbamate protected guanine side chain moiety is a 2-amino-6-halopurine. Preferably, the 2-amino-6-halopurine is 2-amino-6-chloropurine. The 2-amino-6-halopurine is first alkylated at the N9 nitrogen atom of the purine ring with a protecting moiety thereby forming a partially protected 2-amino-6-halopurine. "Partially protected" is defined as protecting a heterocyclic N-atom with a side chain group which will form the linkage between the amino protected backbone and the carbamate protected nucleobase while leaving an exocyclic amino group unprotected. The preferred side chain group is an acetate ester moiety. "Fully protected" is defined as protecting all nucleophilic atoms or functional groups which react with electrophilic carbonyl equivalents. For example, a fully protected guanine compound is rendered inert to phosgene or any phosgene equivalent.

Thus, in one embodiment, the partially protected 2-amino-6-halopurine compounds of this invention have the general formula:

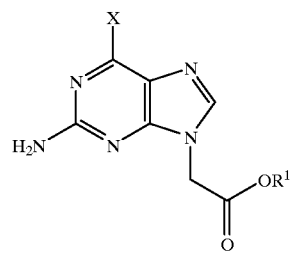

The atom represented by X is a halogen atom selected from the group consisting of F, Cl, Br and I. The alkyl group represented by $R^1$ is selected from the group consisting of methyl, ethyl, 2,2,2-trichloroethyl, 2-(trimethylsilyl)-ethyl, 2(phenylthio)-ethyl, propyl, isopropyl, n-butyl, t-butyl, allyl, 1-isopropyl allyl, cinnamyl, 4-nitrocinnamyl and a benzyl group of the general formula:

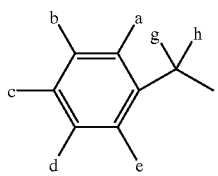

The atom or group represented by each a–e is the same or different and is independently selected from the group comprising F, Cl, Br, I, hydrogen, methyl, ethyl, isopropyl, t-butyl, phenyl, methoxy, ethoxy, —$NO_2$, —$SO_3H$, —CN, —$SCH_3$, and —(O)$SCH_3$. The atom or group represented by g–h is the same or different and is independently selected from the group consisting of hydrogen and methyl. With reference to FIG. 1, the most preferred partially protected 2-amino-6-halopurine has the formula:

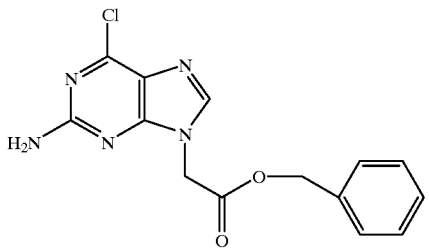

I

Step 2

Compounds II and VI are examples of fully protected 2-amino-6-halopurines. With reference to FIG. 1, compound I is treated sequentially with triphosgene, diisopropylethylamine (DIEA) and benzyl alcohol. The result is a fully protected 2-amino-6-halopurine (compound II). In a preferred embodiment of the invention, compound I is treated sequentially with triphosgene, diisopropylethylamine (DIEA) and benzhydrol (FIG. 2). The result is the fully protected 2-amino-halopurine represented by compound VI. Conversion of the partially protected 2-amino-6-halopurines to fully protected 2-amino-6-halopurines enables the carbamate protection at a fairly non-nucleophilic exocyclic 2-amino group. Thus, by the method of this invention, a partially protected 2-amino-6-halopurine compound is reacted with at least one (1) molar equivalent of phosgene in the presence of at least two (2) molar equivalents of a non-nucleophilic base thereby generating a 2-isocyanato-6-halopurine compound. Some examples of suitable non-nucleophilic bases are triethylamine, diisopropylethylamine, N-methyl morpholine and N-ethyl morpholine. Preferably the non-nucleophilic base is diisopropylethylamine. The reaction is typically performed in a non-nucleophilic anhydrous solvent which at least partially dissolves the non-nucleophilic base and the partially protected 2-amino-6-halopurine compound. Some examples of suitable solvents are diethyl ether, diisopropylether, dioxane, tetrahydrofuran, acetonitrile, ethyl acetate, dichloromethane, chloroform, carbon tetrachloride, benzene and toluene. Preferably, the solvent is tetrahydrofuran.

Phosgene is a highly toxic gas of chemical formula $COCl_2$. Because of the inherent dangers associated with handling and accurately dispensing phosgene gas, several phosgene equivalents are available. These include the liquid diphosgene and the solid triphosgene. These equivalents decompose, in situ, to generate two and three equivalents of phosgene, respectively, but are more easily handled and dispensed than is the gaseous equivalent. Consequently, all these reagents are non-limiting examples of phosgene equivalents suitable for the method of this invention.

Preferably, the intermediate 2-isocyanato-6-halopurine compound is not isolated because it is easily hydrolyzed back to the starting partially protected 2-amino-6-halopurine compound during the handling steps required for isolation. Therefore, the 2-isocyanate group of the intermediary 2-isocyanato-6-halopurine compound is then reacted with an alcohol thereby generating a novel fully protected 2-amino-6-halopurine compound having an exocyclic 2-amino group protected as a carbamate.

Though it is known that an alcohol reacts with an isocyanate to form a carbamate, this chemistry has yet to be applied to synthesis of carbamate protected aminopurines. This is probably because phosgene (or another phosgene equivalent) is a highly reactive electrophile. Moreover, the N7 nitrogen atom of the purine ring is fairly nucleophilic. Consequently, significant reaction of phosgene is expected to occur at the N7 nitrogen atom as well as at the exocyclic 2-amino group. Indeed, the applicants have determined that 6-amino-N9-ethylcarboxymethyl-purine (N9-ethylcarboxymethyl adenine) cannot be converted to the carbamate protected adenine derivative, presumably because phosgene reacts preferentially at the N7 nitrogen atom. However, the nucleophilicity of the N7 nitrogen atom is dependent upon the substitutents of the purine ring. Thus, applicants have surprisingly observed that the N7 nitrogen of 2-amino-6-chloro-N9-alkylated purine compounds do not appreciably react with phosgene thereby enabling the preparation of the novel fully protected 2-amino-6-halopurine compounds having selective carbamate protection of the exocyclic 2-amino group. These fully protected 2-amino-6-halopurine compounds are suitable for preparing carbamate protected guanine side chain moieties suitable for guanine PNA monomer synthesis.

Suitable alcohols which will react with the exocyclic 2-isocyanato group include, but are not limited to, methanol, ethanol, 2,2,2-trichloroethanol, 2-(trimethylsilyl)-ethanol, propanol, isopropanol, n-butanol, and t-butanol. Additionally, the alcohol may be an allyl alcohol derivative. The allyl alcohol derivative may be selected from the group consisting of allyl alcohol, 1-isopropylallyl alcohol, cinnamyl alcohol, and 4-nitrocinnamyl alcohol. The alcohol also can be a substituted or unsubstituted benzyl alcohol of the general formula:

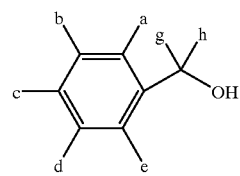

The atom or group represented by each a–e is the same or different and is independently selected from the group consisting of F, Cl, Br, I, hydrogen, methyl, ethyl, isopropyl, t-butyl, phenyl, methoxy, ethoxy, —$NO_2$, —$SO_3H$, —CN, —$SCH_3$, and —(O)$SCH_3$. The atom or group represented by each of g–h is the same or different and is independently selected from the group consisting of hydrogen and methyl.

The preferred alcohol is a diphenyl group having the formula:

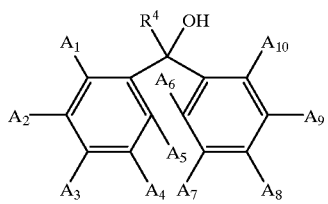

The atom or group represented by each of $A_1$–$A_{10}$ is independently selected from the group consisting of F, Cl, Br, I, hydrogen, methyl, ethyl, methoxy and ethoxy and the atom or group represented by $R^4$ is selected from the group consisting of hydrogen, methyl and ethyl.

The alcohol also may be a thioether group having the formula:

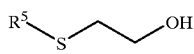

The group represented by $R^5$ is selected from the group consisting of methyl, ethyl, propyl, isopropyl, n-butyl, t-butyl and a phenyl group, wherein the phenyl group is a group of the formula:

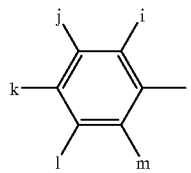

The atom or group represented by each i–m is the same or different and is independently selected from the group consisting of F, Cl, Br, I, hydrogen, methyl, ethyl, isopropyl, t-butyl, phenyl, methoxy, ethoxy, —NO$_2$, —SO$_3$, —CN, —SCH$_3$, and —(O)SCH$_3$.

In addition, the alcohol can be an ethyl group having the formula:

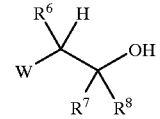

The group represented by W is an electron withdrawing group and the atom or group represented by each of $R^6$–$R^8$ is the same or different and is independently selected from the group consisting of hydrogen, methyl, ethyl, n-propyl, isopropyl, n-butyl and t-butyl.

Thus, the fully protected 2-amino-6-halopurine is a compound of the general formula:

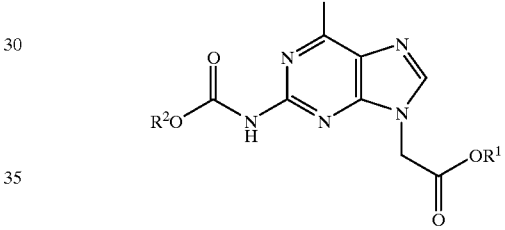

wherein $R^1$ and $R^2$ are as defined above. With reference to FIG. 1, the fully protected 2-amino-6-halopurine has the formula:

II

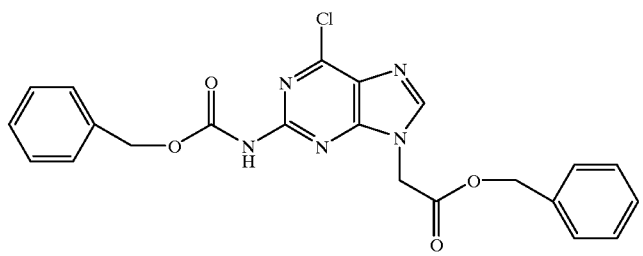

With reference to FIG. 2, the preferred fully protected 2-amino-6-halopurine is a compound of the formula:

VI

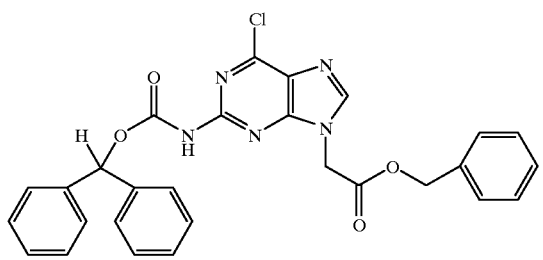

The versatility of this synthetic step is demonstrated by examples of several different fully protected 2-amino-6 chloropurine compounds prepared by simple substitution of a desired alcohol. Thus, Table I summarizes the yield results for several prepared 2-amino-6-chloropurine compounds wherein only the group $R^2$ differs. As the table suggests, the yields are moderate and fairly consistent regardless of the composition of the alcohol.

TABLE 1

Derivatives of Fully Protected 2-amino-6-chloro purine and Carbamate Protected Guanines

| $R^2$ | Compound Number | Percent Yield |
|---|---|---|
| (benzyl) | IIa | 70 |
|  | IIIa | 94 |
| (t-butyl-benzyl) | IIb | 45 |
|  | IIIb | 86 |
| (isopropyl-benzyl) | IIc | 51 |
|  | IIIc | 84 |
| (methoxy-benzyl) | IId | 55 |
|  | IIId | 82 |
| (diphenylmethyl) | IIe | 54 |
|  | IIIe | 62 |
| (methylthioethyl) | IIf | 74 |
|  | IIIf | 83 |
| (phenylthioethyl) | IIg | 62 |
|  | IIIg | 80 |

Step 3

It is known that suitably protected 2-amino-6-halopurine compounds may be converted to protected guanine compounds by several methods involving attack of the 6-halo group with oxygen nucleophiles. See Hodge, et al., Org. Chem. (1990) 56:1553–64. However, this invention discloses a method for converting the 6-halo group to a 6 carbonyl group, and simultaneously hydrolyzing the $N^9$ acetate ester group. Thus, carbamate protected guanine side chain moieties are prepared from the fully protected 2-amino-6-halopurine compounds by a method comprising the steps of converting the 6-halo group to a 6 carbonyl group and concurrently hydrolyzing the $N^9$ acetate ester group.

Remarkably, the alkoxide of 3-hydroxypropionitrile can both convert a 6-halo group to a 6 carbonyl group, and hydrolyze the $N^9$ acetate ester group. Thus the carbamate protected guanine side chain moiety is easily generated directly from the fully protected 2-amino-6-halopurine in a single reaction. With reference to the embodiment depicted in FIG. 1, 2-(N-[benzyloxycarbonyl])-amino-6chloro-$N^9$-(benzylcarboxymethyl)-purine (compound II) is directly converted to 2-(N-benzyloxycarbonyl])-$N^9$-(carboxymethyl)-guanine (compound III). According to the method, at least three equivalents of the alkoxide of 3-hydroxypropionitrile is reacted with compound II. Two equivalents are used to convert the 6-halo group to a 6 carbonyl group and at least one equivalent is simultaneously used to hydrolyze the $N^9$ acetate ester group. Consequently, the preferred carbamate protected guanine side chain moiety, compound III, is prepared in high yield.

The preferred embodiment depicted in FIG. 2 shows the conversion of 2-(N-[benzhydroloxycarbonyl])-amino-6-chloro-$N^9$(benzylcarboxymethyl)-purine (compound VI) into 2-(N-[benzhydroloxycarbonyl])-$N^9$-(carboxymethyl)-guanine (compound VII) using the same synthetic procedure.

According to the method of the invention, at least three (3) equivalents of the alkoxide of 3-hydroxypropionitrile are prepared per equivalent of fully protected 2-amino-6-halopurine by the treatment of 3-hydroxypropionitrile with metal hydride in a non-nucleophilic anhydrous solvent. The metal hydrides that may be used include, but are not limited to, lithium hydride, sodium hydride, potassium hydride and cesium hydride. Examples of suitable non-nucleophilic solvents have been previously described. Preferably, the metal hydride is sodium hydride and the solvent is tetrahydrofuran.

The fully protected 2-amino-6-halopurine compound is added to the prepared solution of alkoxide. The mechanism of this step of the reaction, although not necessary to an understanding of the invention, is believed to be as follows. Initially, one equivalent of alkoxide displaces the 6-halo atom thereby forming a 6-cyanoethoxy ether. Thereafter, abstraction of a proton from the 2-cyanoethyl ether group by another equivalent of alkoxide will cause β-elimination thereby forming a 6 carbonyl group, one equivalent of acrylonitrile and one equivalent of 3-hydroxypropionitrile. Thus, two equivalents of alkoxide of 3-hydroxypropionitrile are consumed to convert the 6-halo group to a 6 carbonyl group.

Simultaneous hydrolysis of the $N^9$ acetate ester group of the fully protected 2-amino-6-halopurine also comprises reaction with the alkoxide of 3-hydroxypropionitrile. According to the method, one equivalent of the alkoxide of 3-hydroxypropionitrile will react with the $N^9$ acetate ester group causing displacement of the original alcohol and thereby forming a 2-cyanoethyl ester and the metal alkoxide of the displaced alcohol. Thereafter, abstraction of a proton from the 2-cyanoethyl ester group by an additional equivalent of alkoxide will cause β-elimination thereby forming the metal salt of the backbone carboxylic acid group, one equivalent of acrylonitrile and one equivalent of alcohol.

The alkoxide used to abstract the proton from the cyanoethyl ester may be the alkoxide of the displaced alcohol or a molecule of the alkoxide of 3-hydroxypropionitrile where an excess of the alkoxide of 3-hydroxypropionitrile is used. Thus, only one equivalent of the alkoxide of 3-hydroxypropionitrile is required to hydrolyze the $N^9$ acetate ester group. Preferably, an excess of the alkoxide of 3-hydroxypropionitrile is prepared.

Thus, the products of reacting the fully protected 2-amino-6-halopurine with three (3) equivalents of alkoxide are: the metal salt of the selectively carbamate protected guanine side chain moiety; two equivalents of acrylonitrile; one equivalent of 3-hydroxypropionitrile; and one equivalent of alcohol which may or may not be 3-hydroxypropionitrile. Thereafter, the metal salt of the selectively carbamate protected guanine side chain moiety is neutralized by treating with at least two equivalents of acid. Neutralization involves protonation of both the N1 nitrogen of the purine heterocycle and protonation of the metal salt of the backbone carboxylic acid group. The acid may be organic or inorganic and should preferably have a pKa of less than about two (2) thereby enabling the protonation of both the N1 nitrogen of the purine heterocycle and the backbone carboxylic acid group.

In one embodiment, the carbamate protected guanine side chain moiety is a compound of the formula:

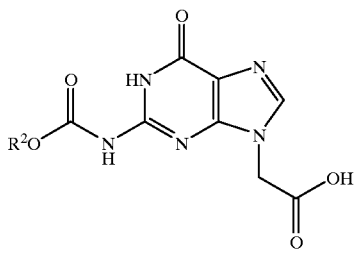

wherein $R^2$ is as defined above. With reference to FIG. 1, the carbamate protected guanine side chain moiety has the formula:

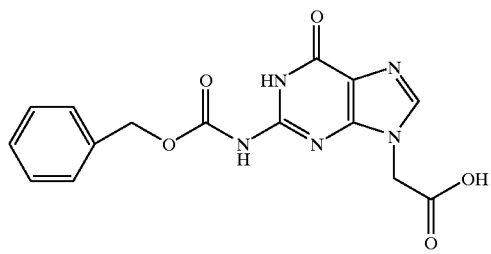

III

Another selectively carbamate protected guanine side chain moiety has the formula:

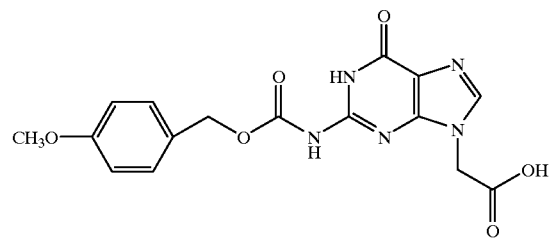

Another selectively carbamate protected guanine side chain moiety has the formula:

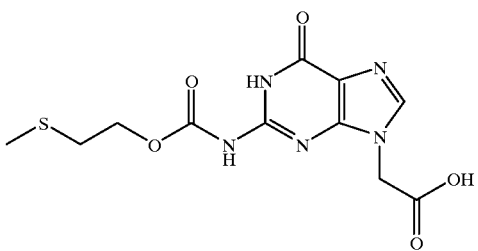

Another selectively carbamate protected guanine side chain moiety has the formula:

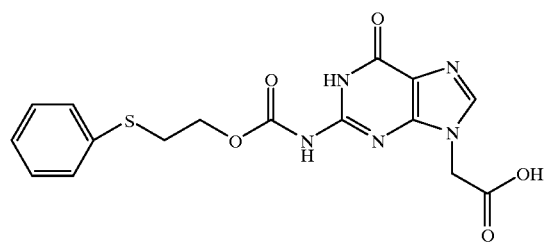

The preferred selectively carbamate protected guanine side chain moiety has the formula:

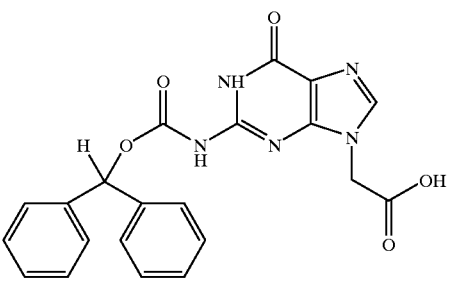

VII

The versatility of this synthetic step is demonstrated by preparation of several different selectively carbamate protected guanine side chain moieties. Thus, Table I summarizes the yield results for several prepared selectively carbamate protected guanine side chain moieties wherein only the alkyl group $R^2$ differs. As the table suggests, the yields are excellent and do not substantially differ with the composition of the alkyl group $R^2$.

With reference to FIG. 1 or FIG. 2, the final steps in preparing the guanine PNA synthon involve coupling the carbamate protected guanine side chain moiety (compounds III or VII) to a suitably protected backbone ester of the amino acid N-(2-aminoethyl)-glycine, followed by hydrolysis of the backbone ester group. These steps generate first the guanine PNA synthon ester (e.g. compound IV), and second, the guanine PNA synthon (e.g. compound V). Alternatively, as seen in FIG. 2, the guanine PNA synthon can be prepared by coupling the carbamate protected guanine side chain moiety (compound VII) to a suitably protected amino backbone having a free carboxylic acid group. Coupling performed by this method directly produces the guanine PNA synthon (compound VIII) without the additional hydrolysis step.

Step 4

Coupling of the selectively carbamate protected guanine side chain moiety (e.g.'s, compounds III and VII) to the suitably protected backbone ester of the amino acid N-(2-aminoethyl)-glycine, comprises the steps of: first generating the mixed anhydride of the carboxylic acid functional group of the carbamate protected guanine side chain moiety by treatment with a non-nucleophilic base in the presence of a sterically hindered acid chloride, and secondly reacting the prepared mixed anhydride with a suitably protected backbone ester of the amino acid N-(2-aminoethyl)-glycine, thereby generating the guanine PNA synthon ester.

The non-nucleophilic base used to generate the mixed anhydride of the selective carbamate protected guanine side chain moiety can be any of the non-nucleophilic bases previously described. Preferably, the base is N-methyl morpholine. The sterically hindered acid chloride is preferably selected from the group consisting of isobutyryl chloride, trimethylacetyl chloride (pivaloyl chloride) and adamantane carboxyl chloride. The most preferred acid chloride is trimethylacetyl chloride (pivaloyl chloride).

The suitably protected backbone ester of the amino acid N-(2-aminoethyl)-glycine, will have the general formula:

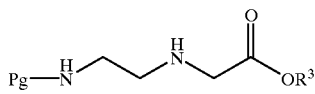

The protecting group represented by Pg is a protecting group which may be selected from the group consisting of alkyloxycarbonyl, 9-fluorenylmethyloxycarbonyl, methyl-1-(4-biphenyl)-ethyloxycarbonyl, 1-methyl-1-phenyl-ethyloxy carbonyl, triphenylmethyl, 4-methoxy-triphenylmethyl, and 4,4'-dimethoxy-triphenylmethyl. The alkyl group represented by $R^3$ may be selected from the group consisting of methyl and ethyl. With reference to FIG. 1, the protecting group (Pg) is tert-butyloxycarbonyl (t-Boc) and the alkyl group ($R^3$) is ethyl. Therefore, the guanine PNA synthon ester has the formula:

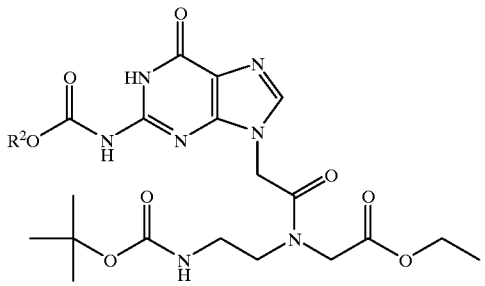

wherein $R^2$ is as defined above.

In another embodiment, the guanine PNA synthon ester has the formula:

IV

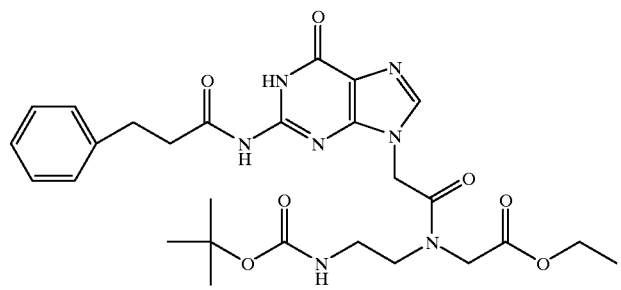

Alternatively, the amino protected backbone of the amino acid N-(2-aminoethyl)-glycine can have the formula:

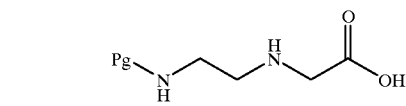

The group represented by Pg is as defined above. The preferred backbone protecting group (Pg) is 9-fluorenylmethyloxycarbonyl (Fmoc). Thus, the preferred amino protected backbone has the formula:

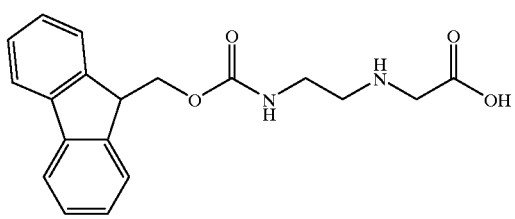

The Fmoc protecting group is a well known base labile protecting group used in peptide synthesis. By the method of this invention, since the exocyclic amino group of guanine is protected as an acid labile carbamate, coupling the preferred Fmoc amino protected backbone to the guanine side chain moiety results in an orthogonally protected guanine PNA synthon. Orthogonal is defined as a system of protecting groups wherein each independent class of protecting groups can be removed under conditions that are mutually exclusive in regard to the other class or classes of protecting groups. Methods of removal of each independent class of protecting groups include but are not limited to acid hydrolysis, base hydrolysis, photolytic cleavage and hydrogenation. Thus, by proper selection of the amino acid backbone protecting group, orthogonally protected guanine PNA synthons can be synthesized.

Following a similar procedure as described above for the formation of a mixed anhydride, the amino protected backbone is added to the cooled solution of the mixed anhydride. The reaction is allowed to proceed for a sufficient time to permit coupling, and therefore, formation of the guanine PNA synthon. The guanine PNA synthon has the formula:

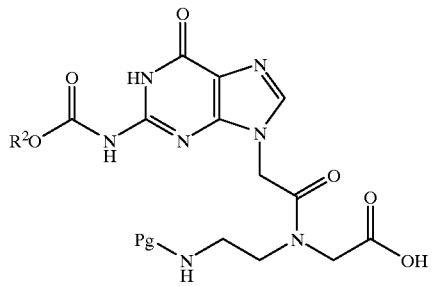

The groups represented by Pg and $R^2$ are the same as previously described. Preferably, the protecting group (Pg) is 9-fluorenylmethyloxycarbonyl and the $R^2$ group is a diphenyl group wherein each of $A_1$–$A_{10}$ is hydrogen and $R^4$ is hydrogen. The preferred guanine PNA synthon (compound VIII in FIG. 2) has the formula:

VIII

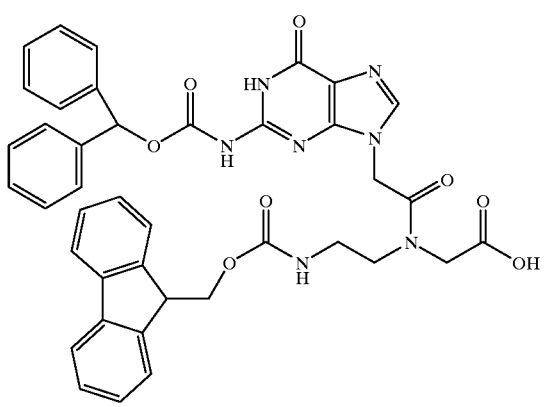

Step 5

If required, hydrolysis of the backbone ester group of a guanine PNA synthon ester yields the guanine PNA synthon. Hydrolysis of the backbone ester group comprises the steps of: first reacting the backbone ester group of the guanine PNA synthon ester with a base thereby generating a salt of the carboxylic acid group and then neutralizing the salt of the carboxylic acid with an acid. The base should be strong enough to enable the hydroxide ion to displace the alcohol of the ester. Preferably the base is an inorganic base such as lithium hydroxide, sodium hydroxide or potassium hydroxide. Hydrolysis of the backbone ester group occurs between about –5° C. and about 50° C., but preferably is performed below ambient temperature. The solvent for hydrolysis is a mixture of one or more organic solvents and water containing a ratio between about 10 and about 90 percent water by volume. Suitable organic solvents include, but are not limited to, methanol, ethanol, isopropanol and acetonitrile. The acid used to neutralize the salt of the carboxylic acid group may be organic or inorganic and preferably has a pKa of less than about two (2) thereby enabling the protonation of the carboxylic acid group.

In one embodiment, the guanine PNA synthon is a compound of the formula:

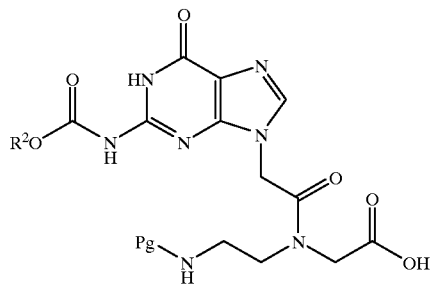

The groups represented by Pg and $R^2$ are as defined above. With reference to FIG. 1, the guanine PNA synthon is a compound of formula:

V

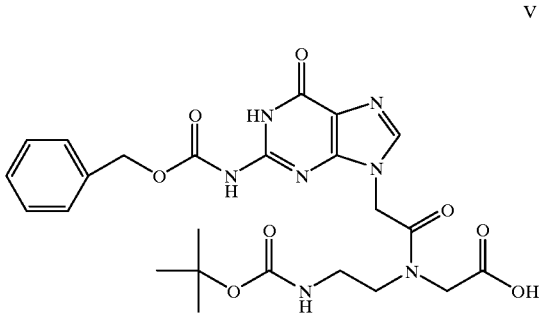

In the preferred embodiment, the guanine PNA synthon has the formula:

VIII

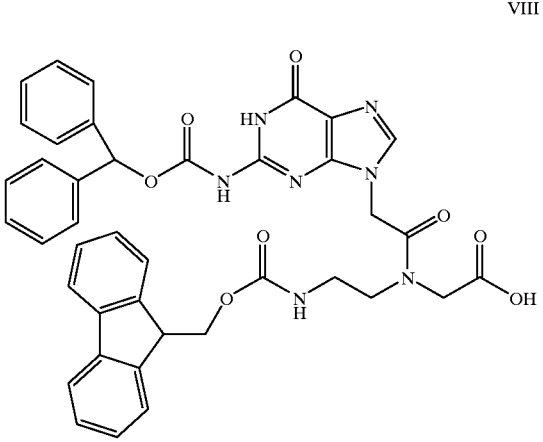

Adenine and Cytosine PNA Synthon Synthesis

Figure 3:
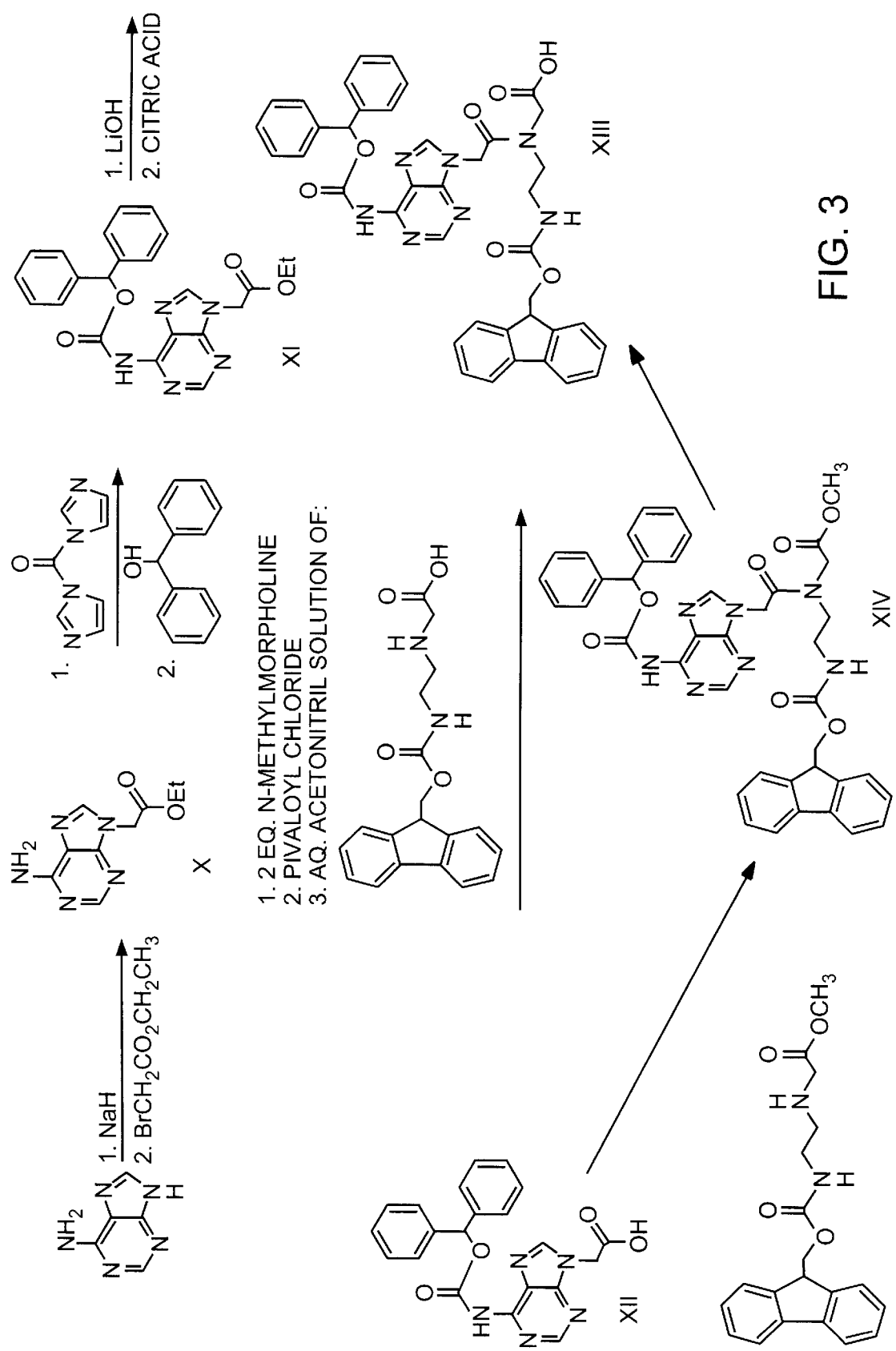
FIG. 3 is a schematic representation of the synthesis of the preferred adenine PNA synthon of this invention.
Figure 4:
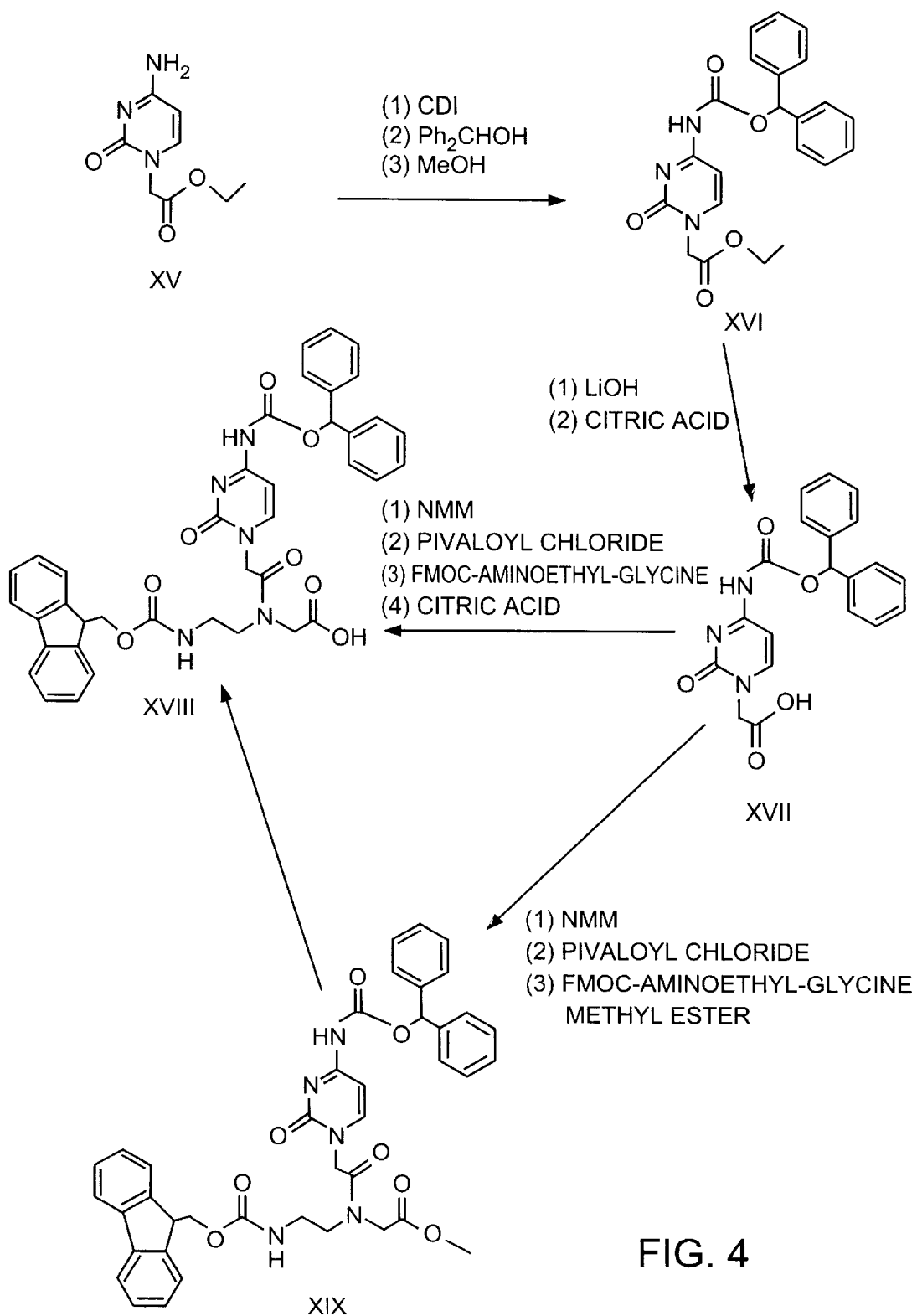
FIG. 4 is a schematic representation of the synthesis of the preferred cytosine PNA synthon of this invention.
Figure 5A:
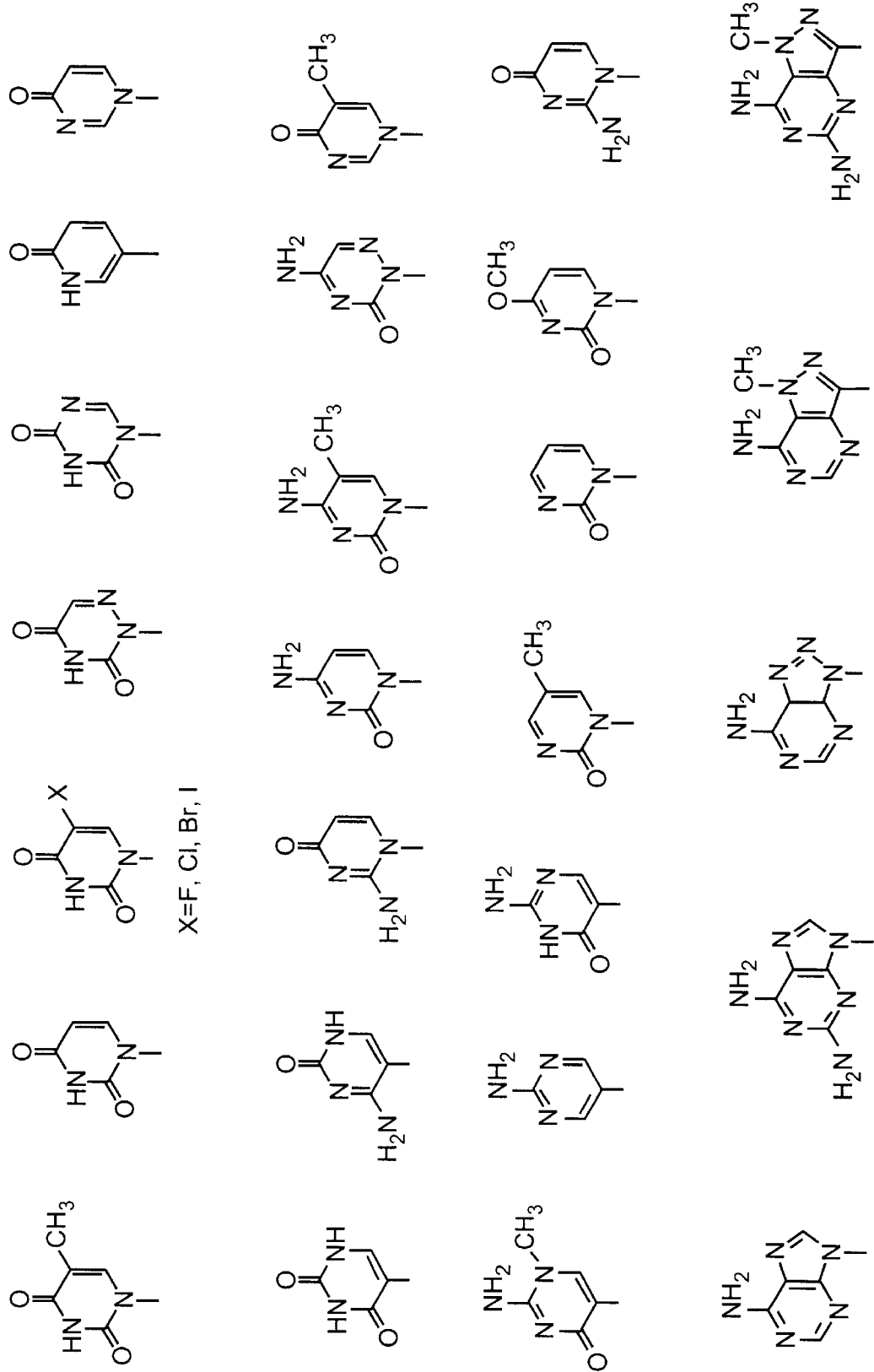
FIGS. 5A and 5B are charts illustrating the structural representations of natural and unnatural nucleobases useful in this invention.
Figure 5B:
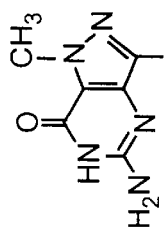
Figure 5B:
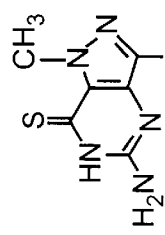
Figure 5B:
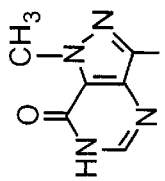
Figure 5B:
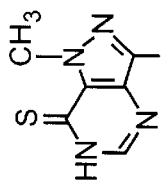
Figure 5B:
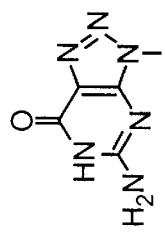
Figure 5B:
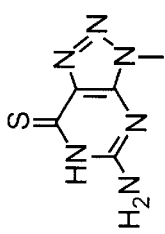
Figure 5B:
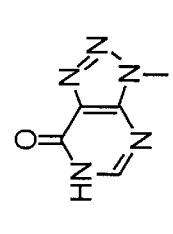
Figure 5B:
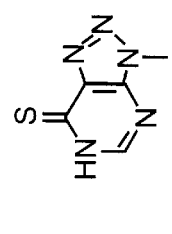
Figure 5B:
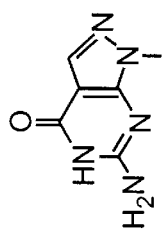
Figure 5B:
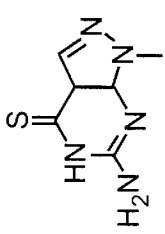
Figure 5B:
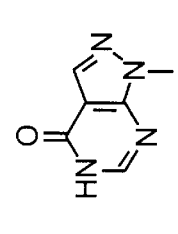
Figure 5B:
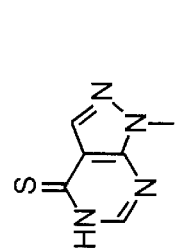
Figure 5B:
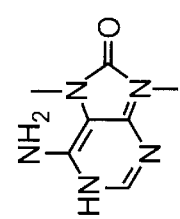
Figure 5B:
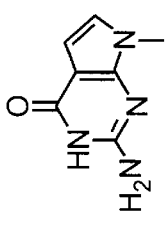
Figure 5B:
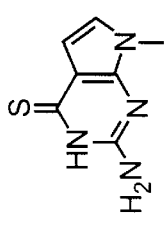
Figure 5B:
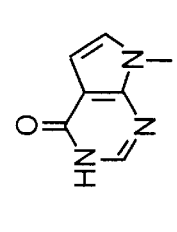
Figure 5B:
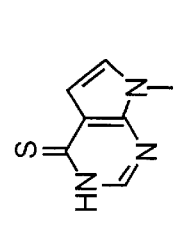
Figure 5B:
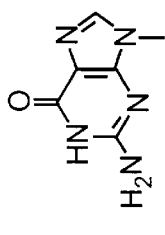
Figure 5B:
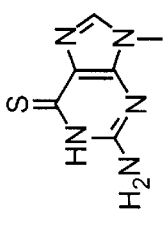
Figure 5B:
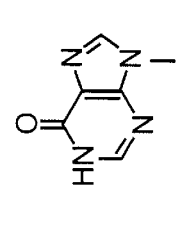
Figure 5B:
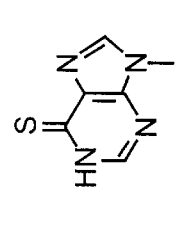

In another embodiment, the invention is a method for the preparation of an adenine PNA synthon (see FIG. 3) and a cytosine PNA synthon (see FIG. 4).

Step 1

The starting material for the preparation of the carbamate protected nucleobase side chain moiety is a partially protected nucleobase compound having an acetate ester substituent. The partially protected adenine compound has the formula:

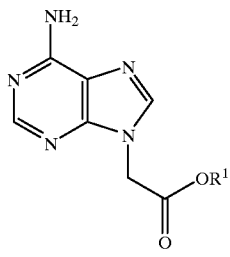

and the partially protected cytosine compound has the formula:

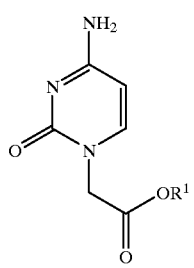

The atom or group represented by R[1] is methyl, ethyl, 2,2,2-trichloroethyl, 2-(trimethylsilyl)-ethyl, 2-(phenylthio)-ethyl, propyl, isopropyl, n-butyl, t-butyl, allyl, 1-isopropyl allyl, cinnamyl, 4-nitrocinnamyl, or a substituted or unsubstituted benzyl of the formula:

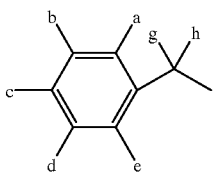

The atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, $NO_2$, $-SO_3H$, $-CN$, $-SCH$, and $-(O)SCH_3$. The atom or group represented by each of g–h is the same or different and is independently selected from the group consisting of hydrogen and methyl.

With reference to FIG. 3, the preferred partially protected adenine compound has the formula:

X

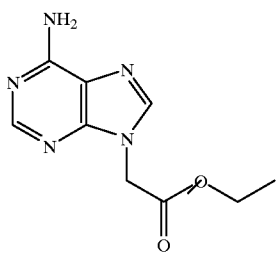

With reference to FIG. 4, the preferred partially protected cytosine compound has the formula:

XV

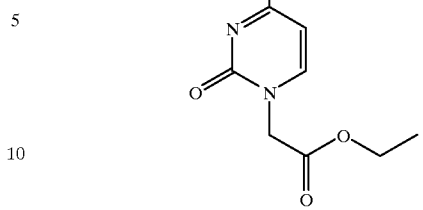

Generally, the partially protected nucleobase compound is transformed into a fully protected nucleobase compound by sequential reaction with an electrophilic carbonyl equivalent and an alcohol, followed by quenching with a polar solvent. Thus, by the method of this invention, the partially protected nucleobase compound is reacted with at least one molar equivalent of carbonyldiimidizole thereby generating an N-substituted intermediate compound. Heat may be required to facilitate the formation of the N-substituted intermediate compound, which is the isocyanate derivative formed at the exocyclic amino group. Thin layer chromatography (tlc) may be utilized to follow the progress of the reaction. The reaction is typically performed in a non-nucleophilic anhydrous solvent which at least partially dissolves the partially protected nucleobase compound. Some examples of suitable solvents include, but are not limited to, diethyl ether, diisopropylether, dioxane, dimethylformamide, tetrahydrofuran, acetonitrile, ethyl acetate, dichloromethane, chloroform, carbon tetrachloride, benzene and toluene. The preferred solvent is dimethylformamide.

Phosgene, while an electrophilic carbonyl equivalent, was found to be unsuitable for the conversion of the partially protected adenine compound into the corresponding fully protected nucleobase compound. In the case of adenine, phosgene is believed to react at the N7 heterocyclic nitrogen atom as previously described in the guanine section. However, carbonyldiimidazole was determined to possess the proper electrophilicity for selective reaction at only the exocyclic amino group of the partially protected adenine compound and the partially protected cytosine compound. Additionally, other electrophilic carbonyl equivalents with similar electrophilic properties may also be employed for this transformation.

The N-substituted intermediate compound is not isolated because it is easily hydrolyzed back to the starting partially protected nucleobase compound. Therefore, the N-substituted intermediate compound is reacted in situ with an alcohol thereby generating the fully protected nucleobase compound. Though it is known that an alcohol reacts with an isocyanate compound to produce a carbamate, this chemistry has yet to be applied to the synthesis of carbamate protected nucleobase compounds. Advantageously, this method of carbamate formation allows various alcohols to be utilized, providing a versatile synthetic procedure. The ability to react various alcohols allows formation of carbamate groups that can be removed under mild conditions. For example, in a preferred embodiment, benzhydrol is the alcohol which, upon reaction with the N-substituted intermediate compound, forms the protecting group benzhydroloxycarbonyl (Bhoc). Benzhydrol was chosen because it was known to create a fairly acid labile carbamate protecting group. See Seiber et al. Helvetica Chemica Acta (1968) 51:614–622. The lability of this protecting group is demonstrated by its rapid and efficient removal in trifluoroacetic acid; the half-life of the reaction is less than one minute. Thus, alcohols can be selected with various chemical properties and substituents so as to tailor the resulting carbamate protecting group for cleavage under mild conditions.

Suitable alcohols which will react with the N-substituted intermediate compound include, but are not limited to, methanol, ethanol, 2,2,2-trichloroethanol, 2-(trimethylsilyl)-ethanol, n-propanol, isopropanol, n-butanol, and t-butanol. The alcohol may be allyl alcohol or an allyl alcohol derivative such as 1-isopropylallyl alcohol, cinnamyl alcohol, or $^4$-nitrocinnamyl alcohol. Additionally, the alcohol may be a substituted or unsubstituted benzyl alcohol of the general formula:

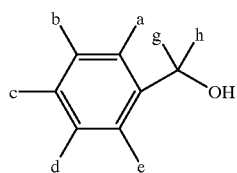

The atom or group represented by each a–e is the same or different and is independently selected from the group consisting of F, Cl, Br, I, hydrogen, methyl, ethyl, isopropyl, t-butyl, phenyl, methoxy, ethoxy, —NO$_2$, —SO$_3$H, —CN, —SCH$_3$, and —(O)SCH$_3$. The atom or group represented by g–h is the same or different and is independently selected from the group consisting of hydrogen and methyl.

Preferably, the alcohol is a diphenyl group having the formula:

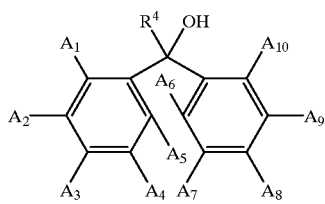

The atom or group represented by A$_1$–A$_{10}$ is independently selected from the group consisting of F, Cl, Br, I, hydrogen, methyl, ethyl, methoxy and ethoxy and the atom or group represented by R$^4$ is selected from the group consisting of hydrogen, methyl and ethyl. The most preferred alcohol is a diphenyl group wherein each of A$_1$–A$_{10}$ is hydrogen and R$^4$ is hydrogen.

The alcohol also may be a thioether group having the formula:

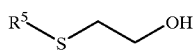

The group represented by R$^5$ is selected from the group consisting of methyl, ethyl, propyl, isopropyl, n-butyl, t-butyl and a phenyl group, wherein the phenyl group is a group of the formula:

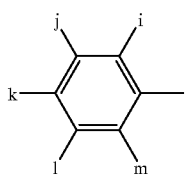

The atom or group represented by each i–m is the same or different and is independently selected from the group consisting of F, Cl, Br, I, hydrogen, methyl, ethyl, isopropyl, t-butyl, phenyl, methoxy, ethoxy, —NO$_2$, —SO$_3$H, —CN, —SCH$_3$, and —(O)SCH$_3$.

In addition, the alcohol can be an ethyl group having the formula:

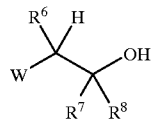

The group represented by W is an electron withdrawing group and the atom or group represented by each of R$^6$–R$^8$ is the same or different and is independently selected from the group consisting of hydrogen, methyl, ethyl, n-propyl, isopropyl, n-butyl and t-butyl. Preferred electron with drawing groups include cyano, alkyl sulfonyl, aryl sulfonyl, phenyl and substituted phenyl, such as p-nitrophenyl, o-nitrophenyl and p-alkyl sulfonyl phenyl.

After sufficient time is allowed for the conversion of the partially protected nucleobase compound into the fully protected nucleobase compound, during which time heat may applied, the reaction is quenched with a polar solvent. Examples of polar solvents include, but are not limited to, water, methanol and ethanol. In the case of the fully protected adenine compound, water is the preferred quenching solvent. The preferred quenching solvent for the fully protected cytosine compound is methanol.

Thus, the fully protected adenine compound has the formula:

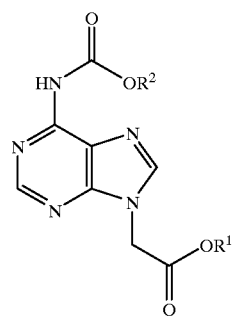

and the fully protected cytosine compound has the formula:

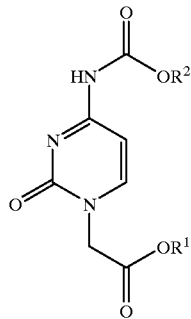

The group represented by $R^1$ is defined above. The group represented by $R^2$ is methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a substituted benzyl as set forth above, or a diphenyl group of the formula:

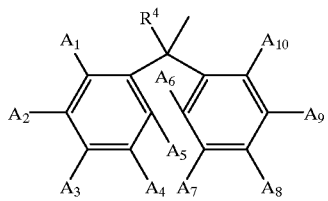

The atom or group represented by each of $A_1$–$A_{10}$ is independently selected from the group consisting of F, Cl, Br, I, hydrogen, methyl, ethyl, methoxy and ethoxy, and the atom or group represented by $R^4$ is hydrogen, methyl or ethyl;

The group represented by $R^2$ also can be a thioether group having the formula:

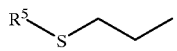

The group represented by $R^5$ is methyl, ethyl, propyl, isopropyl, n-butyl, t-butyl or a phenyl group, wherein the phenyl group has the formula:

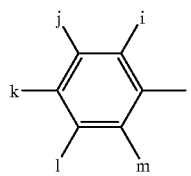

The atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, $NO_2$, $—SO_3H$, $—CN$, $—SCH_3$, and $—(O)SCH_3$.

In another embodiment, $R^2$ can be an ethoxycarbonyl group having the formula:

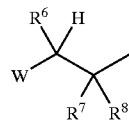

The group represented by W is an electron withdrawing group and the atom or group represented by each of $R^6$–$R^8$ is the same or different and is independently selected from the group consisting of hydrogen, methyl, ethyl, n-propyl, isopropyl, n-butyl and t-butyl.

The preferred fully protected adenine compound has the formula:

X

The preferred fully protected cytosine compound has the formula

XIV

Step 2

The fully protected nucleobase compound is next converted into a carbamate protected nucleobase side chain moiety by hydrolysis of the acetate ester group. The fully protected nucleobase compound is first dissolved in an appropriate solvent system. Heating may be required to completely dissolve the fully protected nucleobase compound. Some examples of solvent systems include, but are not limited to, ethanol/acetonitrile; methanol/acetonitrile; ethanol/acetonitrile/water; methanol/acetonitrile/water; ethanol/methanol/acetonitrile; and ethanol/methanol/acetonitrile/water. If water is not initially included in the solvent system, upon complete dissolution of the fully protected adenine compound, water is added. The preferred solvent system for dissolving the carbamate protected adenine compound is ethanol/acetonitrile. After dissolution is achieved, water is added. For the carbamate protected cytosine compound, the preferred solvent system for dissolution is ethanol/methanol/acetonitrile/water.

The solution containing the fully protected nucleobase compound is cooled in an ice bath, preferably to a temperature below about 10° C. A solution of a metal hydroxide in water is added to the cooled solution and the temperature is allowed to increase. Typically, the metal hydroxide is a group one transition metal hydroxide such as lithium hydroxide, sodium hydroxide, potassium hydroxide or cesium hydroxide. The preferred metal hydroxide is lithium hydroxide for both the fully protected adenine and cytosine compounds. The hydrolysis is allowed to proceed for a relatively short period of time, depending on the scale of the reaction, and then quenched by the addition of an aqueous acid solution. For example, the hydrolysis of approximately 75 mmoles of the fully protected cytosine compound with a methyl ester acetate group is allowed to occur for about 6 minutes before quenching of the reaction. Acids used in the quenching step include but are not limited to citric acid, hydrochloric acid and potassium hydrogen sulfate. Preferably, the acid is citric acid in both nucleobase examples.

After acidification of the hydrolysis solution, the carbamate protected nucleobase side chain moiety is collected. The carbamate protected adenine side chain moiety has the formula:

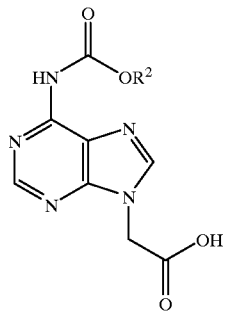

and the carbamate protected cytosine side chain moiety has the formula:

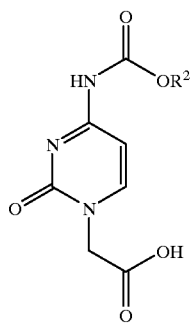

The group represented by $R^2$ is defined above.

A preferred carbamate protected adenine side chain moiety has the formula:

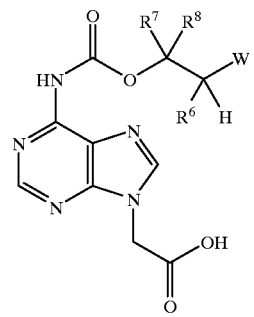

and a preferred carbamate protected cytosine side chain moiety has the formula:

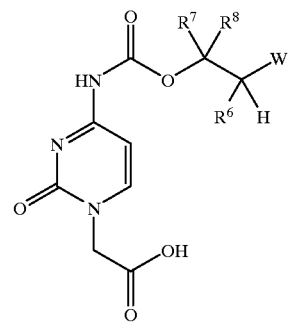

The group represented by W is an electron withdrawing group and the atom or group represented by each of $R^6$–$R^8$ is the same or different and is independently selected from the group consisting of hydrogen, methyl, ethyl, n-propyl, isopropyl, n-butyl and t-butyl. Preferred electron withdrawing groups include, but are not limited to, cyano, alkyl sulfonyl, aryl sulfonyl, phenyl and substituted phenyl, such as p-nitrophenyl, o-nitrophenyl and p-alkyl sulfonyl phenyl. A more preferred carbamate protected adenine or cytosine side chain moiety occurs when W is a cyano group, $R^6$ is a hydrogen atom and each of $R^7$ and $R^8$ is a methyl group.

The preferred carbamate protected adenine side chain moiety has the formula:

XII

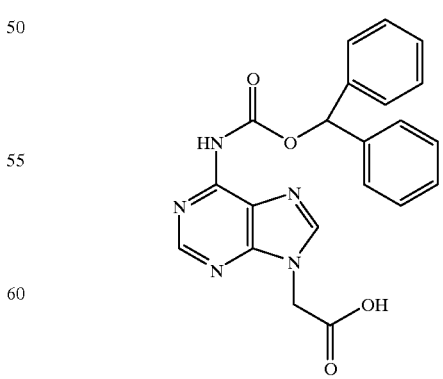

The preferred carbamate protected cytosine side chain moiety has the formula:

XVII

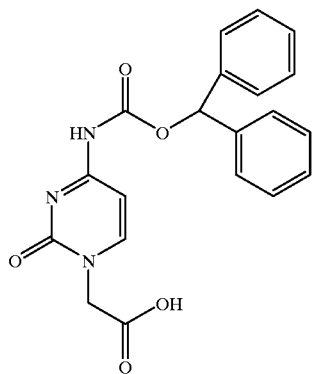

Step 3

Coupling of the carbamate protected nucleobase side chain moiety to the amino protected backbone of the amino acid N-(2-aminoethyl)-glycine produces a PNA synthon. A "PNA synthon" is defined as the carbamate protected nucleobase side chain moiety coupled to the amino protected backbone of the amino acid N-(2-aminoethyl)-glycine either as a free carboxylic acid or an ester. While a distinction between the acid and ester is made in the case of guanine, the acid and ester distinction for the adenine and cytosine PNA synthons was consolidated for brevity of description.

The coupling can be accomplished by a number of methods. Often the carboxylic acid functional group of the carbamate protected nucleobase side chain moiety is converted into an activated form such as an ester, an acid chloride or a mixed anhydride. Examples of coupling reagents used to facilitate this transformation include, but are not limited to, carbodiimide reagents such as dicyclohexylcarbodiimide (DCC) and diisopropylcarbodiimide (DIPCDI); phosphonium salts such as benzotriazol-1-yloxytris(dimethylamino)phosphonium hexafluorophospate (BOP), and uranium salts such as HBTU and HATU. Following activation, the side chain moiety is reacted with the amino protected backbone to form the PNA synthon.

In general, the mixed anhydride method has an economic advantage over the use of the more expensive coupling reagents and is the preferred method. Examples of sterically hindered acid chlorides used to form mixed anhydrides include isobutyryl chloride, trimethylacetyl chloride (pivaloyl chloride) and adamantane carboxyl chloride. The most preferred mixed anhydride for coupling the carbamate protected nucleobase side chain moiety to the amino protected backbone is trimethylacetyl chloride (pivaloyl chloride).

Generally, the mixed anhydride of the carbamate protected nucleobase side chain moiety is formed by treatment of the carbamate protected nucleobase side chain moiety with a non-nucleophilic base followed by reaction with an acid chloride. Non-nucleophilic bases useful in this step of the reaction sequence include, but are not limited to, triethylamine, diisopropylethylamine, N-methyl morpholine and N-ethyl morpholine. The preferred non-nucleophilic base is N-methyl morpholine. Specifically, the acid chloride is added to a cooled solution of the carbamate protected nucleobase side chain moiety in the presence of the non-nucleophilic base. After stirring at below ambient temperature, preferably about 0° C., for a sufficient time to allow formation of the mixed anhydride, an aqueous solution of the amino protected backbone in the presence of a non-nucleophilic base is then added to the cooled solution. Examples of non-nucleophilic bases are those previously described. The preferred non-nucleophilic base for the amino protected backbone solution is triethylamine.

The amino protected backbone of the amino acid N-(2-aminoethyl)-glycine has the formula:

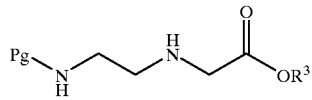

The group represented by Pg is a protecting group such as alkyloxycarbonyl, 9-fluorenylmethyloxycarbonyl, methyl-1-(4-biphenyl)-ethyloxycarbonyl, 1-methyl-1-phenyl-ethyloxy carbonyl, triphenylmethyl, 4methoxy-triphenylmethyl, or 4,4'-dimethoxy-triphenylmethyl. The atom or group represented by $R^3$ is hydrogen or an alkyl group such as methyl or ethyl. The preferred backbone protecting group (Pg) is 9-fluorenylmethyloxycarbonyl (Fmoc) and the preferred $R^3$ substituent is hydrogen. Thus, the preferred amino protected backbone has the formula:

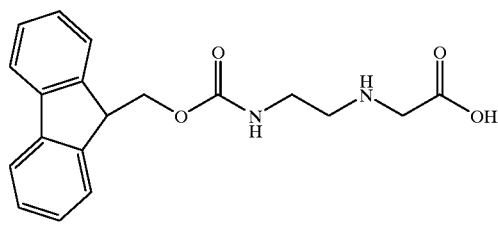

The Fmoc protecting group is a well known base labile protecting group used in peptide synthesis. By the method of this invention, since the exocyclic amino group of the nucleobase is protected as an acid labile carbamate, coupling the preferred Fmoc amino protected backbone to the nucleobase side chain moiety results in an orthogonally protected PNA synthon. Orthogonal is defined as a system of protecting groups wherein each independent class of protecting groups can be removed under conditions that are mutually exclusive in regard to the other class or classes of protecting groups. Methods of removal of each independent class of protecting groups include but are not limited to acid hydrolysis, base hydrolysis, photolytic cleavage and hydrogenation. Thus, by proper selection of the amino acid backbone protecting group, orthogonally protected PNA synthons can be synthesized.

After addition of the amino protected backbone to the cooled solution of the mixed anhydride, the reaction is allowed to proceed for a sufficient time to permit coupling, and therefore, formation of the PNA synthon. The adenine PNA synthon has the formula:

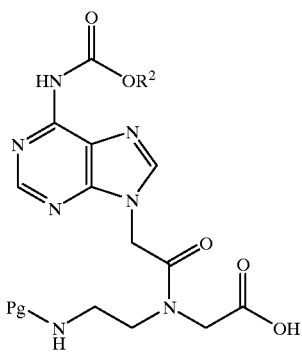

and the cytosine PNA synthon has the formula:

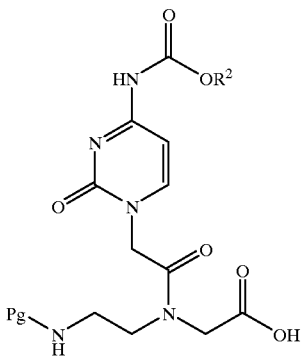

The groups represented by Pg and $R^2$ are the same as previously described. Preferably, the protecting group (Pg) is 9-fluorenylmethyloxycarbonyl and the $R^2$ group is a diphenyl group wherein each of $A_1$–$A_{10}$ is hydrogen and $R^4$ is hydrogen. The preferred adenine PNA synthon has the formula:

XIII

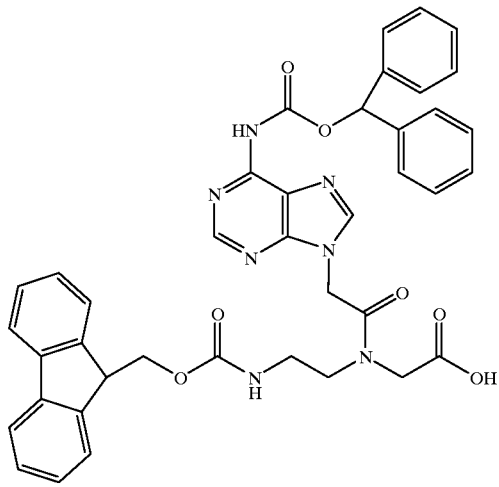

The preferred cytosine PNA synthon has the formula:

XVIII

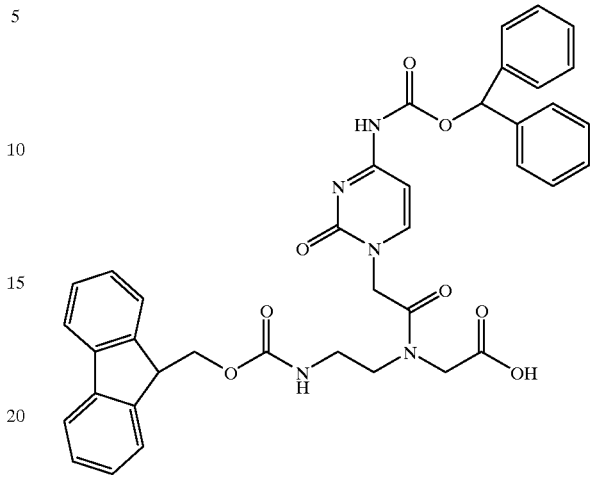

Alternatively, the PNA synthon can be made from an amino protected backbone having an alkyl group as $R^3$. With an alkyl group as $R^3$, the amino protected backbone is an amino protected backbone ester. If the amino protected backbone ester is coupled to the carbamate protected nucleobase side chain moiety, subsequent hydrolysis of a backbone ester group is required to produce a PNA synthon suitable for PNA or nucleic acid polymer synthesis.

Generally, following the previously described procedure, the carbamate protected nucleobase side chain moiety is reacted with a sterically hindered acid chloride in the presence of a non-nucleophilic base to form a mixed anhydride of the carbamate protected nucleobase side chain moiety. A salt of the amino protected backbone ester of N-(2-aminoethyl)-glycine is added to the cooled solution of the mixed anhydride and allowed to warm to room temperature while stirring a sufficient time to allow the coupling to occur. Examples of salts of the amino protected backbone ester of N-(2-aminoethyl)-glycine useful in this transformation include, but are not limited to, hydrochloride and trifluoroacetic acid salts. The preferred salt is the trifluoroacetic acid salt. After the coupling reaction is complete, either the solid PNA synthon precipitates and is collected or the reaction mixture is poured into chilled water whereupon the PNA synthon precipitates and is collected. The adenine PNA synthon has the formula:

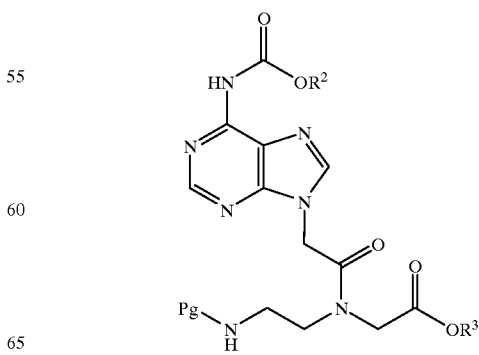

and the cytosine PNA synthon has the formula:

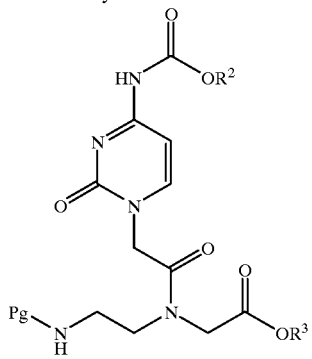

The groups represented by Pg and $R^2$ are the same as previously described. The group represented by $R^3$ is methyl, ethyl and allyl. Preferably, $R^3$ is methyl, Pg is 9-fluorenylmethyloxycarbonyl and $R^2$ is a diphenyl group wherein each of $A_1$–$A_{10}$ is hydrogen and $R^4$ is hydrogen. The preferred adenine PNA synthon has the formula:

XIV

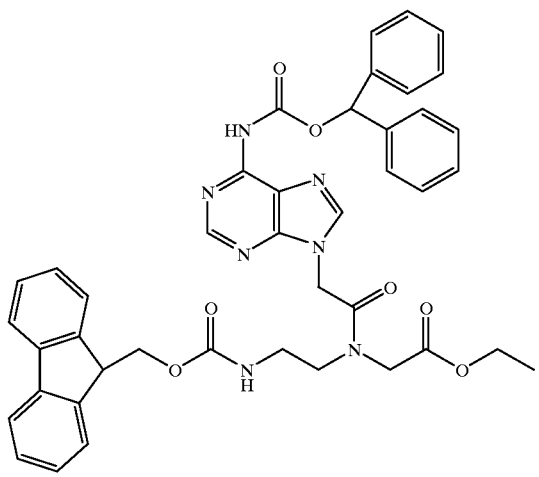

The preferred cytosine PNA synthon has the formula:
XIX

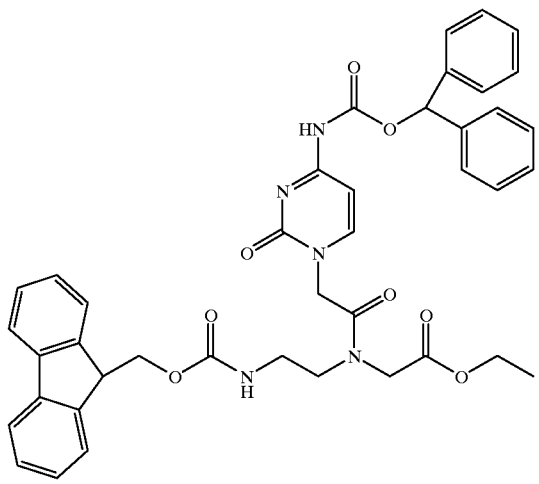

Following formation of the PNA synthon having the backbone carboxylic acid protected as an ester, the ester group must be hydrolyzed for subsequent oligomer synthesis. Generally, the backbone carboxylic acid protected PNA synthon is suspended in a cooled aqueous solvent system and an aqueous solution of a metal hydoxide solution is added. Examples of solvents found in the aqueous solvent system include, but are not limited to, water, acetone and acetonitrile, in various combinations. Metal hydroxides useful in the hydrolysis include, but are not limited to, lithium hydroxide, sodium hydroxide, potassium hydroxide and cesium hydroxide. Preferably, the metal hydroxide is lithium hydroxide.

After the hydrolysis reaction is complete, the reaction is quenched and the PNA synthon can be isolated and purified. If the backbone amino protecting group is basic labile and suseptible to removal under the basic conditions, an activated form of the backbone amino protecting group can be added to the solution prior to isolation of the PNA synthon, thereby reprotecting any amino backbone groups that were inadvertantly removed. For example, if the amino backbone protecting group is the base labile protecting group 9-fluorenylmethyloxycarbonyl, addition of 9-fluorenylmethyloxycarbonyl succinimide after the hydrolysis and before isolation will help to increase the overall yield of desired PNA synthon. The adenine PNA synthon isolated will have the formula:

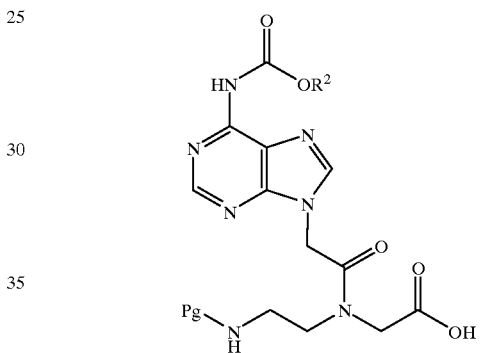

and the cytosine PNA synthon will have the formula:

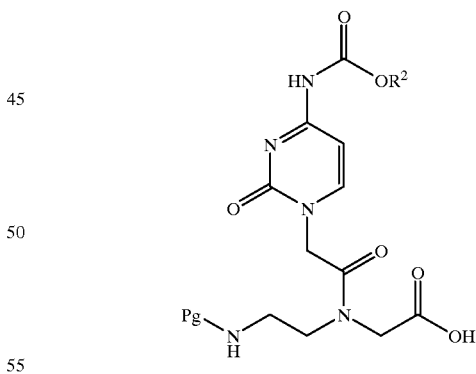

The groups represented by Pg and $R^2$ are the same as previously described. Preferably, the protecting group (Pg) is 9-fluorenylmethyloxycarbonyl and the $R^2$ group is a diphenyl group wherein each of $A_1$–$A_{10}$ is hydrogen and $R^4$ is hydrogen. The preferred adenine PNA synthon is compound XIV and the preferred cytosine PNA synthon is compound XIX.

Another possible method of coupling the carbamate protected nucleobase side chain moiety to the amino protected backbone involves the use of transient protection for the carboxylic acid functionality on the amino protected backbone rather than the ester form of the amino protected backbone previously described. Generally, following the previously described procedure, the carbamate protected nucleobase side chain moiety is reacted with a sterically hindered acid chloride in the presence of a non-nucleophilic base to form a mixed anhydride of the carbamate protected nucleobase side chain moiety. Following formation of the mixed anhydride, a solution of the amino protected backbone in the presence of a non-nucleophilic base and a sterically hindered silyl choride is added to the cooled mixed anhydride solution. After the reaction is stirred for a sufficient time to allow coupling, the reaction is quenched, dried and then subjected to treatment with a silyl removing group (e.g., a fluoride compound). Subsequent to removal of the silyl protecting group, the desired PNA synthon is isolated.

The adenine PNA synthon has the formula:

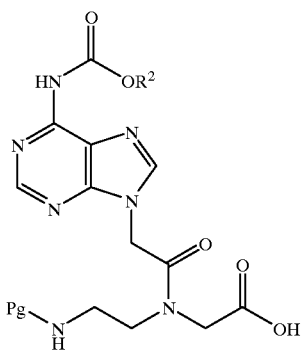

and the cytosine PNA synthon has the formula:

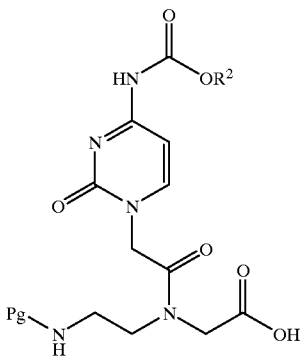

The groups represented by Pg and $R^2$ are the same as previously described. Preferably, the protecting group (Pg) is 9-fluorenylmethyloxycarbonyl and the $R^2$ group is a diphenyl group wherein each of $A_1-A_{10}$ is hydrogen and $R^4$ is hydrogen. The preferred adenine PNA synthon is compound XIV and the preferred cytosine PNA synthon is compound XIX.

PNA Synthesis

The PNA synthons as their free carboxylic acids can be coupled to each other to form a PNA oligomer (PNA). Additionally, the PNA synthons can be coupled to other peptide monomers and nucleic acid monomers such as nucleotides, to form various combinations of "bio" oligomers or polymers. Examples of oligomers include, but are not limited to, PNA, DNA and RNA sequences; oligonucleotides; polypeptides; and their various combinations. For example, PNA-DNA chimeras are disclosed in a companion patent application entitled "PNA-DNA Chimeras and PNA Synthons for Their Preparation" U.S. application Ser. No. 08/480,228 filed Jun. 7, 1995) which is herein specifically incorporated by reference in its entirety. Because the chemistry of the PNA synthons is compatible with commercially available synthesizers, the synthons are readily transformed into polymeric chains of various lengths and sequences.

Various methods already described in the chemical literature for peptide synthesis are generally applicable to PNA oligomer synthesis. These methods include, but are not limited to, solid phase peptide synthesis and solution synthesis. For example, in solid-phase synthesis, following coupling of the first amino acid, the next step is the systematic elaboration of the desired PNA chain. This elaboration involves repeated deprotection/coupling cycles. The temporary backbone protecting group on the last-coupled amino acid, such as Fmoc, is quantitatively removed by a suitable treatment, for example by base treatment with piperidine, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, the carboxyl group of the incoming amino acid can be reacted directly with the N-terminal of the last-coupled amino acid with the assistance of a condensation reagent such as, for example, dicyclohexylcarbodiimide (DCC) (Sheehan & Hess, et al., *J. Am. Chem. Soc.*, 1955, 77, 1067) and diisoproplycarbodiimide (DIC) (Sraantakis et al., *Biochem. Biophys. Res. Commun.*, 1976, 73, 336) or derivatives thereof. Alternatively, it can be bound by providing the incoming amino acid in a form with the carboxyl group activated by any of several methods, including the initial formation of an active ester derivative such as a 2,4,5-trichlorophenyl ester (Pless, et al., Helv. Chim. Acta, 1963, 46, 1609), a phthalimido ester (Nefkens, et al., J. Am. Chem. Soc., 1961, 83, 1263), a pentachlorophenyl ester (Kupryszewski, Rocz. Chem., 1961, 35, 595), a pentafluorophenyl ester (Kovacs, et al., J. Am. Chem. Soc., 1963, 85, 183), an o-nitrophenyl ester (Bodanzsky, Nature, 1955, 175, 685), an imidazole ester (Li, et al., J. Am. Chem. Soc., 1970, 92, 7608), and a 3-hydroxy-4-oxo-3,4-dihydroquinazoline (Dhbt-OH) ester (Konig, et al., Chem. Ber., 1973, 103, 2024 and 2034), or the initial formation of an anhydride such as a symmetrical anhydride (Wieland, et al., Angew. Chem., Int. Ed. Engl., 1971, 10,336). Benzotriazolyl N-oxytrisdimethylaminophosphonium hexafluorophosphate (BOP), "Castro's reagent" (see, e.g., Rivaille, et al., Tetrahedron 1980, 36, 3413) is recommended when assembling PNA molecules containing secondary amino groups. Preferred reagents for activity the carboxylic acid groups include 1-hydroxy-7-azabenzotriazole (HOAT) and its phosphonium and uronium salts. See Carpino, J.Am. Chem. Soc., 1993, 115, 4397. Finally, activated PNA monomers analogous to the recently-reported amino acid fluorides (Carpino, J. Am. Chem. Soc., 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

The invention, being generally described above, is now more specifically illustrated by way of the following examples, which are not meant to limit the invention, unless otherwise noted.

EXAMPLES

Example 1
Synthesis of Benzyl 2-[6'-chloro(9'-purinyl)]acetate (I)

To 6-chloro-2-amino purine (300 g. 1.77 mole; Pharma-Waldorf GmbH, Germany, P/N 471720) and potassium carbonate (366 g; 2.65 mole, Aldrich Chemical, Milwaukee, Wis. (hereinafter Aldrich) P/N 34,782-5) was added dimethyl formamide (DMF, 3 L) and the solution was warmed until all the 2-amino-6-chloropurine dissolved (84° C.). The mixture was then cooled in an ice bath and benzyl-2-bromoacetate (299 mL, 1.89 mole; Aldrich Pl/N 24,563-1) was added dropwise over the course of one and one half hours. The mixture was stirred for an additional three hours at 0° C. and was then stirred overnight at ambient temperature. The following day the reaction mixture was filtered and the filtrate was then poured into a solution containing 7 liters of water and 150 mL of concentrated hydrochloric acid (HCl). The mixture was stirred for 2 hrs. and the product was then isolated by filtration. The product was washed thoroughly with water and subsequently recrystallized by portion-wise addition of the solid to boiling acetonitrile (3 L). The very red solution was left overnight and filtered the next day. The product was washed thoroughly with methanol and then diethylether. Yield 386 g (69%); $^1$H-NMR (d$_6$ DMSO) δ 8.14 (1 H,s), 7.4–7.3 (5 H, m), 7.02 (2 H,s), 5.21 (2 H,s), 5.08 (2 H,s).

Example 2
Synthesis of 2-(N-[benzyloxycarbonyl])-amino-6-chloro-N$^2$-(benzylcarboxymethyl)-purine (IIa)

To Benzyl 2-[6'-chloro(9'-purinyl)]acetate(I) (292 g; 0.920 mole) and triphosgene (98.8 g; 0.33 mole; Aldrich P/N 33,075-2) in an oven-dried 5 L three-necked reaction flask under argon standing in an ice bath was added ice cold anhydrous THF (3 L). The mixture was stirred for 15 min. and thereafter diisopropylethylamine (348 mL; 2.0 mole; Lanchaster Synthesis, Windham, N.H. (hereinafter Lanchaster) P/N 4310) was added dropwise over a period of 35 min. After stirring for an additional 20 min., benzyl alcohol (153 mL; 1.5 mole; Aldrich P/N 10,800-6) was immediately added. The mixture was allowed to stir overnight while warming to ambient temperature. The reaction mixture was then poured into a solution containing 6.5 L of water and 80 mL of concentrated HCl. The mixture was stirred for 2 hrs. at room temperature and the product was collected by vacuum filtration. The solid was washed thoroughly with water and then recrystallized from denatured ethanol (2 L). The product was collected by vacuum filtration and washed twice with cold ethanol. Yield 293 g (70%); $^1$H-NMR (d$_6$ DMSO) δ 10.86 (1 H,s), 8.52 (1 H,s), 7.5–7.3 (10 H,m), 5.22–5.20 (6 H,m).

Example 3
Synthesis of 2-(N-[benzyloxycarbonyl])-N$^2$ (carboxymethyl)-guanine (IIIa)

Sodium hydride (18.0 g; 0.75 mole; Aldrich P/N 22,344-1) was added to 1100 mL of dry THF in a dry 5 L round-bottom flask blanketed with an argon atmosphere. The reaction flask was placed in a dry-ice acetone bath for a period of 15–20 min. To the solution was added drop wise 51.2 mL (0.75 mole) of 3-hydroxypropionitrile (Aldrich Chemical P/N 10,992-4) over a period of 15–20 minutes. After the addition was complete, the dry-ice acetone bath was removed and stirring was continued while the reaction warmed in an ice bath for 2 hours. Thereafter, the 2-(N-[benzyloxycarbonyl]amino-6-chloro-N$^9$-(benzylcarboxymethyl)-purine (II) (67.9 g 0.15 mole) was added as a dry solid, portion-wise over a period of 10–15 minutes. The ice bath was removed and stirring was continued for another 2 hrs. The total volume was reduced to about 500 mL using reduced pressure evaporation. The resulting mixture was poured into a solution containing 4 L of water and 70 mL of concentrated HCl. The mixture was stirred overnight and then filtered the following day. The solid was washed thoroughly with water and then three times with ethyl acetate. Yield 48.5 g (94%) of a white solid. $^1$H-NMR (d$_6$ DMSO) δ 11.55 (1 H,s), 11.38 (1 H,s), 7.95 (1 H,s) 7.5–7.3 (5 H,m) 5.26 (2 H,s) 4.89 (2 H,s).

Example 4
Synthesis of 2-(N-[4-(t-butyl)-benzyloxycarbonyl])-amino-6-chloro-N$^2$-(benzylcarboxymethyl)-purine (IIb)

To Benzyl 2-[6'-chloro(9'-purinyl)]acetate(I) (9.05 g; 30 mmol) and triphosgene (2.97 g; 10 mmol; Aldrich P/N 33,075-2) in an oven-dried 500 mL three-necked reaction flask under argon standing in an ice bath was added ice cold anhydrous THF (100 mL). The mixture was stirred for 15 min. and thereafter diisopropylethylamine (10.5 mL; 60 mmol; Lanchaster, P/N 4310) was added drop wise over a period of 5 min. After stirring for an additional 30 minutes, 4-tert-butylbenzyl alcohol (8 mL; 45 mmol; Aldrich P/N 18,426-8) was immediately added. The mixture was allowed to stir overnight while warming to ambient temperature. The reaction mixture was then poured into a solution containing 1.0 L of water and 13 mL of concentrated HCl. The mixture was stirred for 30 min. at room temperature and then 250 mL of ethyl acetate was added to partition the product. The layers were separated and the organic layer was washed with 125 mL of 5% aqueous sodium bicarbonate. The organic layer was dried with sodium sulfate, filtered and evaporated. The residue was crystallized from 50 mL of toluene. The product was collected by vacuum filtration. Yield 6.88 g (45%); $^1$H-NMR (CDCl$_3$) δ 8.04 (1 H,s), 7.83 (1 H,s), 7.42–7.29 (9 H,m), 5.21 (4 H,s), 5.01 (2 H,s), 1.31 (9 H,s).

Example 5
Synthesis of 2-(N-[4-(t-butyl)-benzyloxcarbonyl])-N$^2$-(carboxymetyl)-guanine (IIIb)

Sodium hydride (1.5 g; 60 mmol; Aldrich P/N 22,344-1) was added to 90 mL of dry THF in a dry 250 mL round-bottom flask blanketed with an argon atmosphere. The reaction flask was placed in a dry-ice acetone bath for a period of 10 min. To the solution was added drop wise 4.1 mL (60 mmol) of 3-hydroxypropionitrile (Aldrich Chemical P/N 10,992-4) over a period of 5-10 minutes. After the addition was complete, the dry-ice acetone bath was removed and stirring was continued while the reaction manned in an ice bath for 2 hours. Thereafter, the 2-(N-[t-(butyl)benzyloxycarbonyl)-amino-6-chloro-N$^9$-(benzylcarboxymethyl)-purine (IIb) (6.1 g; 12 mmol) was added as a dry solid, portion wise over a period of 2–3 minutes. The ice bath was removed and stirring was continued for another 1 hr. Added 200 mL of water and then 9 mL of 6N HCl. The solution was cooled in an ice bath for 30 min. and then the solid was collected by vacuum filtration. The solid was boiled in 50 mL of acetonitrile for 1 hr.

and then the solution was cooled to room temperature. The product was collected by vacuum filtration. Yield 4.13 g (86%); $^1$H-NMR (d$_6$ DMSO) δ11.51 (1 H,s), 11.38 (1 H,s), 7.94 (1 H,s), 7.44–7.33 (4 H, dd), 5.22 (2 H,s) 4.88 (2 H,s), 1.28 (9 H,s).

Example 6
Synthesis of 2-(N-[4-(isopropyl)-benzyloxycarbonyl])-amino-6-chloro-N$^2$-(benzylcarboxymethyl)-purine (IIc)

To Benzyl 2-[6'-chloro(9'-purinyl)]acetate(I) (9.05 g; 30 mmol) and triphosgene (2.97 & 10 mmol; Aldrich P/N 33,075-2) in an oven-dried 500 mL three necked reaction flask under argon standing in an ice bath was added ice cold anhydrous THF (100 mL). The mixture was stirred for 15 min. and thereafter diisopropylethylamine (10.5 mL, 60 mmol; Lanchaster, P/N 4310) was added drop wise over a period of 5–10 min. After stirring for an additional 30 minutes, 4-isopropylbenzyl alcohol (6.9 mL; 45 mmol; Aldrich P/N 19,603-7) was immediately added. The mixture was allowed to stir overnight while warming to ambient temperature. The reaction mixture was then poured into a solution containing 1.0 L of water and 13 mL of concentrated HCl. The mixture was stirred for 30 min. at room temperature and then 250 mL of ethyl acetate was added to partition the product. The layers were separated and the organic layer was washed with 125 mL of 5% aqueous sodium bicarbonate. The organic layer was dried with sodium sulfate, filtered and evaporated. The residue was crystallized from 25 mL of toluene. The product was collected by vacuum filtration. Yield 7.50 g (51%); $^1$H-NMR (CDCl$_3$) δ 0.04 (1 H,s), 7.74 (1 H,s), 7.35–7.20 (9 H,m), 5.22 (4 H,m), 5.02 (2 H,s), 2.96–2.84 (1 H, septet), 1.25 (6 H,d).

Example 7
Synthesis of 2-(N-[4-(isopropyl)-benzyloxycarbonyl)-N$^2$-(carboxymethyl)-guanine (IIIc)

Sodium hydride (1.5 g; 60 mmol; Aldrich P/N 22,344-1) was added to 90 mL of dry THF in a dry 250 mL round-bottom flask blanketed with an argon atmosphere. The reaction flask was placed in a dry-ice acetone bath for a period of 10 min. To the solution was added dropwise 4.1 mL (60 mmol) of 3-hydroxypropionitrile (Aldrich Chemical P/N 10,992-4) over a period of 1–2 minutes. After the addition was complete, the dry-ice acetone bath was removed and stirring was continued while the reaction warmed in an ice bath for 2 hours. Thereafter, the 2-(N-[4-(isopropyl)benzyloxycarbonyl])-amino-6-chloro-N$^9$-(benzylcarboxymethyl)-purine (IIc) (6.1g; 12 mmol) was added as a dry solid, portion-wise over a period of 2–3 minutes. The ice bath was removed and stirring was continued for another 1 hr. Added 300 mL of water and then 11 mL of 6N HCl. The solution was cooled in an ice bath for 30 min. and then the solid was collected by vacuum filtration. The solid was boiled in 50 mL of acetonitrile for 1 hr. and then the solution was cooled to room temperature. The product was collected by vacuum filtration. Yield 4.84 g (84%); $^1$H-NMR (d$_6$ DMSO) δ 11.51 (1 H,s), 11.38 (1 H,s), 8.18 (1 H,s) 7.38–7.24 (4 H,dd) 5.21 (2 H,s) 4.87 (2 H,s), 2.95–2.80 (1 H,septet), 1.2 (6 H,d).

Example 8
Synthesis of 2-(N-[4-(methoxy)-benzyloxycarbonyl])-amino-6-chloro-N$^2$-(benzylcarboxymethyl)-purine (IId)

To Benzyl 2-[6'-chloro(9'-purinyl)]acetate(I) (20 g; 63 mmol) and triphosgene (7.46 g; 25 mmol; Aldrich P/N 33,075-2) in an oven-dried 1 L three-necked reaction flask under argon standing in an ice bath was added ice cold anhydrous THF (189 mL). The mixture was stirred for 20 min. and thereafter diisopropylethylamine (24.1 mL; 140 mmol; Lanchaster, P/N 4310) was added dropwise over a period of 5–10 min. After stirring for an additional 30 minutes, 4-methoxybenzyl alcohol (9.9 mL; 79 mmol; Aldrich P/N 13,690-5) was immediately added. The mixture was allowed to stir overnight while warming to ambient temperature. The reaction mixture was then poured into a solution containing 200 mL of water and 4.7 mL of concentrated HCl. The mixture was stirred for 2 hrs. at room temperature and the product was collected by vacuum filtration. The solid was washed thoroughly with water and then recrystallized from acetonitrile (500 mL). The product was collected by vacuum filtration and washed twice with cold acetonitrile. Yield 16.2 g (55%); $^1$H-NMR (CDCl$_3$) δ10.76 (1 H,s), 8.5 (1 H,s), 7.4–6.8 (9 H,m), 5.2–5.1 (6 H,m), 3.75 (3 H,s).

Example 9
Synthesis of 2-(N-[4-(methoxy)benzyloxycarbonyl])-N$^2$-(carboxymethyl)-guanine (III)d)

Sodium hydride (3.9 g; 160 mmol; Aldrich P/N 22,344-1) was added to 200 mL of dry THF in a dry 1 L round-bottom flask blanketed with an argon atmosphere. The reaction flask was placed in a dry-ice acetone bath for a period of 15–20 min. To the solution was added dropwise 10.95 mL (160 mmol) of 3-hydroxypropionitrile (Aldrich Chemical. P1 N 10,992-4) over a period of 15–20 minutes. After the addition was complete, the dry-ice acetone bath was removed and stirring was continued while the reaction warmed in an ice bath for 2 hours. Thereafter, the 2-(N-[4-(methoxy-benzyloxycarbonyl])-amino-6-chloro-N$^9$-(benzylcarboxymethyl)-purine (IId) (15 g; 32.2 mmol) was added as a dry solid, portion-wise over a period of 10–15 minutes. The ice bath was removed and stirring was continued for another 2 hrs. The total volume was reduced to about 70 mL using reduced pressure evaporation. The resulting mixture was poured into a solution containing 200 mL of water and 21 mL of concentrated HCl. The mixture was stirred overnight and then filtered the following day. The solid was washed thoroughly with water and then three times with ethyl acetate. Yield 9.9 g (82%)$^1$H-NMR (d$_6$ DMSO) δ 11.40 (1 H,s), 7.95 (1 H,s), 7.4–7.3 (2 H,d) 7.0–6.9 (2 H,d) 5.15 (2 H,s) 4.85 (2 H,s), 3.8 (3 H,s).

Example 10
Synthesis of N-([2-[N-benzyloxycarbonyl]-guanine-9-y-acetyl)-N-(2-[t-butyloxycarbonyl]-2-aminoethyl)-glycine ethyl ester (IV)

To 136 g (396 mmole) of 2-(N-[benzyloxycarbonyl])-N$^9$-(carboxymethyl)-guanine (III) was added 1600 mL of dry dimethylformamide (DMF). The solution was stirred for 30 min. while cooling in an ice bath. Trimethylacetyl chloride 97.6 mL (792 mmole) (Aldrich, P/N T7,260-5) was added and the reaction stirred for an additional 10 min. N-methyl morpholine (218 mL; 1.98 mole; Fluka Chemical Ronkonkoma, N.Y., P/N 67870) was added dropwise over 20–30 minutes and then the reaction stirred for another 30 minutes. To the stirring solution was added 117 g (475 mmole) of N$^1$-(tert-butyloxycarbonyl)-N$^4$-(2-aminoethyl)-glycine ethyl ester (Millipore Corporation, P/N GEN PNABKB) dissolved in 100 mL of dry DMF. The reaction was stirred overnight while warming to room temperature. The insoluble N-methyl morpholine hydrochloride was filtered off and the cake was washed with acetonitrile. To the filtrate was added 2.5 mL of methanol and then the filtrate was completely evaporated to a tan solid. The solid was recrystallized from 3 L of solvent containing 1/1/1 ethanol/ acetonitrile/water. Yield 178.2 g(311 mmole; 78%) Due to the limited rotation around the secondary amide bond, several of the proton signals are split in the ratio of 2:1, wherein the rotomers are distinguishable on the NMR time scale. Thus, several signals corresponding to the major rotomer component are designated by "mj" whereas the minor rotomer component is designated by "mi." $^1$H NMR (DMSO) δ 11.44 (1 H, d), 11.34 (1 H, s), 7.80 (1 H, m), 7.5–7.3 (5 H, m), 6.98 (1 H; mj, t), 6.73 (1 H; mi, m), 5.26 (2 H, s), 5.09 (2 H; mj, s), 4.92 (2 H; mj, s), 4.41 (2 H; mi, s), 4.06 (2 H; mj, s), 4.25–4.15 (2 H; mj, q), 4.13 4.03 (2 H; mj, q), 3.60–2.95 (4 H, mm), 1.35 (9 H, s), 1.3–1.1 (3 H, dt).

Example 11
Synthesis of N-([2-[N-benzyloxycarbonyl]-guanine-9-yl-acetyl]-N-(2-[t-butyloxycarbonyl]-aminoethyl)-glycine (V)

To 183.3 g (320 mmol) of N-([2-[N-benzyloxycarbonyl]-guanine-9-yl]-acetyl)-N(2-(t-butyloxycarbonyl)-2-aminoethyl)-glycine ethyl ester (IV) was added 960 mL of ethanol (denatured; VWR Scientific, P/N VWO470), 960 mL of acetonitrile and 480 mL of water. The solution was heated at reflux until all the solid was dissolved. The solution was cooled to ambient temperature and then to less than 5° C. in an ice/salt bath. To the briskly stirring suspension was added rapidly, 1.6 L of cold (<5° C.) 2N lithium hydroxide solution (134.3 g LiOH, VWR Scientific, P/N JTP406 dissolved and diluted to 1.6 L with water). After stirring exactly five minutes, the reaction was quenched by the addition of 1.54 L of cold (<5° C.) aqueous 2N HCl. (The pH of the reaction was 4.5 and the temperature about 16° C. after the addition.) The solution was filtered through a course flitted glass scinter to remove any insoluble material and then cooled to <10° C. To the briskly stirring solution was then added 160 mL of aqueous 2N HCl dropwise over 30 minutes (pH=2–3 by paper). An additional 11 mL of aqueous 3N HCl was then added dropwise to finally adjust the pH to 1–2 by paper. The-solution then stirred in an ice bath for 3 more hrs. and the product was collected by vacuum filtration. The solid was washed liberally with water. Yield 173.6 g (319 mmol; 99%) $^1$H-NMR (d$_6$ DMSO) δ 11.5 (1 H, d), 11.38 (1 H, s), 7.88 (1 H, m), 7.5–7.3 (5 H, m), 7.01 (1 H,; mj, m), 6.76 (1 H; mi, m), 5.26 (2 H, s), 5.09 (2 H; mj, s), 4.94 (2 H; mi, s), 4.32 (2 H; mi, s), 3.99 (2 H; mj, s), 3.5–2.9 (4 H, mm), 1.35 (9 H, s).

Example 12
Synthesis of 2-N-[benzhydroloxycarbonyl])-amino-6-chloro-N$^2$-(benzylcarboxymethyl)-purine (IIe)

To 62 mmol of 2-amino-6 chloro-N$^9$-benzylcarboxymethyl-purine was added about 190 mL of freshly distilled, ice cold, tetrahydrofuran. While the solution stirred in an ice bath, 22.4 mmol of triphosgene was added. The reaction was allowed to stir 1 hr. at 0° C. and then 136 mmol of diisopropylethylamine was added dropwise. After stirring 30 minutes at 0° C., 74.4 mmol of benzhydrol alcohol was added. The reaction was allowed to stir overnight while warming to room temperature. In the morning ethanol was added and the reaction was concentrated to dryness. The residue was partitioned in dichloromethane and an aqueous solution of 10% citric acid. The layers were separated and washed 1× with aqueous 5% sodium bicarbonate solution. The dichloromethane layer was dried, filtered and evaporated. The product was recrystallized form methanol. Yield 54%
$^1$HNMR (d$_6$DMSO) δ 11.0 (1 H, s), 8.5 (1 H,s), 7.6–7.2 (15 H, m), 6.8 (1 H, s), 5.15 (4 H,m)

Example 13
Synthesis of 2-(N-[benzhydroloxycarbonyl])-N$^2$-(carboxymethyl)-guanine (IIIe)

To 365 mmol of 95% sodium hydride was added about 450 mL of freshly distilled tetrahydrofuran. The solution was cooled in an dry ice/acetone bath for 20 minutes (−78° C.) and then 365 mmol of 3-hydroxypropionitrile was added. Reaction was stirred at 0° C. for 2.5 hours and then 73 mmol of 2-(N-[benzhydroloxycarbonyl])-amino-6-chloro-N$^9$-(benzylcarboxymethyl)-purine (IIe) was added. The reaction was allowed to stir overnight while warming to room temperature. In the morning, about 300 mL of the solvent was evaporated and then the residue was poured into a solution containing 800 mL water and then acidified by the addition of a 20% aqueous citric acid solution until the pH was about 3–4. The product was collected by vacuum filtration and then crystallized from methanol. Yield 62%.
$^1$HNMR (d$_6$DMSO) δ 11.7 (1 H, s), 11.2 (1 H, s), 8.95 (1 H, s), 7.6–7.2 (10 H, m), 6.85 (1 H, s) 5.9 (4 H, s)

Example 14
Synthesis of 2-(N-[2-(methylthio)-ethyloxycarbonyl])-amino-6-chloro-N$^2$-(benzylcarboxymethyl)-purine (IIf)

To 50 mmol of 2-amino-6 chloro-N$^9$-benzylcarboxymethyl-purine was added about 200 mL of freshly distilled tetrahydrofuran. The reaction was cooled for 20 minutes in an ice bath and then 20 mmol of triphosgene was added. The reaction was allowed to stir 30 minutes at 0° C. and then 130 mmol of diisopropylethylamine was added dropwise. After stirring 20 minutes at 0° C., 70 mmol of 2-(methylthio)-ethanol was added. The reaction was allowed to stir overnight while warming to room temperature. In the morning, the reaction was concentrated to about half volume and then poured into a stirring solution containing 500 mL of water and 30 mmol of HCl. This mixture was allowed to stir for 30 minutes and then the product was then collected by vacuum filtration. The product was recrystallized from ethanol. Yield 74%
$^1$HNMR (d$_6$DMSO) δ 10.8 (1 H, s), 8.5 (1 H, s), 7.35 (5 H, m), 5.22 (4 H, m), 4.25 (2 H,t), 2.75 (2 H,t), 2.15 (3 H,s)

Example 15
Synthesis of 2-(N-[2-(methylthio)-ethyloxycarbonyl])-N$^2$-(carboxymethyl)-guanine (IIIf)

To 75 mmol of 95% sodium hydride was added about 100 mL of freshly distilled tetrahydrofuran. The solution was cooled in an ice bath for 20 minutes and then 75 mmol of 3-hydroxypropionitrile was added. Reaction was stirred at 0° C. for 2 hours and then 15 mmol of 2-(N-[2-(methylthio)-ethyloxycarbonyl])-amino-6-chloro-N$^9$-(benzylcarboxymethyl)-purine (Iif) was added. The reaction was allowed to stir overnight while warming to room temperature. In the morning, the solvent was completely evaporated and then a solution containing 200 mL of water, 54 grams of sodium chloride and 8 grams of K$_2$S$_2$O$_7$ was added. The solution was stirred briskly for 15 minutes and then the solid product filtered off. The product as purified by boiling in acetonitrile. Yield 83%.
$^1$HNMR (d$_6$DMSO) δ 11.52 (1 H, s), 11.37 (1 H, s) 7.93 (1 H, s), 4.9 (2 H, s), 4.35 (2 H,t), 2.785 (2 H,t), 2.15 (3 H,s)

Example 16
Synthesis of Ethyl 2-(1'-cytosyl)acetate (XV)

To 2.5 mole of cytosine was added 2.5 L of dry dimethylformamide (DMF) and 2.75 mole of potassium-tert-butoxide. The reaction was heated to about 100° C. for 1–2 hours until the reaction turned light tan. The heat source was then removed, and the solution was cooled to less than 10°

C. in an ice bath. To the rapidly stirring solution was then added dropwise (over 30 to 40 minutes) 2.8 mole of ethylbromoacetate. After addition, the reaction as allowed to stir overnight while warming to room temperature. In the morning, the reaction was neutralized by the addition of 30 mL of acetic acid. The solvent was then removed by evaporation and the residue put under high vacuum for several days to remove all traces of DMF. The residue was then re-suspended in 2.5 L of water and stirred for 3 hours. The solid product was collected by vacuum filtration and washed with several volumes of water. Yield: 342.7 grams (70%).
$^1$H NMR (DMSO-$d_6$): δ 7.56 (d,1 H), 7.18 (s, 2 H), 5.68 (d,1 H), 4.43 (s, 2 H), 4.13 (q, 2 H), 1.19 (t, 3 H).

Example 17
Synthesis of Ethyl 2-[$N'^4$-benzhydroloxycarbonyl(1'-cytosyl)]acetate (XVI)

To 1.8 mole of ethyl 2-(1'-cytosyl)acetate was added 3.5 L of DMF and 2.9 mole of carbonyldiimidazole. The reaction was stirred for 1.5 hours at room temperature. Thin layer chromatography (tlc) analysis of a methanol quenched reaction sample indicated isocyanate formation had proceeded well. To the reaction was added 432 grams of benzhydrol, and the reaction was heated to 60° C. The temperature was maintained at 60° C. for about 6 hours and then an additional 80 grams of benzhydrol was added in two portions (1 hour apart). Let the reaction stir overnight while cooling to room temperature. In the morning, 100 mL of methanol was added to quench the reaction. The solvent was then completely evaporated. The red oil residue was recrystallized from 2.5 L of ethanol (372.2 grams impure white crystal). The mother liquor was evaporated and recrystallized from 2 L of 3/1 methanol/water (222 grams of product). The two crops of impure material were combined and recrystallized from 2.5 L of methanol. Yield: 565 grams (77%)
$^1$H NMR (DMSO-$d_6$): δ 11.01 (s, 1 H), 8.02 (d, 1 H), 7.46–7.27 (m, 10 H), 6.98 (d,1 H) 6.79 (s, 1 H), 4.60 (s, 2 H), 4.13 (q, 2 H), 1.18 (t, 3 H)

Example 18
Synthesis of 2-[$N'^4$-benzhydroloxycarbonyl(1'-cytosyl)]acetic acid (XVII)

To 75 mmole of ethyl 2-[$N'^4$-benzhydroloxycarbonyl(1'-cytosyl)]acetate was added 150 mL of acetonitrile, 150 mL of methanol, 75 mL water and 75 mL of ethanol. This solution was heated until all solid dissolved and then cooled in an ice bath to less than 10° C. To the briskly stirring solution was added rapidly a solution containing 730 mmole of lithium hydroxide dissolved in 250 mL of water. The reaction was then allowed to stir for exactly 6 minutes and then quenched by the immediate addition of a solution containing 365 mmole of citric acid dissolved in 350 mL of water. The white solid precipitate was then collected by vacuum filtration and the precipitate washed with several volumes of water. Yield: 27.25 grams white solid (98%).
$^1$H NMR (DMSO-$d_6$): δ 8.00 (d,1 H), 7.46–7.24 (m, 10 H), 6.93 (d,1 H), 6.78 (s,1 H), 4.51 (s, 2 H).

Example 19
Synthesis of Ethyl 2-(9'-adenyl)acetate (X)

To 389 grams of oven-dried adenine suspended in 6 L of DMF was added 40 grams of sodium hydride. The reaction was stirred and the evolution of hydrogen gas was monitored. After stirring 15 minutes, an additional 42 grams of sodium hydride was added. After 1 hour of stirring, the reaction was very thick. An additional 1.5 L of DMF was added and then the reaction was allowed to stir for another 3 hours until all hydrogen gas had been evolved. To the briskly stirring solution was added 351 mL of ethylbromoacetate dropwise over 30 minutes. The reaction was maintained between 20–30° C. by cooling with an ice bath. Reaction was then allowed to stir overnight while warming to room temperature. The solvent was then removed by evaporation and 3 L of water was added. After stirring for I hour, the solid product was collected by vacuum filtration and washed with several volumes of water. The product was then suspended in 2 L of boiling ethanol and allowed to reflux for 45 minutes with stirring. After cooling to room temperature overnight, the solid was collected by vacuum filtration and washed with ethanol. Yield: 638 grams (68%).
$^1$H-NMR (DMSO-$d_6$): δ 8.14 (s,1 H), 8.10 (s,1 H), 7.22 (s, 2 H), 5.05 (s, 2 H), 4.18 (q, 2 H), 1.22 (t, 3 H)

Example 20
Synthesis of ethyl 2-[$N'^6$-benzhydroloxycarbonyl(9'-adenyl)]acetate (XI)

To 1.96 mole ethyl 2-(9'-adenyl)acetate and 2.95 mole carbonyldiimidazole was added 4 L of DMF. The reaction was slowly heated to 105° C. and then maintained at that temperature for 2 hours. (During the heating, initially everything dissolved, then the reaction became thick and finally began to thin again.) The temperature was reduced to 95° C. and then 2.94 mole of benzhydrol was added. All heat was removed and the reaction was allowed to stir overnight. In the morning, 2.5 volumes of water was added, and the reaction was stirred rapidly for 20 minutes until crystals formed. The solution was then stirred for 1 hour and the solid product was collected by vacuum filtration and washed with several volumes of water. The collected product was then recrystallized from 1.8 L of boiling methanol. Yield: 630 grams (75%).
$^1$H-NMR (DMSO-$d_6$): δ 10.9 (s, 1 H), 8.6 (s, 1 H), 8.42 (s, 1 H), 7.53–7.23 (m, 10 H), 6.81 (s, 1 H), 5.1 (s, 2 H), 4.2–4.0 (q, 2 H), 1.2–1.1 (t, 3 H).

Example 21
Synthesis of 2-[$N'^6$-benzhydroloxycarbonyl(9'-adenyl)] acetic acid (XII)

To 300 grams of ethyl 2-[$N'^6$-benzhydroloxycarbonyl(9'-adenyl)]acetate was added 1.5 L of ethanol and 1.5 L of acetonitrile. The solution was heated until all of the solid dissolved and then 1 L of water was added. The reaction was then cooled in an ice bath to less than 10° C. To the briskly stirring mixture was added a solution containing 294 grams of lithium hydroxide dissolved in 2.5 L of water (the reaction temperature rose to 20° C.). The reaction was stirred for exactly 6 minutes (reaction became dear and the temperature was now about 25° C.) and then a solution containing 1,346 grams of citric acid dissolved in 3 L of water was immediately added. After about 10 minutes of stirring, seed crystals were added and the product crystallized. Thereafter, an additional 1 L of water was added, and while cooling in an ice bath, reaction was allowed to stir for an additional 30 minutes. The product was then collected by vacuum filtration and washed with water. Yield: 251 grams (89.5%). Reaction was repeated under identical conditions. Yield: 257.6 grams (92%).
$^1$H-NMR (DMSO-$d_6$): δ 11.78 (s, 1 H), 10.90 (s, 1 H), 8.60 (s,1 H), 8.42 (s, 1 H), 7.54–7.27 (m, 10 H), 6.81 (s, 1 H), 5.07 (s, 2 H).

Example 22
Synthesis of N-[N'-fluorenylmethyloxycarbonyl-(2'-aminoethyl)]glycine To a stirred suspension of finely powdered N-(2'-aminoethyl)-glycine (50 g, 0.423 mol) in 850 mL of dichloromethane and 50 mL of dimethylformamide (DMF) was added chlorotrimethylsilane (134 mL, 1.05 mol). The mixture was stirred for 40 min then cooled in an ice bath to 5° C. Finely powdered 9-fluorenylmethyl succinimidyl carbonate (134 g, 0.4 mol) was then added to the mixture followed by addition of N-methylmorpholine (186 mL, 1.68 mol) dropwise over a period of 30 min. After a further 2 hr had passed, 100 mL of methanol added. After a further period of 20 min, 1 L of ethyl acetate was then added. Twenty minutes later, the suspension was filtered and the collected solid was washed with ethyl acetate and partially dried in vacuo. The solid was then suspended in 1.5 L of water with rapid agitation for 1 hour. The remaining white solid was collected by filtration, washed with water and suspended in 1 L of methanol with vigorous agitation. The product was recovered by filtration, washed with methanol, and dried in vacuo. Yield: 80.6 g of N-[N-fluorenylmethyloxycarbonyl-(2-aminoethyl)]-glycine, (53%)

$^1$H-NMR (CDCl$_3$ w/1 drop of TFA): δ 8.3 (s, 1 H), 7.9–7.2 (m, 8 H), 6.2–6.0 (m, 1 H), 4.7 (s, 1 H), 4.3 (d, 1 H), 4.2 (m, 1 H), 3.9 (m, 1 H), 3.5 (m, 2 H), 3.3 (s, 1 H), 3.0 (m, 1 H), 2.4 (s, 1 H,)

Example 23
Synthesis of methyl N-[N'-fluorenylmethyloxycarbonyl-(2'-aminoethyl)]glycinate hydrochloride:

To a stirred, cooled suspension of N-[N'-fluorenylmethyloxycarbonyl-(2'-aminoethyl)]glycine (12 g, 35.29 mmol) in 100 mL of methanol was added dropwise 7.72 mL of thionyl chloride under argon. The reaction mixture was stirred for 15 min. at 0° C., then refluxed for 11/2 hr. The solvent was removed, in vacuo and the residue dissolved in a mixture of ether/methanol (9:1). The solution was cooled to 0° C. and stirred for 1 hr. A white solid precipitated which filtered, rinsed thoroughly with ether and dried. 12.4 g (90%) of the desired product was obtained.

$^1$H-NMR (DMSO-d$_6$): δ 9.5 (s, 2 H), 7.9–7.2 (m, 9 H), 4.3 (d, 2 H), 4.2 (m, 1 H), 4.0 (s, 2 H), 3.7 (s, 3 H), 3.3 [s, 2 H], 3.0 (t, 2 H).

Example 24
N-[N"-fluorenylmethyloxycarbonyl-(2"-aminoethyl)]-N-[2-[N'$^4$-benzhydroloxycarbonyl(1'-cytosyl)]acetyl]glycine or N-[N"-Fmoc-(2"-aminoethyl)]-N-[2-[N'$^4$-Bhoc(1'-cytosyl)]acetyl]glycine (XVIII)

To 380.2 μL(3.08 mmol) of pivaloyl chloride was added dropwise and under argon to a solution of 1.1 g (2.94 mmol ) of 2-(N'$^4$-Bhoc-1-cytosyl)acetic acid and 646.5 μL (5.88 mmol) of NMM in 10 mL of acetonitrile. The resulting mixture was stirred for 20 min at 0° C. 1 g ( 2.94 mmol) of finely ground N-Fmoc-aminoethylglycine was suspended in 10 mL of acetonitrile/water (7:3) mixture in a separate flask. Triethylamine was added dropwise to the vigorously stirred suspension until a clear solution was obtained. The two solutions were then combined and the resulting mixture stirred for 30 min. at room temperature. The flask was placed in an ice-bath and acidified to pH 3 with 20% citric acid. After stirring overnight the title compound was isolated by filtration and thoroughly washed with water. The yield was 1.84 g (89.3%) of white solid after drying, in vacuo.

$^1$H-NMR (DMSO-d$_6$): δ 10.9 (s, 1 H), 7.9–7.7 (m, 3 H), 7.7 (d, 2 H), 7.5–7.3 (m, 15 H), 6.9 (d, 1 H), 6.8 (s, 1 H), 4.6 (s, 2 H), 4.3–4.2 (m 3 H), 3.7 (s, 2 H), 3.3 [s, 2 H], 3.1 (m, 2 H).

Example 25
N-[N"-fluorenylmethyloxycarbonyl-(2"-aminoethyl)]-N-[2-(1'-thyminyl)acetyl]glycine or N-[N"-Fmoc-(2"-aminoethyl)]-N-[2-(1'-thyminyl)acetyl]glycine To 190.1 μL (1.54 mmol) of pivaloyl chloride was added dropwise under argon to a stirred, pre-cooled solution of 270 mg (1.47 mmol) of 2-(1'-thyminyl)acetic acid and 323 μL (2.94 mmol) NMM in 5 mL of acetonitrile. The resulting mixture was stirred at 0° C. for 25 min. In a separate flask, 0.5 g (1.47 mmol) of N-[N'-fluorenylmethyloxycarbonyl-(2'-aminoethyl)]glycine was suspended in 7 mL of acetonitrile/water (4:3) mixture followed by the dropwise addition of triethylamine until a complete dissolution was obtained. The two solutions were then mixed and the resulting mixture stirred at room temperature for 30 min. The flask was placed in an ice-bath and acidified to pH 2 with 3N HCl. After stirring for overnight, 490 mg (65% ) of the desired monomer was obtained as a white solid;

$^1$H-NMR (DMSO-d$_6$) δ 1.7 (s, 3 H), 3.1–3.3 (m, 4 H), 3.9 (s, 2 H), 4.1–4.6 (m, 5 H), 7.2–7.8 (m, 10 H), 11.2 (s, 1 H).

Example 26
N-[N"-fluorenylmethyloxycarbonyl-(2"-aminoethyl)]-N-[2-[N'$^6$-benzhydroloxycarbonyl(9'-adenyl)]acetyl]glycine or N-[N"-Fmoc-(2"-aminoethyl)]-N-[2-[N'$^6$-Bhoc(9'-adenyl)]acetyl]glycine (XIII)

To 2.32 g(5.75 mmol) of 2-[N'$^6$-Bhoc(9'-adenyl)]acetic acid in 15 mL of acetonitrile was added in one portion 1.3 mL of N-methylmorpholine at room temperature and the resulting mixture stirred for 5 min. The mixture was cooled to 0° C., and pivaloyl chloride (716 μL, 5.81 mmol) was added dropwise under argon. The reaction mixture was stirred for 20 min. In a separate flask, 2.00 g(5.88 mmol) of finely ground N-[N'-fluorenylmethyloxycarbonyl-(2'-aminoethyl)]glycine was suspended in 20 mL of a mixture of acetonitrile/water (1:1). Triethylamine was added dropwise to the vigorously stirred suspension until a clear solution was obtained. The two solutions were then combined and the resulting mixture stirred for 15 min at room temperature. The solution was diluted with ethyl acetate and then washed with brine. The aqueous layer was back extracted four times with ethyl acetate. The combined organic layer was washed once with brine, dried over MgSO$_4$, and evaporated to dryness, in vacuo. The residue was dissolved in a minimum amount of methanol and the product precipitated from ice-water. 3.65 g (87.5%) of the desired monomer was obtained. The crude material was recrystallized from a mixture of dioxane/ether.

$^1$H NMR (DMSO) δ 3.1–3.3 (m, 4 H), 3.9 (s, 2 H), 4.2–4.3 (m, 3 H), 5.1 (s, 2 H), 6.8 [s, 1 H], 7.2–8.5 (m, 21 H), 10.9 (s, 1 H)

Example 27
N-[N"-fluorenylmethyloxycarbonyl-(2"-aminoethyl)]-N-[2-[N'$^2$-benzhydroloxycarbonyl(9'-guanyl)]acetyl]glycine or N-[N"-Fmoc-(2"-aminoethyl)]-N-[2-[N'$^2$-Bhoc(9'-guanyl)]acetyl]glycine (VIII)

To 246.5 mg(0.588 mmol) of 2-[N'$^2$-Bhoc(9'-guanyl)] acetic acid was suspended in 5 mL of a mixture of acetonitrile/DMF (3:2) and added 130 μL(1.18 mmol) of NMM. The mixture was stirred at RT. for 5 min. The reaction was cooled to 0° C., and pivaloyl chloride (73.8 μL, 0.6 mmol) was added dropwise under argon. The resulting solution was stirred at 0° C., for 20 min. In a separate flask, 200 mg(0.588 mmol) of N-[N'-fluorenylmethyloxycarbonyl-(2'-aminoethyl)]glycine was suspended in 5 mL of a mixture of acetonitrile/water (3:2). Triethylamine was added dropwise to the vigorously stirred suspension until a clear solution was obtained. The two solutions were then mixed together and stirred for 10 min at room temperature. The reaction mixture was acidified to pH 4 with 20% citric acid. The solvent was removed, in vacuo and the residue dissolved in a minimum amount of methanol. The methanol solution was added dropwise to an ice-water under vigorous stirring. 320 mg (73.4%) of the desired monomer was obtained.
$^1$H NMR δ 3.1–3.5 (m, 4 H), 3.9–5.0 (m, 7 H), 6.8 [s, 1 H], 7.2–7.9 (m, 21 H), 11.2 (s, 1 H)

Example 28
Methyl N-[N"-Fmoc-(2"-aminoethyl)]-N-[2-[N'$^2$-Bhoc(9'-guanyl)]acetyl]glycinate (IX)

To 1.07 g(2.56 mmol) of (N-2-Bhoc-9-guanyl) acetic acid in 10 mL of a mixture of acetonitrile/DMF (1:1) was added 844 μL(7.68 mmol) of NMM. The solution was cooled to 0° C., and pivaloyl chloride (331 μL, 2.68 mmol) was added dropwise under argon. The reaction mixture was stirred at 0° C. for 25 min. and then 1 g(2.56 mmol) of methyl N-[N'-fluorenylmethyloxycarbonyl-(2'-aminoethyl)]glycinate was added in one portion. The resulting mixture was stirred overnight at room temperature. After stirring overnight a white solid had precipitated which was filtered, washed with a mixture acetonitrile/water (1:2) and dried. 1.25 g(64.7%) of the desired monomer methyl ester was obtained.
$^1$H NMR δ 3.1–3.3 (m, 4 H), 3.6 (s, 3 H), 3.7–5.1 (m, 7 H), 6.8 (s, 1 H), 7.2–7.8 (m, 19 H), 11.2 (s, 1 H), 11.6 (s, 1 H)

Example 29
N-[N"-Fmoc-(2"-aminoethyl)]-N-[2-[N'$^2$-Bhoc(9'-guanyl)]acetyl]glycine (VIII)

To a stirred, cooled suspension of methyl N-[N"-Fmoc-(2"-aminoethyl)]-N-[2-[N'$^2$-Bhoc(9'-guanyl)]acetyl]glycinate (1.19 g, 1.57 mmol) in 10 mL of acetone/water (8:2) was added in one portion 6.3 mL of 2.5N LiOH. The resulting mixture was stirred for exactly 5 min. at 0° C., neutralized with 20% citric acid and then the pH was raised to 8 with sat. NaHCO$_3$ solution. 115 mg of Fmoc-succinimide was added in one portion and the reaction mixture stirred at room temperature for 30 min. The solution was extracted twice with ether after which the aqueous phase was acidified to pH 3 with 20% citric acid. The solution was extracted several times with ethyl acetate and the combined organic phase was washed with brine, dried over MgSO$_4$, evaporated to dryness, in vacuo. The residue was triturated with ether. 758 mg(65/o) of the desired monomer was isolated as a white solid. The $^1$H NMR was identical to the sample obtained by the direct coupling method.

Example 30
Methyl N-[N"-Fmoc-(2"-aminoethyl)]-N-[2-[N'$^6$-Bhoc(9'-adenyl)]acetyl]glycinate (XIV)

To 2 g(4.96 mmol) of 2-[N'$^6$-Bhoc(9'-adenyl)]acetic acid in 10 mL of acetonitrile/DMF (1:1) was added 1.64 mL(14.88 mmol) of NMM. The solution was cooled to 0° C., and pivaloyl chloride (672 μL, 5.45 mmol) was added dropwise under argon. The reaction mixture was stirred at 0° C. for 25 min. 2.27 g(4.85 mmol) of Fmoc-aminoethylglycine methyl ester TFA salt was added in one portion and the resulting mixture stirred at room temperature for 3 hr. The reaction mixture was then slowly added to 100 mL of ice-water. A white solid precipitated which was filtered and dried. 3.5 g (95.6%) of the desired monomer methyl ester was obtained.
$^1$H NMR δ 3.1–3.3 (m, 4 H), 3.6 (s, 3 H), 3.7–5.3 (m, 7 H), 6.8 [s, 1 H], 7.2–8.5 (m, 21 H), 10.8 (s, 1 H)

Example 31
N-[N"-Fmoc-(2"-aminoethyl)]-N-[2-[N'$^6$-Bhoc(9'-adenyl)]acetyl]glycine (XIII)

To a stirred, pre-cooled suspension of methyl N-[N"-Fmoc-(2"-aminoethyl)]-N-[2-[N'$^6$-Bhoc(9'-adenyl)]acetyl]glycinate (2 g, 2.7 mmol) in 15 mL of acetone/water (10:5) was added in one portion 11 mL of 2.5N LiOH. The resulting mixture was stirred for 7 min. at 0° C., neutralized with 20% citric acid and then the pH was raised to 8 with sat. NaHCO$_3$ solution. 200 mg of Fmoc-succinimide was added in one portion and the reaction mixture stirred at room temperature for 11/2 hr. The solution was extracted three times with ether after which the aqueous phase was acidified to pH 3 with 20% citric acid. The solution was extracted several times with ethyl acetate and the combined organic layer washed with brine, dried over MgSO$_4$, evaporated to dryness, in vacuo. The residue was triturated with ether and gently warmed. The title compound was isolates as an off white solid 1.5 g(77%) after filtration and drying. The $^1$H NMR was identical to the sample obtained by the direct coupling method.

Example 31
Methyl N-[N"-Fmoc-(2"-aminoethyl))-N-[2-[N'$^4$-Bhoc(1'-cytosyl)]acetyl]glycinate (XIX)

To 4 g(10.5 mmol) of 2-[N'$^4$-Bhoc(1'-cytosyl)]acetic acid in 30 mL of a mixture of acetonitrile/DMF (1:1) was added 3.5 mL(31.6 mmol) of NMM. The solution was cooled to 0° C., and pivaloyl chloride (1.44 mL, 11.6 mmol) was added dropwise under argon. The reaction mixture was stirred at 0° C. for 20 min. 4.44 g (9.48 mmol) of Fmoc-aminoethylglydne methyl ester TFA salt was added in one portion and the resulting mixture stirred at room temperature for overnight. A white solid precipitated which was filtered, rinsed thoroughly with warm acetonitrile and dried. 6.4 g (84.8%) of the desired monomer methyl ester was isolated.
$^1$H NMR (DMSO) δ 3.1–3.4 (m, 4 H), 3.6 (s, 3 H), 3.7–4.8 (m, 7 H), 6.7 [s, 1 H], 6.8–7.9 (m, 21 H), 10.9 (s, 1 H).
$^1$H NMR data in brackets [ ] indicates that peaks are superimposed on other proton sources.

Example 32
N-[N"-Fmoc-(2"-aminoethyl)]-N-[2-[N'$^4$-Bhoc(1'-cytosyl)]acetyl]glycine (XVII)

To a stirred, pre-cooled suspension of Methyl N-[N"-Fmoc-(2"-aminoethyl)]-N-[2-[N'$^4$-Bhoc(1'-cytosyl)]acetyl]glycinate (3 g, 4.19 mmol) in 45 mL of a mixture of acetonitrile/acetone/water (1:1:1) was added in one portion 16.7 mL of 2.5N LiOH. The resulting mixture was stirred for 10 min. at 0° C., neutralized with 20% citric acid and then the pH was raised to 8 with sat. NaHCO$_3$ solution. 300 mg of Fmoc-succinimide was added in one portion and the reaction mixture stirred at room temperature for 2 hr. The flask was placed in an ice-bath and acidified to pH 3 with 20% citric acid. After stirring at 0° C. for ½ hr, a white solid precipitated which was filtered and dried. This material resuspended in acetonitrile and heated. 1.8 g(61.4%) of the desired product was obtained. The $^1$H NMR was identical to the sample obtained by the direct coupling method.

Example 33
Synthesis of Ethyl 2[N'$^4$-tert-butoxycarbonyl (1'cytosyl)]acetate 3 g (15.22 mmol) of ethyl 2-(1'cytosyl)acetate was stirred at room temperature for 2 hours with 2.96 g (18.25 mmol) of 1,1'-carbonyldiimidazole in 50 ml of DMF. tert-Butyl alcohol (7 ml, 73.19 mmol) was then added in one portion and the resulting mixture heated to 80° C. for 2 hours. The solvent was removed in vacuo and the residue taken up in acetonitrile and again the solvent was removed. The resulting brown oil was ten dissolved in 100 ml of acetonitrile and used directly for next step without further purification.

Example 34

Synthesis of 2-[N'⁴tert-butoxycarbonyl (1'-cytosyl)]acetic acid

The crude ester of the above-mentioned reaction was subjected to hydrolysis with 30 ml of LiOH (2.5N). The mixture was stirred at room temperature for 10 min. by which time the TLC showed complete disappearance of the ester. The solution was acidified to pH with 20% citric acid and mixture left stirring for overnight. The solution was filtered and the filtrate extracted with ethyl acetate. The combined organic solution was concentrated and was left standing at room temperature for overnight. 1 g of the desired product was isolated. $^1$H-NMR (d$_6$ DMSO) δ 7.98 (d, 1 H), 6.97 (d, 1 H), 4.47 (s, 2 H), 1.44 (s, 9 H).

Example 35

Synthesis of N-[N''-fluorenylmethyloxycarbonyl-(2''-aminoethyl)]-N-[2-[N'⁴tert-butoxycarbonyl(1'cytosyl]acetyl]glycine 233 μl (1.88 mmol) of pivaloyl chloride was added dropwise o a precooled mixture of 2-(N'⁴tert-butoxycarbonyl-1-cytosyl)acetic acid (0.5 g, 1.85 mmol) and N-methylmorpholine (406, 3.7 mmol) in 7 ml of acetonitrile. The resulting mixture was stirred for 20 min at 0° C. 0.6 g (1.76 mmol) of finely ground N-Fmoc-aminoethylglycine was suspended in 10 ml of acetonitrile/water (1:1) mixture in a separate flask. Triethylamine was added dropwise to the vigorously stirred suspension until a clear solution was obtained. The two solutions were then combined and the resulting mixture was stirred for 20 min. at room temperature. The flask was placed in an ice-bath and acidified to pH 3 with 20% citric acid. The product was extracted with ethyl acetate and the combined ethyl acetate solution was washed once with brine. The ethyl acetate was evaporated and the residue dissolved in methanol which was again removed in vacuo. Finally the product was taken up in 4 ml of methanol and added dropwise to an ice-cold water (~100 ml). An off-white solid precipitated which was filtered and dried. 825 mg (79.3%) of the desired monomer was obtained. $^1$H-NMR (d$_6$ DMSO) δ 10.3 (bs, 1 H), 7.89–7.78 (m, 3 H), 7.68 (d, 2 H), 7.43–7.27 (m, 4 H), 6.97–6.92 (dd, 1 H), 4.79 (bs, 4/3 H), 4.60 (bs, 2/3 H), 4.34 (m, 4 H), 3.98 (bs, 2 H), 3.39 [m, 4 H], 1.44 (s, 9 H).

Example 36

Solid phase synthesis of PNA oligomers using Fmoc/Bhoc protected monomers:

The sequence H-CAG GAG TCG CAT gly-NH2 was synthesized manually on an Fmoc-Pai-Peg-PS (PerSeptive Biosystems P/N GEN 913383: 100 mg, 0.17 mmol/g loading) according to the following synthesis cycle. All reactions and washes of the resin were performed in a fritted vial. Reagent and wash solutions were added to the vial containing the synthesis resin and allowed to react. At designated time intervals the solutions were removed by vacuum filtration through the frit.

Synthetic Cycle

1) Deprotection with 20% piperidine in DMF for 10 min.
2) Wash with DMF 3 times followed by 2 washes with dichloromethane (DCM)
3) Coupling with 3 equiv. of the appropriate monomer (0.1 M in DMF). Activation was initiated by addition of 3 equiv. O-7-azabenzotriazol-1-yl)-1,1,3,3,-tetramethyluronium hexafluorophosphate (HATU) and 3 equiv. of diisopropylethylamine (DIEA). The activated mixtures was added immediately to the resin and the coupling was allowed to proceed for 30 minutes.
4) Wash with DMF 3 times followed by 2 washes with dichloromethane (DCM)

Figure 6:
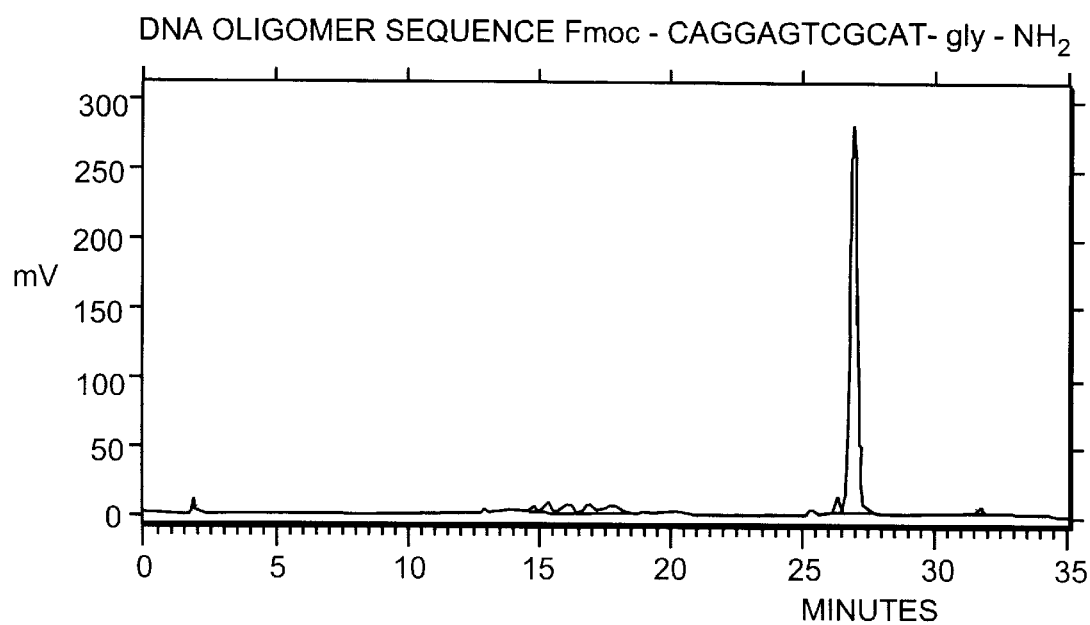
FIG. 6 is an HPLC trace of the PNA oligomer sequence Fmoc-CAGGAGTCGCAT-gly-$NH_2$.

Each step was monitored by performing a ninhydrin (Kaiser) test after each coupling. Only, in the case of the first adenine (pos. 3) was a second coupling necessary. The final Fmoc group was retained on the oligomer which was cleaved from the resin for analysis. The removal the Bhoc protection groups and cleavage from the resin was accomplished in one step by treatment with TFA/m-cresol (4:1) for 90 minutes. The cleavage was performed in an Ultrafree device (Millipore P/N SE3P230J3). After completed cleavage the resin was retained by centrifugation and the crude PNA oligomer was isolated the addition of 2 vol. of diethyl ether to the TFA/m-cresol. The crude PNA oligomer was washed twice with diethyl ether. HPLC (260 nm) analysis of the crude product under standard conditions revealed a purity of 83%, the major impurities being a deletion without adenine (3.8%) (See FIG. 6). The identity of the product was confirmed by Matrix Assisted Laser Desorption-Time of Flight (MALDI-TOF) Mass Spectrometer and a mass of 3571.3 atomic mass units (amu) was observed compared to the calculated mass of 3573.1 amu within the 0.1% accuracy of the instrument.

The invention may be embodied in other specific forms.

What is claimed is:

1. A compound having the formula:

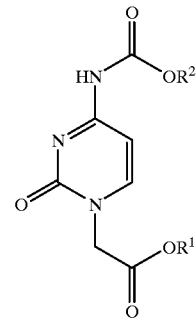

wherein

R$^1$ is selected from the group consisting of hydrogen, methyl, ethyl, 2,2,2-trichloroethyl, 2-(trimethylsilyl)-ethyl, 2-(phenylthio)-ethyl, propyl, isopropyl, n-butyl, t-butyl, allyl, 1-isopropyl allyl, cinnamyl, 4-nitrocinnamyl and a substituted benzyl of the formula:

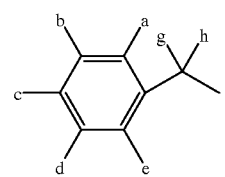

wherein the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, NO$_2$,—SO$_3$H, —CN, —SCH$_3$, and —(O)

SCH₃ such that at least one of the atoms or groups represented by a–e is not hydrogen; and the atom or group represented by each of g–h is the same or different and is independently selected from the group consisting of hydrogen and methyl; and R² is independently selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a substituted benzyl as set forth above, a diphenylmethyl group of the formula:

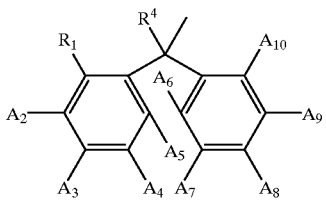

wherein each of A₁–A₁₀ is independently selected from the group consisting of F, Cl, Br, I, hydrogen, methyl, ethyl, methoxy and ethoxy, and R⁴ is selected from the group consisting of hydrogen, methyl and ethyl;

a thioether group of the formula:

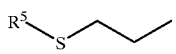

wherein

R⁵ is selected from the group consisting of methyl, ethyl, propyl, isopropyl, n-butyl, t-butyl and a phenyl group, wherein the phenyl group is a group of the formula:

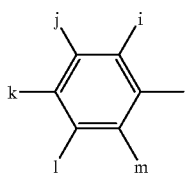

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, NO₂, —SO₃H, —CN, —SCH₃, and —(O)SCH₃; and a substituted ethyl group of the formula:

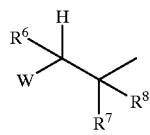

wherein W is selected from the group consisting of cyano, alkylsulfonyl, arylsulfonyl, phenyl, p-nitrophenyl, o-nitrophenyl, and p-alkylsulfonylphenyl; and R⁶–R⁸ are the same or different and are independently selected from the group consisting of hydrogen, methyl, ethyl, n-propyl, isopropyl, n-butyl and t-butyl.

2. A compound having the formula:

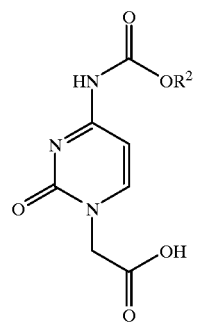

wherein

R² is independently selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl, a substituted benzyl of the formula:

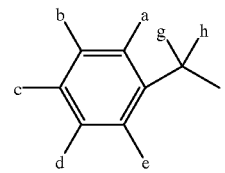

wherein the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, NO₂, —SO₃H, —CN, —SCH₃, and —(O)SCH₃ such that at least one of the atoms or groups represented by the a–e is not hydrogen; and the atom or group represented by each of g–h is the same or different and is independently selected from the group consisting of hydrogen and methyl, a diphenylmethyl group of the formula:

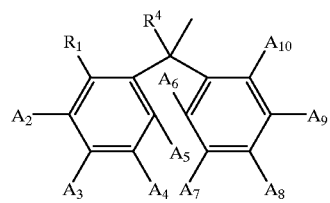

wherein each of A₁–A₁₀ is independently selected from the group consisting of F, Cl, Br, I, hydrogen, methyl, ethyl, methoxy and ethoxy, and R⁴ is selected from the group consisting of hydrogen, methyl and ethyl;

a thioether group of the formula:

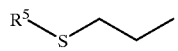

wherein

R⁵ is selected from the group consisting of methyl, ethyl, propyl, isopropyl, n-butyl, t-butyl and a phenyl group, wherein the phenyl group is a group of the formula:

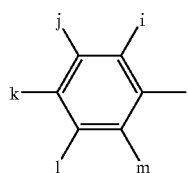

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, NO₂, —SO₃H, —CN, —SCH₃, and —(O)SCH₃; and a substituted ethyl group of the formula:

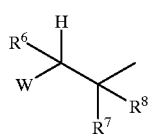

wherein W is selected from the group consisting of cyano, alkylsulfonyl, arylsulfonyl, phenyl, p-nitrophenyl, o-nitrophenyl, and p-alkylsulfonylphenyl; and $R^6$–$R^8$ are the same or different and are independently selected from the group consisting of hydrogen, methyl, ethyl, n-propyl, isopropyl, n-butyl and t-butyl.

3. The compound of claim 1 having the formula:

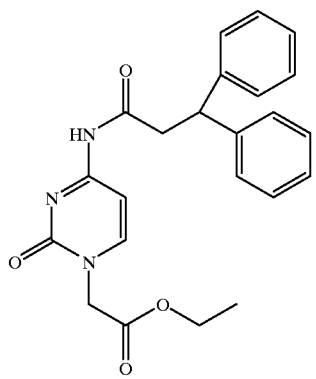

4. The compound of claim 2 having the formula:

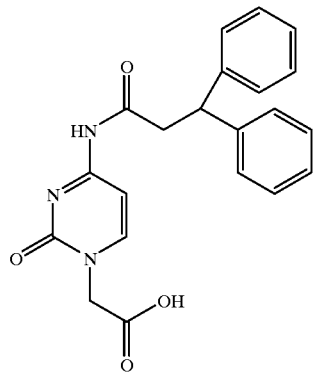

5. A PNA synthon or PNA synthon ester having the formula:

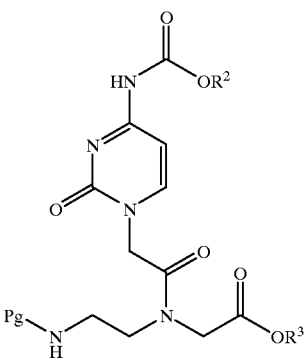

wherein

Pg is a protecting group selected from the group consisting of alkyloxycarbonyl, 9-fluorenylmethyloxycarbonyl, 1-methyl-1-(4-biphenyl)-ethyloxycarbonyl, 1-methyl-1-phenylethyloxycarbonyl, triphenylmethyl, 4-methoxy-triphenylmethyl, and 4,4'-dimethoxy-triphenylmethyl;

$R^2$ is selected from the group consisting of methyl, ethyl, 2,2,2-trichloro ethyl, 2-(trimethylsilyl)-ethyl, propyl, isopropyl, n-butyl, t-butyl, allyl, 1-isopropyl allyl, cinnamyl, 4-nitrocinnamyl, a substituted benzyl of the formula:

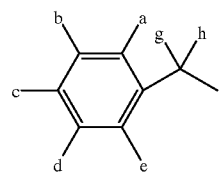

wherein
  the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, $NO_2$, $—SO_3H$, —CN, $—SCH_3$, and $—(O)SCH_3$ such that at least one of the atoms or groups represented by a–e is not hydrogen, and
  the atom or group represented by each of g–h is the same or different and is independently selected from the group consisting of hydrogen and methyl;
a diphenylmethyl group of the formula:

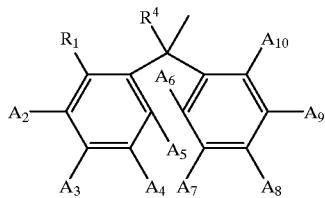

wherein each of $A_1$–$A_{10}$ is independently selected from the group consisting of F, Cl, Br, I, hydrogen, methyl, ethyl, methoxy and ethoxy, and
  $R^4$ is selected from the group consisting of hydrogen, methyl and ethyl;
a substituted ethyl group of the formula:

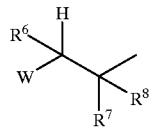

wherein W is selected from the group consisting of cyano, alkylsulfonyl, arylsulfonyl, phenyl, p-nitrophenyl, o-nitrophenyl, and p-alkylsulfonylphenyl, and
  $R^6$–$R^8$ are the same or different and are independently selected from the group consisting of hydrogen, methyl, ethyl, n-propyl, isopropyl, n-butyl and t-butyl;
and substituted ethyl group of the formula:

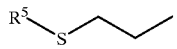

wherein $R^5$ is selected from the group consisting of methyl, ethyl, propyl, isopropyl, n-butyl, t-butyl and a phenyl group,
  wherein the phenyl group is a group of the formula:

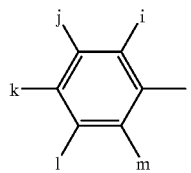

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, $NO_2$, $—SO_3H$, —CN, $—SCH_3$, and $—(O)SCH_3$; and $R^3$ is hydrogen or an alkyl group.

6. A PNA synthon ester of claim 5 having the formula:

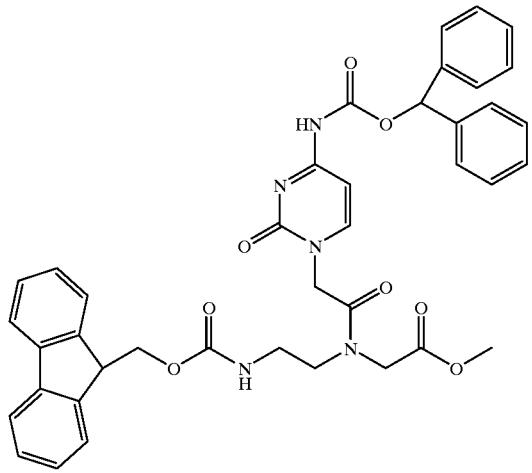

7. A PNA synthon of claim 5 having the formula:

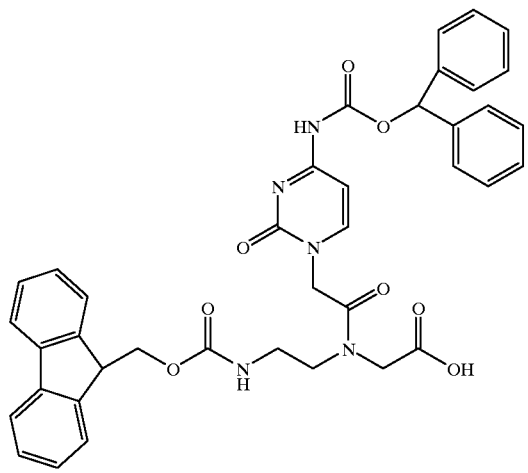

8. A PNA synthon of claim 5 having the formula:

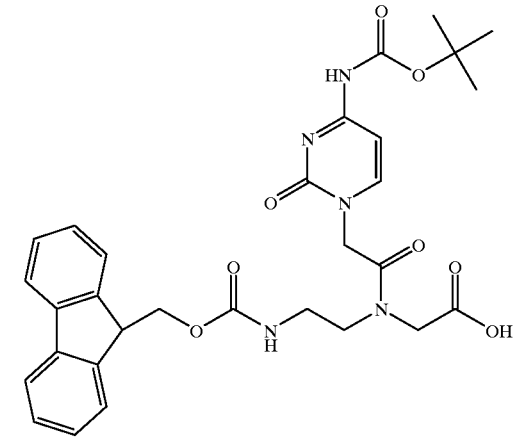

9. The compound of claim 2 having the formula:

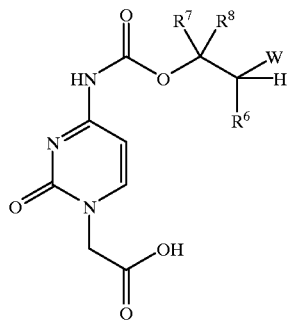

wherein

W is selected from the group consisting of cyano, alkylsulfonyl arylsulfonyl, phenyl, p-nitrophenyl, o-nitrophenyl, and p-alkylsulfonylphenyl; and $R^6$–$R^8$ are the same or different and are independently selected from the group consisting of hydrogen, methyl, ethyl, n-propyl, isopropyl, n-butyl and t-butyl.

10. The compound of claim 1, wherein $R^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl.

11. The compound of claim 1, wherein $R^2$ is a substituted benzyl of the formula:

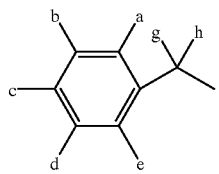

wherein the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, $NO_2$, —$SO_3H$, —CN, —$SCH_3$, and —(O)$SCH_3$ such that at least one of the atoms or groups represented by a–e is not hydrogen; and the atom or group represented by each of g–h is the same or different and is independently selected from the group consisting of hydrogen and methyl.

12. The compound of claim 1, wherein $R^2$ is a thioether group of the formula:

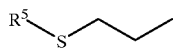

wherein $R^5$ is selected from the group consisting of methyl, ethyl, propyl, isopropyl, n-butyl, t-butyl and a phenyl group, wherein the phenyl group is a group of the formula:

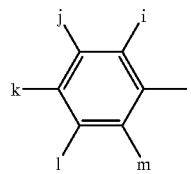

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, $NO_2$, —$SO_3H$, —CN, —$SCH_3$, and —(O)$SCH_3$.

13. The compound of claim 1, wherein $R^2$ is a diphenylmethyl group of the formula:

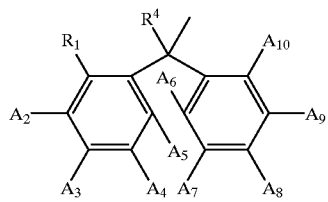

wherein each of $A_1$–$A_{10}$ is independently selected from the group consisting of F, Cl, Br, I, hydrogen, methyl, ethyl, methoxy and ethoxy, and $R^4$ is selected from the group consisting of hydrogen, methyl and ethyl.

14. The compound of claim 1, wherein $R^2$ is a substituted ethyl group of the formula:

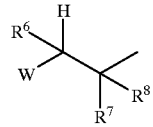

wherein W is selected from the group consisting of cyano, alkylsulfonyl, arylsulfonyl, phenyl, p-nitrophenyl, o-nitrophenyl, and p-alkylsulfonylphenyl; and $R^6$–$R^8$ are the same or different and are independently selected from the group consisting of hydrogen, methyl, ethyl, n-propyl, isopropyl, n-butyl and t-butyl.

15. The compound of claim 2, wherein $R^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl.

16. The compound of claim 2, wherein $R^2$ is a substituted benzyl of the formula:

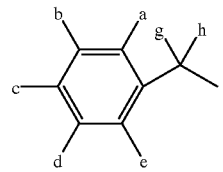

wherein the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, NO$_2$, —SO$_3$H, —CN, —SCH$_3$, and —(O)SCH$_3$ such that at least one of the atoms or groups represented by a–e is not hydrogen; and the atom or group represented by each of g–h is the same or different and is independently selected from the group consisting of hydrogen and methyl.

17. The compound of claim 2, wherein R$^2$ is a diphenylmethyl group of the formula:

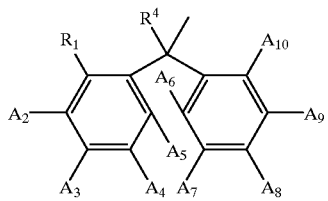

wherein each of A$_1$–A$_{10}$ is independently selected from the group consisting of F, Cl, Br, I, hydrogen, methyl, ethyl, methoxy and ethoxy, and R$^4$ is selected from the group consisting of hydrogen, methyl and ethyl.

18. The compound of claim 2, wherein R$^2$ is a thioether group of the formula:

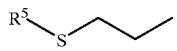

wherein

R$^5$ is selected from the group consisting of methyl, ethyl, propyl, isopropyl, n-butyl, t-butyl and a phenyl group, wherein the phenyl group is a group of the formula:

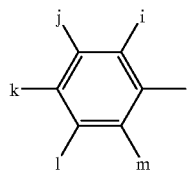

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, NO$_2$, —SO$_3$H, —CN, —SCH$_3$, and —(O)SCH$_3$.

19. The compound of claim 5, wherein R$^2$ is selected from the group consisting of methyl, ethyl, 2,2,2-trichloroethyl, 2-(trimethylsilyl)-ethyl, propyl, isopropyl, n-butyl, t-butyl, allyl, 1-isopropyl allyl, cinnamyl, 4-nitrocinnamyl.

20. The compound of claim 5, wherein R$^2$ is a substituted benzyl of the formula:

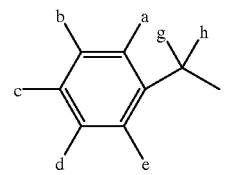

wherein the atom or group represented by each of a–e is the same or different and is independently selected from the group consisting of F, Cl, Br, I, hydrogen, methyl, ethyl, isopropyl, n-butyl, t-butyl, phenyl, methoxy, ethoxy, NO$_2$, —SO$_3$H, —CN, —SCH$_3$, and —(O)SCH$_3$ such that at least one of the atoms or groups represented by a–e is not hydrogen; and the atom or group represented by each of g–h is the same or different and is independently selected from the group consisting of hydrogen and methyl.

21. The compound of claim 5, wherein R$^2$ is a diphenylmethyl group of the formula:

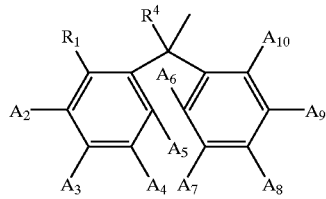

wherein each of A$_1$–A$_{10}$ is independently selected from the group consisting of F, Cl, Br, I, hydrogen, methyl, ethyl, methoxy and ethoxy, and R$^4$ is selected from the group consisting of hydrogen, methyl and ethyl.

22. The compound of claim 5, wherein R$^2$ a thioether group of the formula:

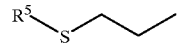

wherein

R$^5$ is selected from the group consisting of methyl, ethyl, propyl, isopropyl, n-butyl, t-butyl and a phenyl group, wherein the phenyl group is a group of the formula:

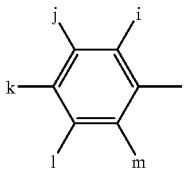

wherein the atom or group represented by each of i–m is the same or different and is independently selected from the group consisting of F, Cl, Br, I, hydrogen, methyl, ethyl, isopropyl, n-butyl, t-butyl, phenyl, methoxy, ethoxy, NO$_2$, —SO$_3$H, —CN, —SCH$_3$, and —(O)SCH$_3$.

23. The compound of claim 5, wherein $R^2$ is a substituted ethyl group of the formula:

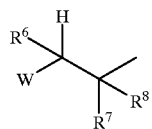

wherein W is selected from the group consisting of cyano, alkylsulfonyl, arylsulfonyl, phenyl, p-nitrophenyl, o-nitrophenyl, and p-alkylsulfonylphenyl; and $R^6$–$R^8$ are the same or different and are independently selected from the group consisting of hydrogen, methyl, ethyl, n-propyl, isopropyl, n-butyl and t-butyl.

* * * * *